United States Patent
Eshhar et al.

(10) Patent No.: US 9,623,049 B2
(45) Date of Patent: Apr. 18, 2017

(54) IMMUNOTHERAPY USING REDIRECTED ALLOGENEIC CELLS

(71) Applicant: YEDA RESEARCH AND DEVELOPMENT CO. LTD., Rehovot (IL)

(72) Inventors: Zelig Eshhar, Rehovot (IL); Assaf Marcus, Rehovot (IL); Tova Waks, Rehovot (IL)

(73) Assignee: YEDA RESEARCH AND DEVELOPMENT CO. LTD., Rehovot (IL)

(*) Notice: Subject to any disclaimer, the term of this patent is extended or adjusted under 35 U.S.C. 154(b) by 402 days.

(21) Appl. No.: 13/669,194

(22) Filed: Nov. 5, 2012

(65) Prior Publication Data

US 2013/0156794 A1 Jun. 20, 2013

Related U.S. Application Data

(63) Continuation-in-part of application No. PCT/US2011/035104, filed on May 4, 2011.

(60) Provisional application No. 61/331,325, filed on May 4, 2010.

(51) Int. Cl.

| | | |
|---|---|---|
| *A61K 35/26* | (2015.01) | |
| *A61K 35/28* | (2015.01) | |
| *A61K 38/00* | (2006.01) | |
| *A61K 35/17* | (2015.01) | |
| *A61K 31/137* | (2006.01) | |
| *A61K 31/197* | (2006.01) | |
| *A61K 31/4245* | (2006.01) | |
| *C12N 5/0783* | (2010.01) | |
| *A61K 31/135* | (2006.01) | |
| *A61K 31/185* | (2006.01) | |
| *A61K 31/196* | (2006.01) | |
| *A61K 31/661* | (2006.01) | |
| *A61K 31/675* | (2006.01) | |
| *A61K 31/7076* | (2006.01) | |
| *A61K 39/395* | (2006.01) | |
| *A61K 47/48* | (2006.01) | |
| *A61K 48/00* | (2006.01) | |
| *A61N 5/10* | (2006.01) | |
| *B82Y 5/00* | (2011.01) | |
| *A61K 35/12* | (2015.01) | |

(52) U.S. Cl.
CPC ............ *A61K 35/17* (2013.01); *A61K 31/135* (2013.01); *A61K 31/137* (2013.01); *A61K 31/185* (2013.01); *A61K 31/196* (2013.01); *A61K 31/197* (2013.01); *A61K 31/4245* (2013.01); *A61K 31/661* (2013.01); *A61K 31/675* (2013.01); *A61K 31/7076* (2013.01); *A61K 39/39541* (2013.01); *A61K 47/48369* (2013.01); *A61K 47/48723* (2013.01); *A61K 48/00* (2013.01); *A61N 5/10* (2013.01); *B82Y 5/00* (2013.01); *C12N 5/0638* (2013.01); *A61K 2035/124* (2013.01); *C12N 2501/2302* (2013.01); *C12N 2501/51* (2013.01); *C12N 2501/515* (2013.01); *C12N 2501/59* (2013.01)

(58) Field of Classification Search
None
See application file for complete search history.

(56) References Cited

U.S. PATENT DOCUMENTS

| | | | |
|---|---|---|---|
| 7,943,180 B2* | 5/2011 | Har-Noy | 424/578 |
| 2008/0267972 A1* | 10/2008 | Berenson | A61K 35/17 424/152.1 |
| 2010/0135974 A1* | 6/2010 | Eshhar et al. | 424/93.71 |
| 2010/0240732 A1* | 9/2010 | Gilboa | 514/44 A |

FOREIGN PATENT DOCUMENTS

WO 0031239 A1 6/2000

OTHER PUBLICATIONS

Dotti et al Human Gene Therapy, 2009, v.20, pp. 1229-1239.*
Sadelain et al., Current Opinion in Immunology, 2009, v.21, pp. 215-223.*
Friedmann-Morvinski et al Blood, 2005, v.105, pp. 3087-3093.*
Klebanoff et al Trends in Immunology, 2005, v.26 pp. 111-117.*
Figueiredo, C. et al., "Class-, gene-, and group-specific HLA silencing by lentiviral shRNA delivery.", Journal of Moledular Medicine, vol. 84, No. 5, pp. 425-437, Mar. 2006.
Kim, Yong-Mi et al., "Graft-versus-host disease can be separated from graft-versus-lymphoma effects by control of lymphocyte trafficking with FTY720", The Journal of Clinical Investigation, vol. 111, No. 5, pp. 659-669, Mar. 2003.
Wrzesinski, Claudia et al., "Less is more: lymphodepletion followed by hematopoietic stem cell transplant augments adoptive T-cell-based anti-tumor immunotherapy", NIH Public Access, Current Opinion in Immunology, vol. 17, No. 2, pp. 195-201, Apr. 2005.
Marcus et al., "Redirected tumor-specific allogeneic T cells for universal treatment of cancer" Blood, 118(4):975-983 (2011).
Boni et al., "Adoptive transfer of allogeneic tumor-specific T cells mediates effective regression of large tumors across major histocompatibility barriers", Blood, 112(12):4746-4754 (2008).
Freidmann-Morvinski et al., "Redirected primary T cells harboring a chimeric receptor require costimulation for their antigen-specific activation" Blood 105(8):3087-3093 (2005).

(Continued)

Primary Examiner — Michail Belyavskyi
(74) Attorney, Agent, or Firm — Browdy and Neimark, PLLC

(57) ABSTRACT

A method of treating a disease, such as cancer, by administering to a subject in need of such treatment an effective amount of allogeneic T cells with a MHC unrestricted chimeric receptor short time after partial lymphodepletion. The method also comprises administering one or more agents that delay egression of the allogeneic T cells from lymph nodes of said subject during adoptive transfer of said allogeneic T cells to the subject by trapping the T cells in the lymph nodes.

15 Claims, 23 Drawing Sheets
(22 of 23 Drawing Sheet(s) Filed in Color)

(56) References Cited

OTHER PUBLICATIONS

Zakrzewski et al. "Tumor immunotherapy across MHC barriers using allogeneic T-cell precursors", Nature Biotechnology, 26(4): 453-461 (2008).
Eshhar, Z., "The T-body approach: redirecting T cells with antibody specificity", Therapeutic Antibodies: Handbook of Experimental Pharmacology 181, Chernajovsky and Nissim, eds., Springer-Verlag Berlin Heidelberg 2008.
Gattinoni et al, "Removal of homeostatic cytokine sinks by lymphodepletion enhances the efficacy of adoptively transferred tumor-specific CD8+ T cells" J Exp Med 202(7):907-912 (2005).
Gattinoni et al, "Adoptive immunotherapy for cancer: building on success" Nature Reviews Immunology 6(5):383-393 (2006).
Dudley et al "Adoptive cell therapy for patients with metastatic melanoma: evaluation of intensive myeloablative chemoradiation preparative regimens" J Clin Oncol 26(32):5233-5239 (2008).
Torikai et al, "A foundation for universal T-cell based immunotherapy: T cells engineered to express a CD19-specific chimeric-antigen-receptor and eliminate expression of endogenous TCR" Blood, 119(24):5697-5706 (2012).
Galetto et al, "TCRab Deficient CAR T-Cells Targeting CD123: An Allogeneic Approach of Adoptive Immunotherapy for the Treatment of Acute Myeloid Leukemia (AML)." Blood 126.23: 2555-2555 (2015).
Muranski et al., "Increased intensity lymphodepletion and adoptive immunotherapy—how far can we go?" Nat Clin Pract Oncol 3(12):668-681 (2006).

\* cited by examiner

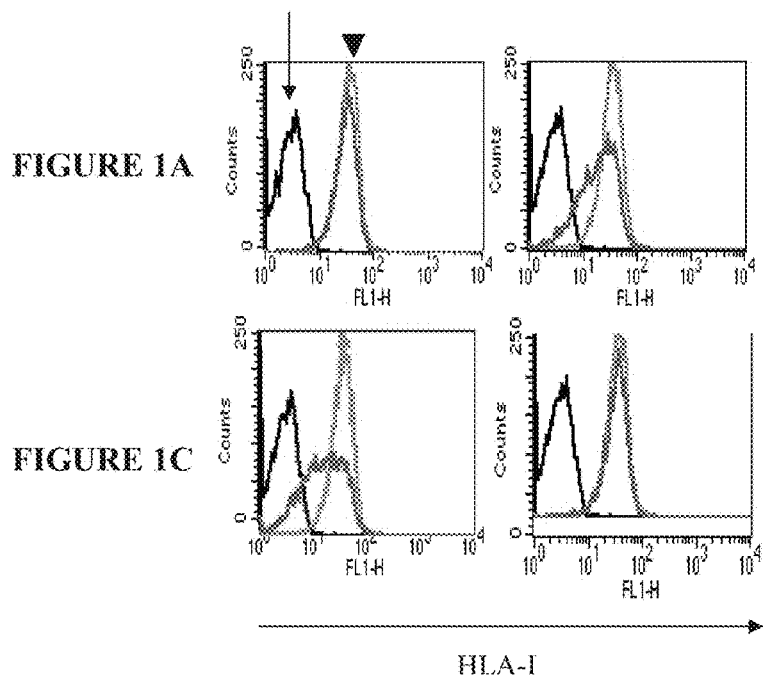
FIGURE 1A
FIGURE 1B
FIGURE 1C
FIGURE 1D
HLA-I
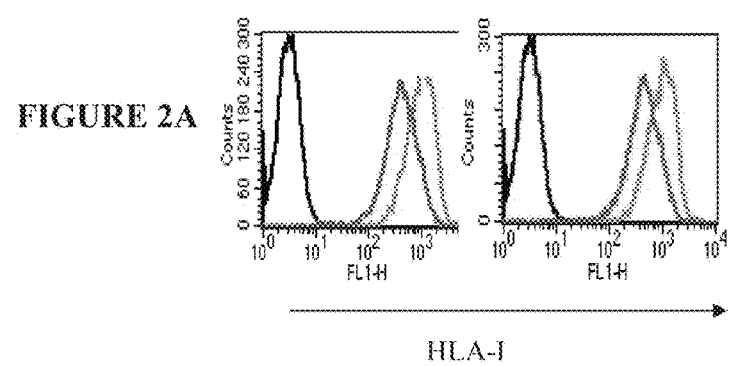
FIGURE 2A
FIGURE 2B
HLA-I
FIGURE 3A
| β2-Microglobulin | Spacer (Gly$_4$Ser)$_3$ | HLA-G1 |
FIGURE 3B
| CTLA4 extra-cellular Region Residues 1-126 | GPI signal sequence |

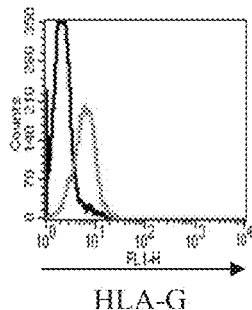 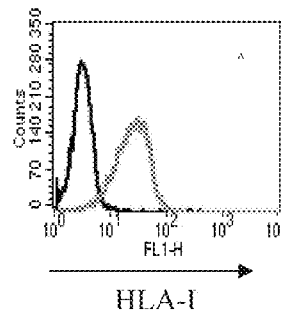 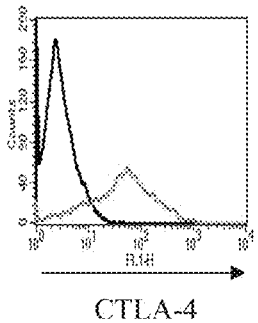
FIGURE 4A  FIGURE 4B  FIGURE 4C
HLA-G  HLA-I  CTLA-4
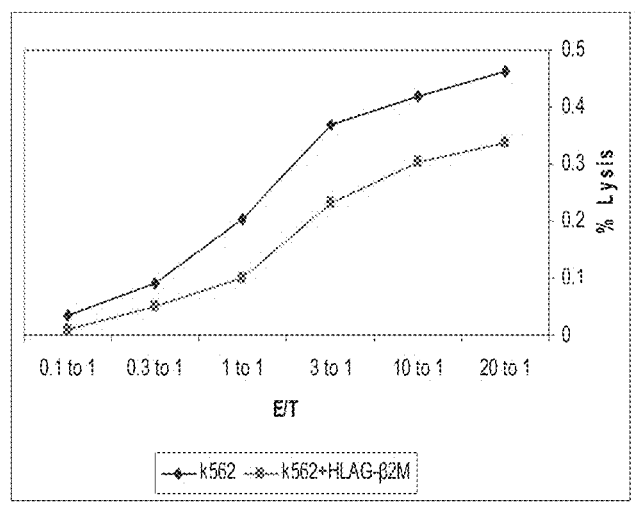
FIGURE 5A

100 RAD

200 RAD

200 RAD

Anti-HER2
Based on the N29 antibody

Anti-HER2

IMMUNOTHERAPY USING REDIRECTED ALLOGENEIC CELLS

BACKGROUND OF THE INVENTION

Field of the Invention

The subject matter of the application is in the field of biochemistry (immunology) and medicine and it relates to adoptive transfer therapy using tumor-specific allogeneic cells.

Background Description

Adoptive cell therapy (ACT) is a procedure in which therapeutic lymphocytes are administered to patients in order to treat either viral infection or cancer [1, 2]. This approach entails the ex vivo generation of tumor specific T cell lymphocytes and infusing them to patients. In addition to the lymphocyte infusion the host may be manipulated in other ways which support the take of the T cells and their immune response, for example, preconditioning the host (with radiation or chemotherapy) and administration of lymphocyte growth factors (such as IL-2) [1, 3, 4]. There are many methods for generating such tumor specific lymphocytes with the two main approaches being expansion of antigen specific T cells or redirection of T cells using genetic engineering [1, 5, 6]. The most notable success of ACT has been in the treatment of metastatic melanoma. In a landmark clinical trial, Dudley et al. lymphodepleted melanoma patients and then administered autologous tumor infiltrating lymphocytes expanded ex vivo, concurrently with IL-2 achieving objective responses in over 50% of the patients [7]. These results are superior to all other therapies targeting metastatic melanoma, and it is the only form of specific immunotherapy which has been proven to confer therapeutic benefit [1].

While the results observed in melanoma are very impressive, tumor infiltrating lymphocytes (TIL) can only be isolated from melanoma or renal cancer, and therefore they cannot be used a general strategy to treat cancer [1]. Gene modification has been used to redirect lymphocytes against tumors via the use of transgenic TCR chains or chimeric receptors [1, 5, 6]. The inventors' lab has pioneered the use of antibody based chimeric receptors (chimeric antigen receptor—CAR) as a means of redirecting T cells ('the T-body approach') against tumor antigens [8]. The T-body is a regular T cell which expresses a TCR and a chimeric receptor, and is capable of being activated by either receptor. The original chimeric receptor was composed of a scFv fragment fused to a gamma chain [9]. A 'second generation' tripartite chimeric receptor (TPCR) was used, and it includes an additional signaling moiety (e.g. CD28 or CD137 or their combination) and is capable of activating naïve T cells in a co-stimulation independent manner, demonstrating its superiority over the native TCR [8]. The validity of the T-body approach has been validated in numerous pre-clinical models, demonstrating activity against hematological malignancies and solid tumors (including ovarian, prostate, breast, renal, colon, neuroblastoma and others) [2, 5, 10]. There have been a few initial clinical trials employing CAR modified T cells which failed to provide significant therapeutic benefit, but these trials mainly utilized 'first-generation' CAR (which lack co-stimulatory motifs in the CR) and did not include prior lymphodepletion of patients [5, 10, 11]. In a recent landmark clinical trial, Pule et al. show that EBV CTL engineered with a GD2-specific chimeric receptor persist longer in vivo and provide some therapeutic benefit against neuroblastoma, demonstrating the potential of the 'T-body' approach [12].

Despite these successes ACT has one major drawback: each patient receives an individually fabricated treatment, using the patients' own lymphocytes, thus limiting the practicality of ACT due to substantial technical and logistic hurdles facing its application. Ideally, one would like to transform ACT into a standardized therapy in which off the shelf, ready for use 'universal' allogeneic therapeutic cells could be administered to patients. By allogeneic it is meant that the cells are obtained from individuals belonging to the same species but are genetically dissimilar. The problem with using allogeneic cells is double edged. In immune-competent hosts allogeneic cells are rapidly rejected, a process termed Host vs. Graft reaction (HvG) [13, 14]. In immune-incompetent hosts allogeneic cells can overcome the host's immune system, and cause serious damage and even death, a process termed Graft vs. Host disease (GvHD) [13, 14]. In order to affect adoptive therapy using allogeneic cells one would have to overcome these problems.

HvG reaction is mediated by T, B, and NK cells. T cells can either recognize allogeneic MHC molecules directly (major histocompatibility mismatch) or alternatively they can recognize non-self peptides (derived from foreign polymorphic proteins) in the context of self MHC molecules (indirect recognition stemming from minor histocompatibility mismatch) [13, 14]. B cells can recognize any foreign protein presented on the cell membrane (be they foreign MHC molecules or other polymorphic proteins) [1,5]. In addition B cells can also recognize foreign carbohydrate moieties, namely the ABO blood group antigens (as well as other blood group antigens) [1,6]. However blood group mismatch can be easily avoided, and does not usually present a problem. NK cells recognize allogeneic cells using a completely different strategy termed 'Missing Self' [17]. NK cells possess receptors capable of recognizing self MHC molecules such that in the presence of syngeneic cells NK cells are inhibited [17]. Importantly NK cells express these inhibitory receptors in a variegated fashion such that not all NK express all possible inhibitory receptors [17]. The result of this expression pattern is that some NK cells are capable of 'sensing' the absence of a single MHC molecule [17]. In this way T and NK cells complement each, and evading one cell type invites attack from the other.

The GvHD reaction only occurs when the host's HvG reaction is impaired usually in the context of allogeneic bone marrow transplantation, but also in some experimental conditions such as the parent to F1 transplantation model [13, 14]. Donor allo-reactive T cells migrate to lymphatic organs, proliferate extensively, and then egress and attack peripheral organs [14]. The potential to cause GvHD depends on two main factors: the ability to reach the lymphatic organs, and the potential for extensive proliferation [14, 18]. The ability to reach the lymph nodes is determined by expression of the lymph homing molecules CD62L and CCR7 [19]. These molecules are expressed by naïve T cells, and central memory T cells (Tcm), but not by effector memory T cells (Tem) [20-22]. Indeed studies have shown that Tcm produce much weaker GvHD than naïve or Tcm cells, and that blocking entry into lymphatic organs can prevent GvHD [23].

Due to the hurdles facing allogeneic adoptive therapy, allogeneic cells have only been employed in a handful of studies. Prior to the instant invention, the few studies which employed allogeneic ACT did so exclusively in the context of allogeneic bone marrow transplantation (allo-BMT). The preconditioning for allo-BMT ablates the host's immune system allowing engraftment of the donor bone marrow. In this setting, there is no HvG response against the original donor, and the main problem with this therapy is the development of GvHD (which can occur even if the host and donor are MHC matched) [13, 14]. The first successful application of allogeneic ACT was accomplished through the use of donor lymphocyte infusion (DLI) in the treatment of CML following allo-BMT [24-26]. The infused donor lymphocytes attack the tumor, and are capable of causing tumor regression [26]. Unfortunately because of the inherent GvH reactivity of the donor lymphocytes GvHD is a major problem with DLI [24-26]. Beginning with that initial trial, extensive work has been done to determine the optimal cell dose and conditioning regimen needed for optimal tumor response not just in CML, but also in other hematological malignancies [24, 25]. Despite these many repeated attempts. DLI has failed to show significant efficacy in other types of hematological malignancies (AML, ALL, CLL, etc) in clinical trials, so this approach does not constitute a general strategy to target tumors [24, 25]. Since then, there have been many attempts to replace the non-specific cells used in DLI with tumor specific cells. In attempt to replace DLI with tumor specific cells, Baker et al. developed a culturing protocol which yields cells with broad tumor recognition (based on NKG2D recognition), named cytokine induced cells (CIK) [27-29]. CIK cells are generated through extended culturing protocol involving extensive proliferation in the presence of IFN-γ [27-29]. These cells exhibit broad tumoricidal activity against numerous leukemias in an MHC independent manner, and importantly cause much less GvHD after allogeneic MHC mismatched BMT than fresh T cells [27-29]. The prolonged culture required in generating these cells reduced their proliferative capacity as compared with fresh splenocytes which explains at least partially the lower level of GvHD caused by these cells [28]. While these results are promising, this approach has only shown efficacy in treating hematological malignancies and little or no efficacy against solid tumors. Another drawback is that this approach and all other approaches published prior to the instant invention rely on prior allo-BMT. This dependence on allo-BMT is problematic for two reasons: first it requires complete or nearly complete MHC matching otherwise the result is overwhelming GvHD, second even if a suitable donor is found the preconditioning regimen is associated with considerable toxicity and morbidity limiting its use in some patients (such as elderly patients). In addition these treatments are only applicable when cells are obtained from the original donor which means each patient is individually treated negating the possibility of a standardized treatment.

Two papers were recently published which employed allogeneic ACT in conjunction with syngeneic BMT. In the first study, Boni et al. used haploidentical splenocytes from transgenic TCR mice to treat large established B16 melanomas after intense preconditioning in combination with autologous BMT [30]. The rationale behind this study was that myeloablation should completely prevent the HvG reaction allowing the allogeneic T cells to attack the tumor, but concurrently exposing the host to the risk of GvHD. In this case, the use of transgenic T cells which express a monoclonal TCR prevented development of acute GvHD, while infusion of open repertoire T cells did cause acute GvHD, demonstrating that a monoclonal TCR can posses little or no allo-reactivity [30]. Therapeutic benefit using allogeneic cells was only observed when the host was completely myeloablated with 9 gray, with little or no benefit at 5 gray, a fact that the authors explained by the relatively brief persistence of allogeneic cells after 5 gray irradiation (less than 10 days) [30]. Importantly, while 9 gray irradiation facilitated enhanced persistence by allogeneic cells, they nevertheless provided inferior benefit as compared with syngeneic cells which the authors attributed to the eventual rejection of the allogeneic cells by the host [30]. In addition, the use of haploidentical cells in this model, while very challenging, nevertheless, falls short of a fully mismatched model, which means that some matching between donor and host is still needed precluding using this approach as a standardized therapy.

In the second paper. Zakrezewski et al. (Marcel van den Brink's group in collaboration with Michel Sadelain) developed a completely novel approach which entails adding gene modified T-cell precursors to syngeneic BMT in a model of minimal residual B cell lymphoma [31]. Since the T-cell precursors mature in the host's thymus they undergo negative selection and lose GvH reactivity, but unfortunately maturation in the thymus also purges any GvL reactivity they possess [31]. Transduction with a anti-CD19 chimeric receptor redirects the maturing T cells against the residual lymphoma providing a significant but modest survival advantage with no long term survivors [31].

Allogeneic ACT has been proven to be successful when practiced following allogeneic bone marrow transplantation. Proper MHC matching can limit the occurrence of severe GvHD, but unfortunately also limits the applicability of allo-BMT. Without allogeneic bone marrow transplantation the host's immune system will eventually reject all of the transferred allogeneic cells, and the rate of rejection depends on the immune-competence of the host.

SUMMARY OF THE INVENTION

Adoptive cell therapy (ACT) of tumor-specific autologous T cells has emerged as a promising approach for the treatment of tumors, particularly in the treatment of metastatic melanoma in patients. A potential shortcoming in the wide application of this approach is that it necessitates the use of the patients' own cells. An aim of the present application was to find a way to enable safe and effective adoptive transfer therapy using tumor-specific allogeneic cells. The problem with adoptively transferring allogeneic cells is that either they will be rejected by the host (host vs. graft. HvG), or that the transferred cells will attack the host (graft vs. host, GvH). The use of tumor-specific, chimeric receptor redirected allogeneic T cells can transform ACT from an individually fabricated therapy into a standardized therapy.

Accordingly, an objective of the instant application is to enable safe and effective adoptive therapy using fully or partially mismatched allogeneic cells without resorting to BMT, thus transforming adoptive transfer from an individually fabricated therapy into standardized treatment.

To achieve this objective, the inventors first hypothesized that redirected allogeneic T cells will be functionally superior to redirected autologous cells or to non-redirected allogeneic cells. The inventors' second hypothesis was that 'stealthing' allogeneic cells could prolong their persistence in vivo. The inventors' third hypothesis was that combining different cell doses with various levels of host preconditioning could create a therapeutic time window which would allow allogeneic cells sufficient time to eradicate the tumor before being themselves rejected. Specifically, the inventors sought to test whether increasing the magnitude of the response, through increased cell dose or through increased preconditioning, could compensate for limited persistence due to the eventual rejection of the cells, thus circumventing the need for BMT. The inventors' fourth hypothesis was that delaying donor cells egression from lymph nodes (LN) after their adoptive transfer could prevent HvG and GvHD while boosting the antitumor response.

Accordingly, the invention relates to methods of treatment and/or prevention of disease, such as cancer, and pharmaceutical compositions for such treatment.

These and other features, aspects, and advantages of the invention will become better understood with regard to the following description, appended claims, and accompanying drawings as set forth below.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1A-1D: shRNA mediated silencing of HLA-I in 293 cells. 293 cells were transfected with shRNA plasmids specific for the β2M 3' UTR region (clones 172721, 221378, 218774 from Open biosystems) as well as a control plasmid. The transfected cells were stained with strepavidin-FITC alone (black line) or the anti-HLA-I W6/32 antibody-biotin+ strepavidin-FITC together (light gray line (the tallest curve in each of the graphs)). Strepavidin-FITC alone (↓) delineated the 0% expression of HLA, while Strepavidin-FITC together with W6/32-biotin delineated 100% expression of HLA (▼). shRNA transfectants are the gray lines. Only clones 172721 and 221378 cause down regulation of HLA. FIG. 1A—non-silencing shRNA. FIG. 1B—shRNA clone 172721. FIG. 1C—shRNA clone 221378. FIG. 1D—shRNA clone 218774.

FIGS. 2A-2B: Down regulation of HLA molecules in JY cells. JY cells were infected with retrovectors containing shRNA for β2M 3' UTR region (same as in FIG. 1). JY cells were then stained with strepavidin-FITC alone (black line) or the anti-HLA-I W6/32 antibody-biotin+strepavidin-FITC together (light gray line). Strepavidin-FITC alone delineated the 0% expression of HLA, while Strepavidin-FITC together with W6/32-biotin delineated 100% expression of HLA. shRNA transfectants (gray lines) show modest down regulation. FIG. 2A—shRNA clone 172721. FIG. 2B—shRNA clone 221378.

FIGS. 3A-3B: Schematic representation of fusion proteins. FIG. 3A—The coding region of β2M without the 3' UTR is fused to HLAG through a spacer. FIG. 3B—The extracellular region of CTLA4 is directly fused to a GPI signal sequence.

FIGS. 4A-4C: Fusion proteins are expressed at the cell surface. FIG. 4A—Staining of K562 (black) and K562 transfected with β2M-HLAG (light gray) with FITC-aHLAG Mem-G/9 antibody. FIG. 4B—Staining of K562 (black), and K562 transfected with β2M-HLAG (light gray) with FITC-aHLA-I W6/32 antibody. FIG. 4C—Staining of K562 (black), and K562 transfected with CTLA4$_{Extracellular}$-GPI (light gray) with FITC-CTLA4 BNI3 antibody.

FIGS. 5A-5F: Fusion proteins slightly inhibit NK killing. Inhibition of NK by HLAG-β2M and CTLA4$_{Extracellular}$-GPI was measured in 4 hour $^{51}$Cr release assays. FIG. 5A—HLAG-2M (-■-) slightly inhibits lysis of K562 (-♦- (darker line)) by NK92. FIG. 5B—HLAG-β2M (-■-) slightly inhibits lysis of 721 (-♦-) by NK92. FIG. 5C—HLAG-β2M (-■-) doesn't inhibit lysis of 721 (-♦-) by YTS. FIG. 5D—CTLA4$_{Extracellular}$-GPI (-■-) slightly inhibits lysis of K562 (-♦-) by NK92. FIG. 5E—CTLA4$_{Extracellular}$-GPI (-■-) increases lysis of K562 (-♦-) by YTS. FIG. 5F—HLAG-β2M (-■-) slightly inhibits lysis of K562 (-♦-) by freshly isolated primary NK.

FIG. 6A—Total of 25, 50, or 100 million T cells transferred after irradiation with 100 rads. No GVHD. FIG. 6B—Total of 25, 50, or 100 million T cells transferred after irradiation with 200 rads. No GVHD. FIG. 6C—Total of 30, 50, or 100 million T cells transferred after irradiation with 400 rads. GVHD at all doses except for 30 million. FIG. 6D—Total of 25, 50, or 100 million T cells transferred after irradiation with 200 rads. Mice were monitored for weight loss. There was only weight loss after transfer of 100 million T cells.

FIG. 7A—Chimeric receptor transgene constructs. Constructs used to generate the transgenic mice were placed under the control of the human CD2 promoter/enhancer that directs expression only in T and NK cells. CYT indicates cytoplasmic domain: H, hinge domain; L, immunoglobulin leader; LCR, locus control region; P, promoter; pL, plasmid sequence; TM, transmembrane domain; $V_H$ and $V_L$, immunoglobulin heavy and light-chain variable domains, respectively. FIG. 7B.—Schematic presentation of the HER2-specific chimeric receptors. The HER2-specific CR encompasses a scFv derived from the anti-HER2 mAb, N29. In the tripartite configuration, the scFv is joined in tandem to a short portion of CD28 (lacking the ligand-binding site) of the extracellular and including the transmembrane, and cytoplasmic domains fused to the FcRγ ITAM domain. FIG. 7C—Experimental scheme of the treatment. FIG. 7D—Renca is resistant to irradiation. Survival curves of unirradiated Renca-erbb2 bearing mice, and mice irradiated with 200 and 400 rads on day 7 after tumor inoculation—no differences were observed (n=6). FIG. 7E—Lung histology of tumor bearing mice on day 8, one day after irradiation with 200 rads.

FIG. 8A—Renca-erbb2-Luciferase cells were co-incubated with activated allogeneic T-bodies (Black-N29) or allogeneic T cells (Black) at the indicated effector to target ratios in 24 well plates. After 24 hours Luciferase emission was measured from the plate. % Killing was measured as=100−(Luciferase signal from killing well)/(Luciferase signal from control well). FIG. 8B—Renca-erbb2-Lucifcrase cells were co-incubated with activated allogeneic T-bodies (Black-N29) or allogeneic T cells (Black) in 96 flat well plates. After 24 hours $H^3$ thymidine was added to the wells, and thymidine incorporation was measured at 48 hours.

Results represent one experiment out of two. FIG. 10A—Irradiation dose: 200 rads. T cell dose: $10^8$ million divided to 2 equal doses on days 8 and 10. Medians for C57Bl-N29, C57Bl, and control groups are: 155, 70, and 43 days respectively. C57Bl-N29 is superior to wild type C57Bl (P<0.004) which is superior to control group (P<0.0015). FIG. 10B—Irradiation dose: 400 rads. T cell dose: 30 million divided to 3 equal doses on days 8, 10, and 12. Medians for, C57Bl-N29, C57Bl, and control groups are: 110, 24, and 50 days respectively. C57Bl-N29 significantly extend survival as compared to the C57/Bl and control groups (P<0.002).

FIG. 11A—Irradiation dose: 200 rads. T cell dose: $10^8$ million divided to 2 equal doses on days 8 and 10. Medians for Balb-N29, C57Bl-N29, and control groups are: 165, 155, and 43 days, respectively. Balb-N29 and C57Bl-N29 prolong survival to a similar extent (P=0.68) and both are superior to the control group (P<0.0015). FIG. 11B—Irradiation dose: 400 rads. T cell dose: 30 million divided to 3 equal doses on days 8, 10, and 12. Medians for Balb-N29, C57Bl-N29, and control groups are: 90, 110, and 50 days, respectively. C57Bl-N29 extend survival slightly more than Balb-N29 (but it does not reach statistical significance), and both are better than the control group (P<0.002). FIG. 11C—Comparison of the two regimens using C57Bl-N29 cells (Irradiation with 200 rads and transfer of 100 million cells vs. irradiation with 400 rads and transfer of 30 million cells). The medians for the 200/100, 400/30 regimens, and the control group were 150, 110, and 50 days respectively. The 200/100 regimen prolong survival to a greater extent than the 400/30 regimen, but the results don't quite reach statistical significance.

FIG. 12A—Transduction efficiency of C57Bl with the N29 chimeric receptor as assessed by the GFP reporter on the same plasmid. FIG. 12B—Transduction efficiency of Balb/c with the N29 chimeric receptor as assessed by the GFP reporter on the same plasmid. FIG. 12C—Comparison between untreated (50 days), mock transduced C57Bl allogeneic T cells (71 days), transduced C57Bl-N29 (median not reached), and transduced Balb-N29 (106 days). Medians for the group are indicated in parentheses. FIG. 12D—Comparison between transduced C57Bl-N29, transgenic C57Bl-N29+wildtype C57Bl, transduced Balb-N29, transgenic Balb-N29+wildtype Balb. The transgenic cell dose was adjusted so that exactly the same number of T-bodies will be injected regardless whether they were of transgenic or transduced origin. Wildtype activated splenocytes (either C57Bl or Balb/c) were added to the transgenic splenocytes, such that the total number would equal the transduced cell dose (100 million cells).

FIG. 13A—Comparison between untreated (71 days), mock transduced C57Bl allogeneic T cells (100 days), transduced C57Bl-N29 (median not reached), and transduced Balb-N29 (120.5 days). Medians for the group are indicated in parentheses. FIG. 13B—Comparison between transduced C57Bl-N29, transgenic C57Bl-N29+wildtype C57Bl, transduced Balb-N29, transgenic Balb-N29+wildtype Balb. The transgenic cell dose was adjusted so that exactly the same number of T-bodies will be injected regardless whether they were of transgenic or transduced origin. Wildtype activated splenocytes (either of C57Bl or Balb/c origin) were added to the transgenic splenocytes, such that the total number would equal the transduced cell dose (20 million cells injected pr mice total).

FIG. 14A—Lung on day 4 showing normal histology. FIG. 14B—Liver on day 4 showing normal histology. FIG. 14C—Intestine on day 4 showing normal histology. FIG. 14D—Kidney on day 4 showing normal histology. FIG. 14E—Lung on day 6 showing normal histology with minor lymphocytic infiltration (L). FIG. 14F—Liver on day 6 showing normal histology with minor lymphocytic infiltration (L). FIG. 14G—Intestine day 6 showing normal histology with minor lymphocytic infiltration (L). FIG. 14H—Kidney on day 6 showing normal histology.

FIG. 17A—Image taken of the whole mouse. FIG. 17B—Image taken of mouse's organs. FIG. 17C—PE-Cy7-CD62L and FITC-CD44 were used to stain splenocytes which were activated for 48 hours with CD3/CD28, and then cultured in 200 u/ml IL-2 for 5 days.

FIG. 18A—Mice were irradiated with 400 rads and then were either left untreated or injected with $10^7$ T cells on days 8, 10, and 12 each ($30*10^6$ total). T cells were from either C57Bl, C57Bl-N29, Balb-N29 origin. Each treatment was done either alone or with FTY720. FIG. 18B—Mice were irradiated with 200 rads and then were either left untreated or injected with $50*10^6$ T cells on days 8, and 10 ($10^8$ total). T cells were from C57Bl, C57Bl-N29, or Balb-N29. Each treatment was done either alone or with FTY720.

FIG. 19A—Balb/c (n=6) were inoculated with $10^5$ Renca-erbb2 cells IV on day 1, irradiated with 200 rads on day 7, and injected with $50*10^6$ Luciferase expressing T-bodies (either syngeneic Balb-N29 or allogeneic Black-N29) on days 8, and 10. FIG. 19B—Balb/c (n=6) were inoculated with $10^5$ Renca-erbb2 cells IV on day 1, irradiated with 400 rads on day 7, and injected with $15*10^6$ Luciferase expressing T-bodies (either syngeneic Balb-N29 or allogeneic Black-N29) on days 8, and 10. FIG. 19C—Total bioluminescence was measured from the entire mouse from each of the group. The graph shows the average total flux (as well as standard deviation) from the mice in each group FIG. 20A—Balb/c (n=6) were inoculated with $10^5$ Renca-erbb2 cells IV on day 1, irradiated with 400 rads on day 7, and injected with $15*10^6$ Luciferase expressing Black-N29 T-bodies on days 8, and 10. In one of the group 0.3 mg/kg FTY720 was injected ip daily on days 8-18. FIG. 20B—Total bioluminescence was measured from the entire mouse from each of the group. The graph shows the average total flux (as well as standard deviation) from the mice in each group.

(FIG. 22a) Protocol consisted of 200 rad irradiation and $30 \times 10^6$ T-bodies (200 R/30). Balb-N29 or Black-N29 vs. control P=0.000004. (FIG. 22b) Protocol consisted of 200 rad irradiation and $100 \times 10^6$ T-bodies (200 R/100). Balb-N29 or Black-N29 vs. control P=0.000004. (FIG. 22c) Protocol consisted of 400 rad irradiation and $30 \times 10^6$ T-bodies (400 R/30). Balb-N29 or Black-N29 vs. control P=0.000004. (FIG. 22d) Protocol consisted of 400 rad irradiation and $100 \times 10^6$ T-bodies (400 R/100). Balb-N29 vs. control P=0.000004. The Black-N29 group died from GvHD manifested by severe cachexia and lymphoid hypoplasia—data not shown.

(FIG. 24a) Comparative in vivo bioluminescence imaging of Renca-Her2/neu-bearing mice (n=6/group) treated with either syngeneic (Balb-N29) or allogeneic (Black-N29) T-bodies according to different protocols, as indicated. Bioluminescence imaging (BLI) was performed using two animals per acquisition to avoid interference of strong photon sources with areas in close proximity. Images shown are of three representative mice per group. 200 R/30=Irradiation with 200 rads and $30 \times 10^6$ T-bodies. 200 R/100=Irradiation with 200 rads and $100 \times 10^6$ T-bodies. 400 R/30=Irradiation with 400 rads and $30 \times 10^6$ T-bodies. (FIG. 24b) Whole body BLI signal intensities from sequential imaging every 3-4 days after T cell transfer for a 20-day period. Each line represents a single animal. Pairwise differences between groups were analyzed using the Mann-Whitney test. P=−0.005 for Black-N29 vs. Balb-N29 using 200 R/100 protocol on day 1. P=0.005 for Black-N29 vs. Balb-N29 using 400 R/30 protocol on day 7. P=0.002 for Black-N29 vs. Balb-N29 using 400 R/30 protocol on day 14. (FIG. 24c) CFSE-labeled T-bodies were transferred to tumor-bearing mice according to the protocols described above. Mice were sacrificed 4 days after transfer, and splenocytes were harvested. Splenocytes were stained with an anti-idiotypic antibody to identify donors T-bodies (not shown), and CFSE staining is shown for the transferred T-bodies. (FIG. 24d) Splenocytes from mice treated with allogeneic T-bodies using the 400 R/30 protocol were gated on $CD3^+$ cells, and analyzed for expression of CFSE vs. CD62L. The data show progressive differentiation (loss of CD62L) concomitant with proliferation (loss of CFSE), P=0.0001 using the chi-square test.

(FIG. 25a) Kaplan-Meyer survival plots of Renca-Her2/Neu-bearing mice. Mice (n=12/group) were irradiated with 400 rads, and 1 day later either left untreated as a control (diamond), or injected with $30 \times 10^6$ transgenic T-bodies. Some groups received FTY720 0.3 mg/kg ip for 10 days following transfer. T cells were either: syngeneic T-bodies (Balb-N29, squares), syngeneic T-bodies with FTY720 (Balb-N29, gray squares—shown in the lower right), allogeneic T-bodies (Black-N29, brown triangles—shown in the lower right), allogeneic T-bodies with FTY720 (Black-N29, olive triangles—shown in the upper right, Black-N29+FTY720 vs. Black-N29, P=0.013). P-values were computed separately for each experiment using the log-rank test and combined using Fisher's method. (FIG. 25b) Comparative in vivo BLI of Renca-Her2/neu-bearing mice (n=6/group) irradiated with 400 rads, and treated with either 30×10$^6$ syngeneic (Balb-N29) or allogeneic (Black-N29) T-bodies. BLI was performed as in FIG. 24a. (FIG. 25c) Whole body BLI signal intensities from sequential imaging every 3-4 days after T cell transfer for a 20-day period. Each line represents one animal. (FIG. 25d) A region of interest was defined around the spleens of mice from FIG. 25b. Shown are absolute photon counts from mice treated with allogeneic T-bodies either with or without FTY720. Means and SEM are shown. (FIG. 25e) Mononuclear cells were isolated 4 days after adoptive transfer from the blood of tumor-bearing mice treated with allogeneic T-bodies either with or without FTY720, and the number of T cells in the blood was quantified by staining for CD3. Means and SEM are shown. (FIG. 25f) Splenocytes of tumor-bearing mice treated with allogeneic T-bodies either with or without FTY720, were stained 4 days after adoptive transfer with anti-H2K$^b$ in order to identify the allogeneic T-bodies. Means and SEM are shown. (FIG. 25g) Splenocytes of tumor-bearing mice treated with allogeneic T-bodies either with or without FTY720, were stained 7 days after adoptive transfer with anti-H2K$^b$ in order to identify the allogeneic T-bodies. Means and SEM are shown. (FIG. 25h) Kaplan-Meyer survival plots of Renca-Her2/Neu-bearing mice. Mice (n=6/group) were irradiated with 400 rads, and 1 day later either left untreated as a control (diamond), or injected with 100×10$^6$ allogeneic T-bodies either with (triangles shown on the left) or without FTY720 (triangles shown on the right).

DETAILED DESCRIPTION OF THE INVENTION

Figure 5B:
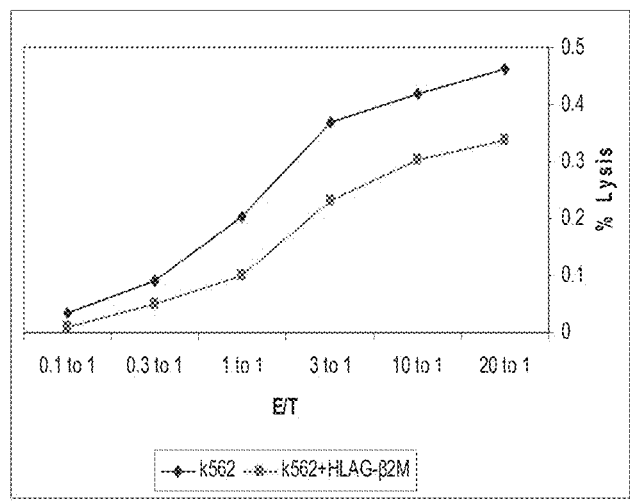
Figure 5C:
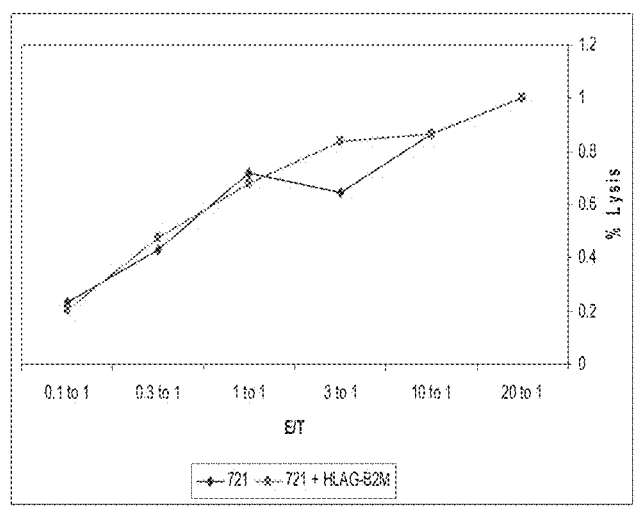
Figure 5D:
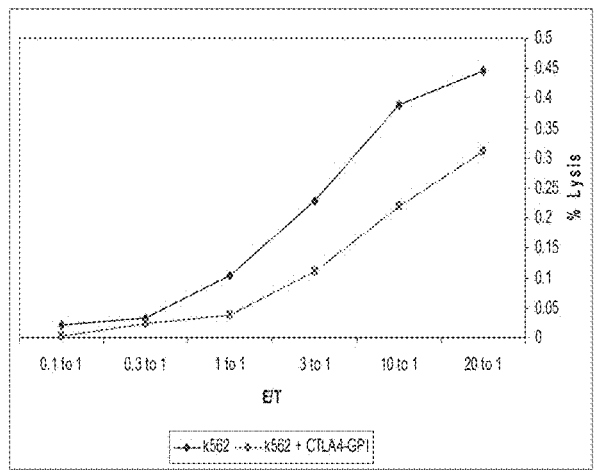
Figure 5E:
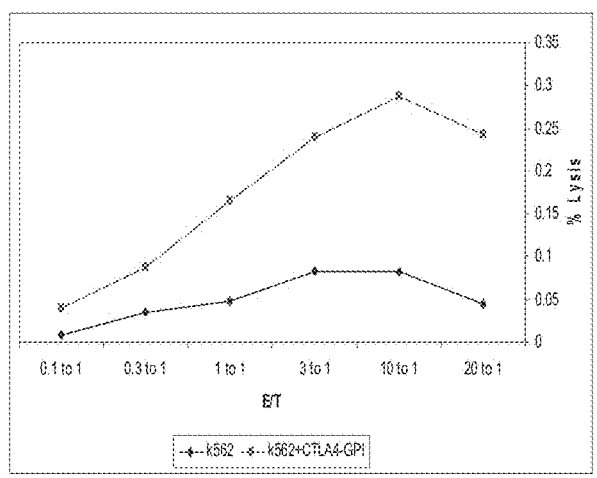
Figure 5F:
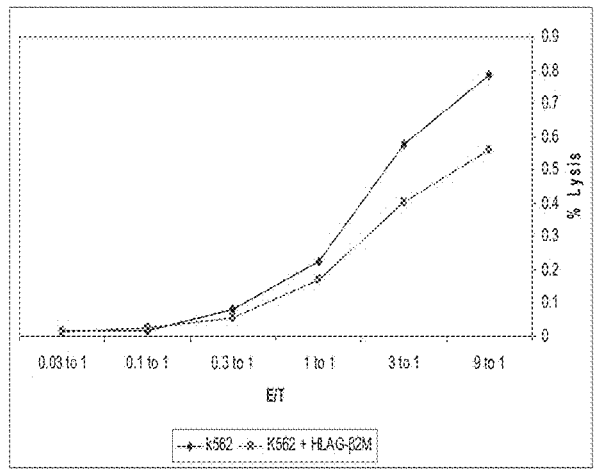

Some common abbreviations used throughout are as follows:
ACT: Adoptive Cell Therapy
FCS: Fetal Bovine Serum
DMEM: Dubbelco's modified eagle's medium
PBS: Phosphate buffered solution
GFP: Green Fluorescent Protein
ShRNA: Short Hairpin RNA
UTR: Untranslated Region
i.v.: intravenous
i.p.: intraperitoneal
scFv: single chain variable fragment
CR: Chimeric Receptor
CAR: Chimeric Antigen Receptor
TPCR: Tri-partite Chimeric Receptor
BMT: Bone Marrow Transplantation
Allo-BMT: Allogeneic BMT
Auto-BMT: Autologous or syngeneic BMT
HvG: Host vs. Graft
GvH(D): Graft vs. Host (Disease)
GvL: Graft vs. Leukemia
MHC: Major Histocompatibility Complex
APC: Antigen Presenting Cell
NK: Natural Killer
CML: Chronic Myeloid Leukemia
DLI: Donor Lymphocyte Infusion
CIK: Cytokine Induced Killer
TBI: Total Body Irradiation
CTL: Cytotoxic T Lymphocyte
TIL: Tumor Infiltrating Lymphocyte
Tcm: Central Memory T cell
Tem: Effector Memory T cell
Tscm: T Memory Stem cell
WT: Wild Type
LN: Lymph Node By way of the instant of the application, the inventors have developed safe and effective allogeneic adoptive therapy for the treatment of cancer. The present invention provides a proof of concept for allogeneic adoptive therapy with a good safety profile which is as effective as syngeneic adoptive therapy, while avoiding the use of BMT by:

(1) "Stealthing" T effector cells by down regulating class I and II using shRNA, while concurrently preventing NK mediated killing by expression of an NK inhibitory ligand.

(2) Finding the most powerful adoptive transfer regimens which do not induce GvHD and avoid BMT.

(3) Comparing the therapeutic benefit of chimeric receptor redirected transgenic (CR-Tg) allogeneic cells as opposed to CR-Tg syngeneic cells, and unmodified allogeneic cells.

(4) Demonstrating safety of allogeneic adoptive therapy.

(5) Studying the dynamics of the allogeneic T-body response including the homing patterns and in vivo persistence of adoptively transferred cells.

(6) Studying how the addition of FTY720 modulates the Graft vs Host response and the antitumor response.

To achieve their objective, the inventors investigated whether "stealthing" allogeneic cells could prolong their persistence in vivo and reduce the rejection of the allogeneic cells (i.e., the above-noted second hypothesis). "Stealthing" was achieved by silencing the expression of MHC molecules (using shRNA) and concurrently expressing an inhibitory ligand for NK cells in transferred cells. MHC silencing can prevent recognition and elimination of the allogeneic cells by T cells, but at the same time make them susceptible to NK attack ('missing self') which is why an additional inhibitory ligand is needed. Although somewhat successful, the "stealthing" approach, by itself, did not sufficiently protect the cells from allogeneic attack; therefore an alternative strategy was developed, as discussed below. However, "stealthing" is an option which may augment the efficacy of the antitumor response by reducing HvGD, when used in combination with one or more of the alternative strategies discussed below.

Second, the inventors combined different cell doses with various levels of host preconditioning to create a therapeutic time window in which to delay the rejection of allogeneic cells (i.e., the above-noted third hypothesis). Specifically, the inventors tested whether increasing the magnitude of the response, through increased cell dose, could compensate for shorter persistence due to reduced host preconditioning, thus circumventing the need for BMT.

In this approach, the inventors manipulated the host to allow "unstealthed" allogeneic tumor-specific T cells expressing antibody based chimeric receptors (T-bodies) to execute their antitumor function. One straightforward path to enhance persistence of allogeneic cells is to lymphodeplete the host using either radiation, or chemotherapy (a strategy also used in syngeneic adoptive therapy to overcome homeostatic control and create a niche to the grafted cells). Lymphodepletion impairs the host's immune system, thus delaying the rejection of allogeneic cells, in effect creating a therapeutic time window in which allogeneic cells can act. The problem with ablating the host's immune system is the increased risk of GvHD associated with immune incompetence. In this application, the inventors show that under certain regimens of allogeneic adoptive therapy, HER2-specific T-bodies (T cells which are redirected through an HER2-specific chimeric receptor) can significantly extend survival and even cure some mice, in a murine model of HER2$^+$ renal cancer pulmonary micrometastases (simulating the clinically relevant minimal residual disease setting). Allogeneic T-bodies provide comparable therapeutic benefit to syngeneic T-bodies, and are far superior to non-specific allogeneic T cells. Importantly the allogeneic therapy was safe, with no mortality, and only transient weight loss (of up to 10%). Histologic analysis revealed peripheral tissues sustained little or no damage despite sporadic lymphocytic infiltration.

In another approach, the inventors established a way to delay donor cells egression from lymph nodes after their adoptive transfer to prevent GvHD without impairing the antitumor response (i.e., the above-noted fourth hypothesis). In an attempt to improve allogeneic therapy, under this approach, the inventors explored the use of an inhibitor of lymphocyte egress, e.g., FTY720, a substance known to trap lymphocytes in the lymph nodes. It was surmised that temporary application of FTY720 could blunt the GvHD response, and that amelioration of the GvHD response could enable the use of more powerful adoptive transfer protocols, ultimately allowing for improved efficacy. Indeed, incorporation of FTY720 into the treatment protocol concurrently inhibited GvHD and yielded the best therapeutic results of all the protocols tested. In vivo imaging shows that prevention of lymphocyte egress through administration of a compound such as FTY720 does indeed prolong the in vivo survival of allogeneic T-bodies. Importantly, using this regimen, allogeneic cells showed superior therapeutic efficacy over syngeneic cells, demonstrating that allogeneic adoptive therapy can be an attractive alternative to syngeneic adoptive therapy, not just because of the obvious logistic benefits, but also because it can be more effective. As such, administration of FTY720 (or any other inhibitor of lymphocyte egress) can augment the antitumor response. Furthermore, the inventors have found that FTY720 traps both the host's lymphocytes and the allogeneic lymphocytes that were transferred ("transplanted") into the host. While the inventors believe that trapping the allogeneic lymphocytes with the host's lymphocytes may cause the allogeneic lymphocytes to attack the trapped host lymphocytes, thereby delaying their own rejection by HvG, this is just a theory. The inventors, however, do not wish to be bound to any particular theory. The inhibitor of lymphocyte egress is administered so as to be concomitant with the period of activity of the allogeneic chimeric T cells.

Accordingly, the invention of the present application relates to methods of treatment and/or prevention of disease, such as cancer, and pharmaceutical compositions for such treatment.

One embodiment of the invention provides for a method of treating a disease, such as cancer, comprising administering to a subject in need of such treatment an effective amount of allogeneic T cells, such as allogeneic T cells with a MHC unrestricted chimeric receptor. The combination of allogeneic T cells with a MHC unrestricted chimeric receptor yields "universal effector cells" for use a standard therapy of cancer. In this regard, T-bodies can be used as 'universal effector cells' because the CR is MHC unrestricted; in contrast, T cells (even TCR transduced T cells) are MHC restricted and therefore are not universal.

In another embodiment, the allogeneic T cells are chimeric receptor redirected allogeneic T cells. In this regard, the T-cells should express a chimeric receptor. The T-cells may be any T cell with a chimeric receptor that includes a tumor-specific single chain Ab, or other tumor-specific ligand, as part of its extracellular domain. Examples of such known cells expressing chimeric receptors and the chimeric DNA are disclosed in WO1993/019163 to Eshhar et al. and U.S. Pat. No. 6,407,221 to Capon et al., the entirety of which are hereby incorporated by reference herein. For instance, WO 1993/019163 discloses that by fusing a single-chain Fv domain (scFv) gene of a specific antibody, composed of $V_L$ linked to $V_H$ by a flexible linker, with a gene segment encoding a short extracellular and the entire transmembrane and cytoplasmic domains of a lymphocyte-activation molecule, a chimeric gene is obtained which combines the antibody recognition site and the lymphocyte-signaling moiety into one continuous chain. Upon transfection of such chimeric scFv-receptor (c-scFvR) gene into lymphocytes, it is expressed in the cell as a functional receptor and endows the cells with antibody-type specificity. Chimeric genes suitable to endow lymphocyte cells with antibody-type specificity are disclosed in WO1993/019163. Various types of lymphocytes are suitable, for example, natural killer cells, helper T cells, suppressor T cells, cytotoxic T cells, lymphokine activated cells, subtypes thereof and any other cell type which can express chimeric receptor chain. The chimeric gene comprises a first gene segment encoding the scFv of a specific antibody, i.e. DNA sequences encoding the variable regions of the heavy and light chains ($V_H$ and $V_L$, respectively) of the specific antibody, linked by a flexible linker, and a second gene segment which comprises a DNA sequence encoding partially or entirely the transmembrane and cytoplasmic, and optionally the extracellular, domains of a lymphocyte-triggering molecule corresponding to a lymphocyte receptor or part thereof. Further, as discussed in the above "Background" section, methods are known for redirecting primary T cells harboring a chimeric receptor (TPCR), including an additional signaling moiety (e.g., CD28 or CD137 or their combination), that is capable of activating naïve T cells in a costimulation independent manner [8]. While the use of a scFv as the extracellular domain of the chimeric receptor is preferred, any tumor specific ligand can be used for this purpose. The tumor-specific scFv, or other ligand, that is part of the chimeric receptor transduced into the T cells must be selected so as to be directed toward the specific kind of tumor in the patient being treated. For example, HER2 is a breast cancer marker. The N29 antibody is an anti-HER2 antibody. Thus, when the tumor being treated is breast cancer displaying HER2, in a preferred embodiment of the present invention, the allogeneic T cells can be transduced with a vector to express the chimeric N29 receptor after activation. See again, the disclosure in WO1993/019163 to Eshhar et al. the entirety of which is hereby incorporated by reference herein.

Another embodiment of the invention involves a combination therapy comprising one or more of the approaches described herein. For instance, the method may involve administering an effective amount of allogeneic T cells with a MHC unrestricted chimeric receptor, and one or more inhibitors of lymphocyte egress to delay egression of the allogeneic T cells from lymph nodes of the patient after adoptive transfer of the allogeneic T cells to the subject by trapping the T cells in the lymph nodes. This embodiment provides for trapping donor lymphocytes in lymphatic organs to prevent GVHD by administering one or more inhibitors of lymphocyte egress, prior to the administering step. An example of an inhibitor of lymphocyte egress is FTY720. FTY720 prevents lymphocyte egress by binding to S1P receptor (S1P1 in lymphocytes), which regulates lymphocyte egress from lymph nodes. Examples of other known compounds that accomplish this include: SEW2871, W123, and KRP-203 phosphate. Those of ordinary skill in the art could readily find and use similar or related compounds that have the desired function of inhibiting lymphocyte egress and the use of any such compound is considered to be a part of the present invention. Again, the use of an inhibitor of lymphocyte egress can augment the antitumor response, and thus it may be used in combination with one or more of the other approaches described herein.

FTY720, also known as Fingolimod, is an immune modulator. It is derived from the Myriocin (ISP-1) metabolite of the fungus *Isaria sinclairii*. It is a structural analogue of sphingosine and gets phosphorylated by sphingosine kinases in the cell (most importantly sphingosine kinase 2). The molecular biology of phospho-fingolimod is thought to lie in its activity at one of the five sphingosine-1-phosphate receptors, S1PR1. It can sequester lymphocytes in lymph nodes, preventing them from moving to the central nervous system for autoimmune responses in multiple sclerosis and was originally proposed as a anti-rejection medication indicated post-transplantation. The use of FTY720 as an immunosuppressive drug is disclosed in U.S. Pat. No. 7,605,171 to Colandrea et al., which is herein incorporated by reference in its entirety. The systematic IUPAC name for FTY720 is 2-amino-2-[2-(4-octylphenyl)ethyl]propane-1,3-diol (MW: 307.470820 g/mol|MF: $C_{19}H_{33}NO_2$) and it has the general formula shown below (for Fingolimod hydrochloride).

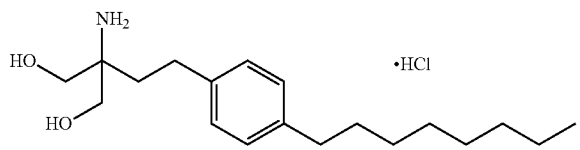

SEW2871 is another example of an inhibitor of lymphocyte egress. It is a potent and selective sphingosine-1-phosphate 1 ($S1P_1$) receptor agonist. It activates $S1P_1$ receptor with an $EC_{50}$ of 13 nM, but does not activate $S1P_2$, $S1P_3$, $S1P_4$ or $S1P_5$ receptors at concentrations up to 10 μM. It is cell-permeable and active in vivo. Its chemical name is 5-[4-Phenyl-5-(trifluoromethyl)thiophen-2-yl]-3-[3-(trifluoromethyl)phenyl]1,2,4-oxadiazole, and it has the general formula shown below.

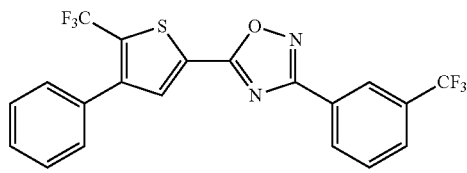

It should be noted that sphingosine-1-phosphate receptor 1 ($S1P_1$) is one of five high affinity G protein-coupled S1P receptors which mediate a variety of effects including lymphocyte recirculation in the blood. Non-selective S1P receptor agonists, such as FTY720, produce clinical immunosuppression useful for preventing transplant rejection and treating autoimmune diseases. However, they also cause bradycardia by activating $S1P_3$, the receptor responsible for regulation of heart rate. SEW2871 is a selective $S1P_1$ receptor agonist in both human and mouse that is not active at the $S1P_{2-5}$ receptors. SEW2871, therefore, suppresses the immune response by decreasing the number of lymphocytes circulating in blood without causing bradycardia.

W123 is another is another example of an inhibitor of lymphocyte egress. W123 is an analog of FTY720 that is a competitive antagonist of $S1P_1$. Its chemical name is 3-(2-(-hexylphenylamino)-2-oxoethylamino)propanoic acid and it has the general formula shown below.

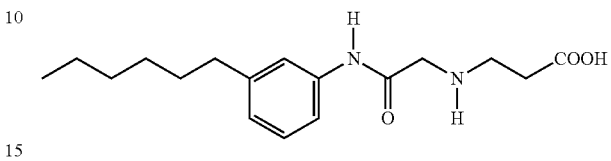

KRP-203 phosphate is another example of an inhibitor of lymphocyte egress. KRP-203 is a S1P receptor agonist that can alter lymphocyte homing and act as an immunomodulating agent. KRP-203 is a selective $S1P_1$ receptor agonist that acts as an immunosuppressant. KRP 203 is rapidly phosphorylated in vivo, indicating that KRP 203 acts as a prodrug for the actual $S1P_1$ agonist, KRP 203-phosphate. Like KRP 203, KRP203-phosphate is a selective $S1P_1$ receptor agonist, demonstrating a high affinity for $S1P_1$ ($ED_{50}$ value in the nM range) but not $S1P_3$ ($ED_{50}$>1 μM). Thus, the immunosuppressive effects of KRP 203 are comparable to FTY720 (a non-selective S1P receptor agonist), while the incidence of bradycardia is reduced 10-fold with KRP 203-phosphate compared to FTY720. When combined with low dose cyclosporine A, KRP 203-phosphate prolongs allograft survival and improves graft function. Its chemical name is 2-ammonio-4-(2-chloro-4-(3-phenoxyphenylthio) phenyl)-2-(hydroxymethyl)butyl hydrogen phosphate and it has the general formula shown below.

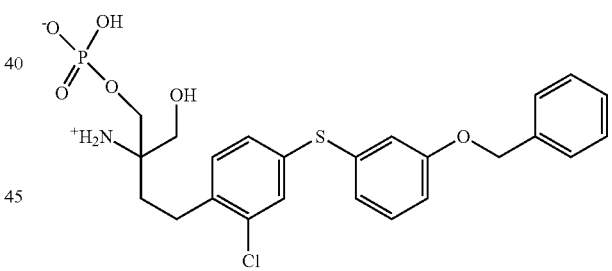

In another embodiment of a combination therapy, the method of the invention further comprises the "stealthing" approach of inhibiting recognition and elimination of the allogeneic T cells in vivo by T cells to thereby reduce the rejection of the allogeneic cells. In this approach, the inhibiting step comprises silencing MHC expression by administering an agent that knocks-out MHC expression, such as shRNA, or using allogeneic cells of humans harboring mutations that affect the expression of MHC molecules and expressing an inhibitory ligand for NK cells in the allogeneic T cells. Antisense RNA may also be used, as can be used any other known technique to silence MHC expression.

In another embodiment, the treatment method further comprises subjecting the patient to a lymphodepleting precondition step before the administering step. The lymphodepletion impairs the host's immune system to delay the rejection of allogeneic cells and to thereby provide time for the transferred allogeneic cells to act. The lymphodepleting treatment of the present invention can be one selected from the group consisting of irradiation treatment, chemotherapy, and depleting antibodies.

In one embodiment, the lymphodepleting treatment is irradiation treatment.

In another embodiment, the lymphodepleting treatment comprises chemotherapy using a lymphodepleting agent, such as cyclophosphamide. Cyclophosphamide is just one form of chemotherapy which can be used to precondition (lymphodeplete) the host. Other alternatives are fludarabine, busulfan, melphalan or depleting antibodies, such as Mabthera.

As described herein, a goal of the lymphodepleting step, in combination with the selected dosage of allogeneic chimeric cells, is to suppress the immune system for a time sufficient to allow the antitumor activity of the tumor-directed allogeneic chimeric T cells to be manifested. It is important that the native immune system regenerate in a reasonable amount of time so as to attack the allogeneic T cells and remove them from the system after they have served their initial purpose. Preferably, the lymphodepleting step will reduce the amount of T cells in the host by the same, or approximately the same amount, as will be added in the adoptive cell transfer therapy. Accordingly, in a preferred embodiment, the amount of allogeneic chimeric T cells administered is sufficient to return the lymphodepleted lymphocyte population to its homeostatic amount, i.e., the normal amount for that patient when healthy. Thus, lymphodepletion with the adoptive cell transfer procedures will preferably maintain a balance of cells in the host to minimize both GvHD and HvGD, while allowing the GvH antitumor activity.

The maximum radiation or chemotherapeutic dosage for lymphodepletion must be less than the amount that would require rescue of the host immune system by bone marrow transplantation (BMT). For example, in the mouse model, mice can withstand less than 500 rads of irradiation treatment without the need for BMT. At 500 rads or more, BMT will be needed. For chemotherapeutic agents, the minimum dosages for use with BMT are known in the field. Acceptable dosages can be extrapolated from what is known. For clinical trials, the skilled person could empirically determine the optimum amounts so as to prevent GvHD and also prevent the need for BMT. As would be known to anyone designing clinical trials to determine optimum dosages for lymphodepletion and for ACT administration, escalating dose regimes would be used while carefully monitoring the immune response, such as by the mixed lymphocyte reaction or by monitoring cytokine release into the blood. If the allogeneic cells are seen to be attacking normal cells in the patient, then the lymphodepletion and/or cell dosage was too high. If the allogeneic cells are eliminated before attacking the tumors to which they are directed, the lymphodepletion and/or cell dosage was too low.

The allogeneic T cells are tumor-specific allogeneic T cells. The allogeneic T cells can be activated and expanded before the administering step. The T cells are activated in vitro with concanavalin A (conA) or CD3/CD28 antibodies for 48 hours, and then expanded with a cytokine such as IL-2, IL-7, IL-15 and/or IL-21 for up to 5 days. Tumor cells may also used as an activator.

In the method of the present invention, the number of allogeneic T cells administered to the subject is greater than 30 million. The number of cells ranges between 5 to 100 million. The number of cells may be chosen from 5, 10, 15, 20, 25, 30, 35, 40, 45, 50, 55, 60, 65, 70, 75, 80, 85, 90, 95, or 100 million cells. In the present application, the term "a cell" or "cells" as used herein refers to singular cells as well as populations of cells.

The allogeneic T cells can be administered in one or more doses and over a period of time.

The T cells of the present invention may be obtained from any source, such as a blood blank or a donor (e.g., an offspring, sibling, or parent of the patient), just so long as they are allogeneic. By allogeneic, it is understood that the cells or tissues are genetically different because they are derived from separate individuals of the same species.

While individual needs vary, determination of optimal ranges of effective amounts of a given cell type for a particular disease or condition is within the skill of the art. The dosage administered will be dependent upon the age, health, and weight of the recipient, kind of concurrent treatment, if any, frequency of treatment, and the nature of the effect desired. Determination of the effective amounts, for any given degree of lymphodepletion, can readily be made empirically by those of ordinary skill in the art without undue experimentation, as discussed above.

The compositions, such as pharmaceutical compositions, of the present invention can be administered by any of a number of means and routes known in the art. Preferred routes include parenteral, intravenous, intratumoral, intramuscular, subcutaneous, intraperitoneal, intra-articular, intracerebroventricular, or intraluminal. Also included is the "intrathecal" route, which is intended to encompass injection, infusion or instillation directly into a cavity or space surrounding an organ or body region in which an undesired immune/inflammatory response is occurring. Such spaces include the pleural space, peritoneum, subarachnoid space or dural space, or pericardial space. The generic term for administration into a sheath encasing an organ is termed "intrathecal" (see, for example, definition in Dorland's Medical Dictionary $29^{th}$ Edition, WB Saunders (2000) and Stedman's Medical Dictionary, $27^{th}$ Edition, Lippincott, Williams & Wilkins (2000)), as meaning "within a sheath." As used herein, this term is intended to be broader than a more commonly used definition which is limited to intracranial spaces.

The compositions, methods, and products of this invention are applicable to human and veterinary uses. The preferred animal subjects to be treated are mammals, and preferably, humans.

The present invention further provides a therapeutic composition, such a pharmaceutical composition, comprising the allogeneic T cells and, optionally, one or more of the other active agents described herein, along with any pharmaceutically acceptable excipient or carrier. As used herein, a therapeutically acceptable carrier includes any and all solvents, including water, dispersion media, culture from cell media, isotonic agents and the like that are non-toxic to the host. Preferably, it is an aqueous isotonic buffered solution with a pH of around 7.0. The use of such media and agents in therapeutic compositions is well known in the art. Except insofar as any conventional media or agent is incompatible with the allogeneic T cells of the present invention, use of such conventional media or agent in the therapeutic compositions is contemplated. Supplementary active ingredients can also be incorporated into the compositions.

The present invention may be optionally used in combination with other known cancer treatments and therapies, and herein refers to all pharmacological agents and/or drugs that treat cancer, and preferably as an adjuvant therapy to avoid metastatic development, such as mrd-minimal metastatic disease.

Discussion and Results

The objective of the present application was to develop safe and effective allogeneic adoptive therapy for the treatment of cancer.

Prior to the instant application, adoptive therapies used syngeneic cells almost exclusively, meaning that each treatment had to be specifically fabricated per patient at considerable cost and expense. T-bodies can attack tumors in an MHC independent manner [8], and therefore fully mismatched allogeneic T-bodies could be used as 'universal effector cells', capable of enabling ACT regardless of the patient MHC. The use of allogeneic T-bodies could therefore constitute a quantum leap in terms the economics of ACT, turning it into standardized therapy. An unappreciated bonus to using allogeneic ACT could be promotion of better understanding of tumor immunotherapy by allowing direct patient to patient comparisons treated using the same cells in contrast to the current situation where each patient is treated using a different batch of cells.

The first approach used to enable allogeneic ACT was by preventing the HvG reaction by 'stealthing' the transferred cells. ShRNA showed promise in silencing MHC I expression (FIGS. 1-2), but expression of inhibitory ligands failed to inhibit NK cytotoxicity sufficiently (FIG. 5), which led the inventors to seek a second approach.

Figure 10A:
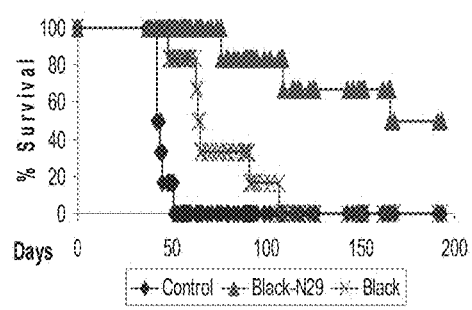
FIGS. 10A-10B: Allogeneic T-bodies provide superior therapeutic benefit as compared with allogeneic T cells against a tumor in ACT. Balb/c mice (n=6) were inoculated (iv) with $10^5$ Renca-erbb2 cells, and irradiated on day 7.
Figure 10B:
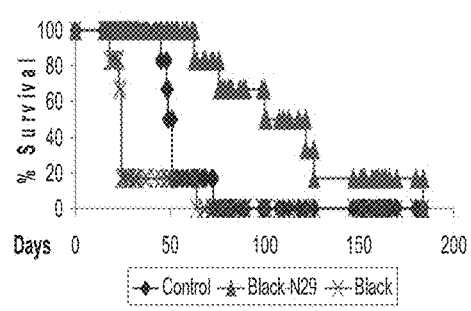
Figure 11A:
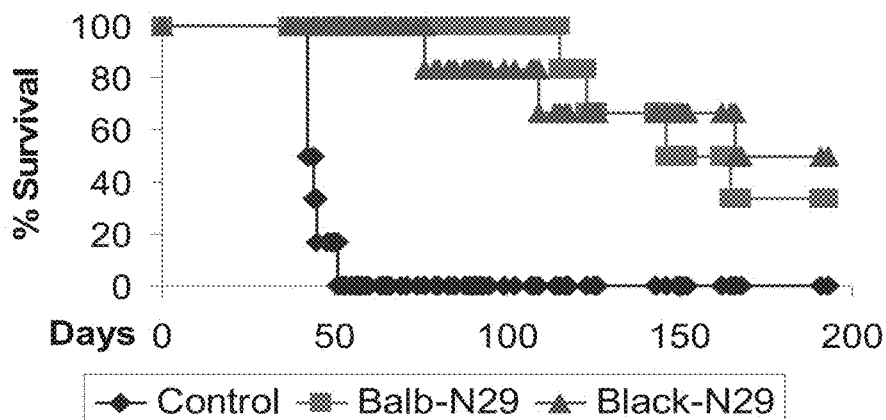
FIGS. 11A-11C: Transgenic allogeneic T-bodies provide comparable benefit to transgenic syngeneic T-bodies. Balb/c mice (n=6) were inoculated (iv) with $10^5$ Renca-erbb2 cells, and irradiated on day 7. Results represent one experiment out of two.
Figure 11B:
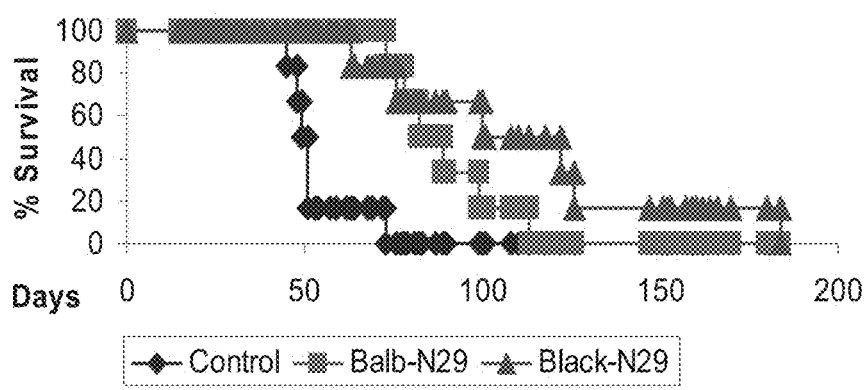
Figure 11C:
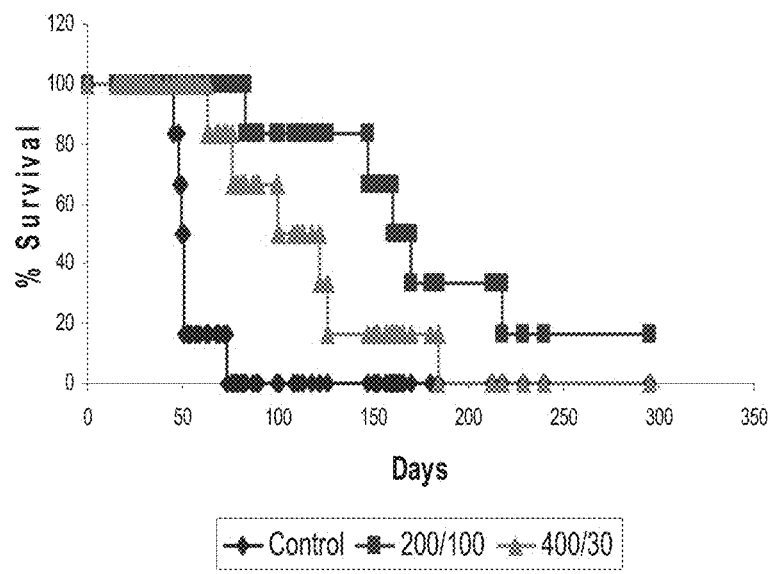
Figure 14:
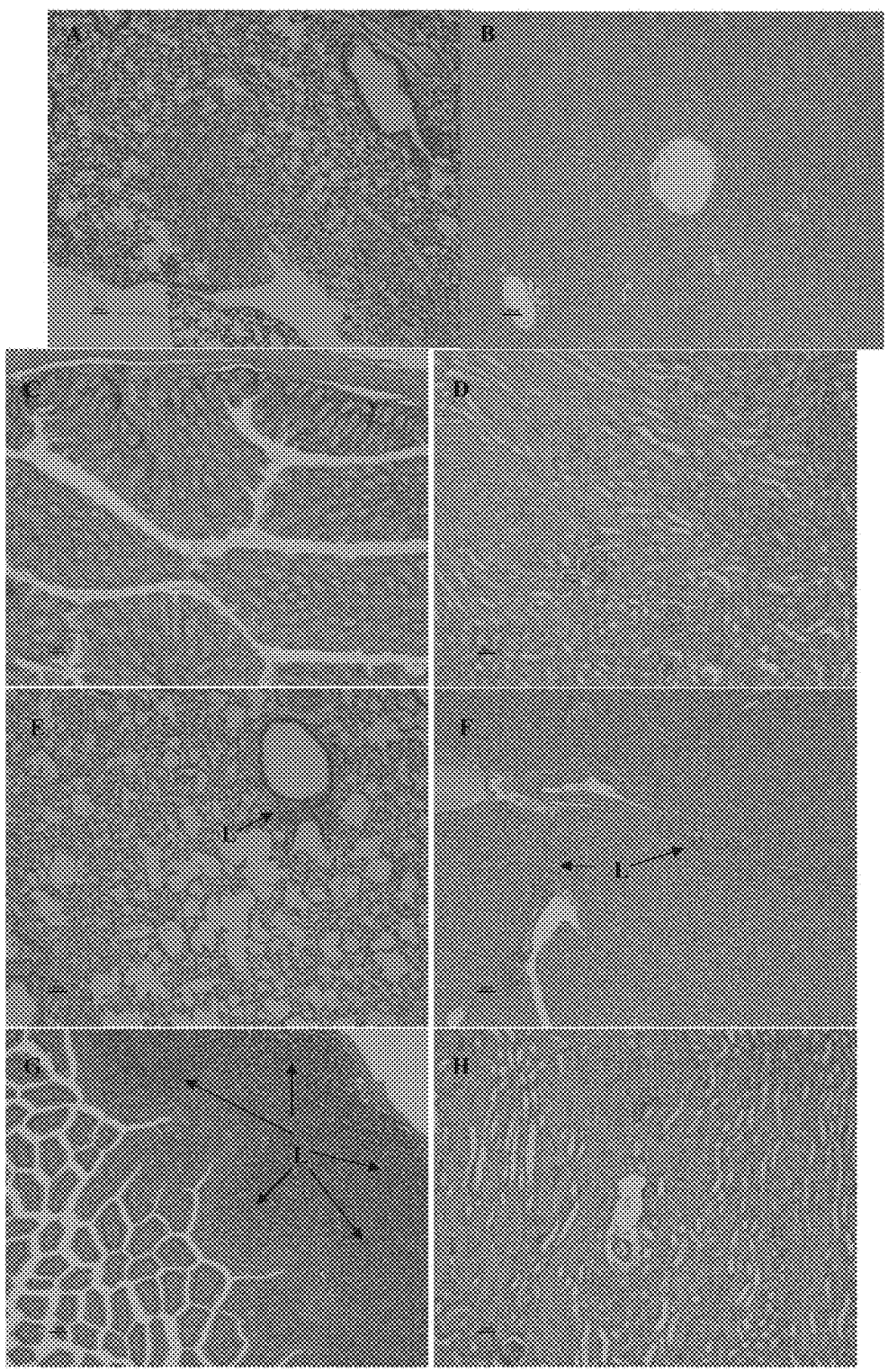
FIGS. 14A-14H: Allogeneic therapy is safe. Balb/c mice were irradiated with 200 rads and injected with 100 million activated C57Bl T cells 1 and 3 days later. Mice were sacrificed on days 4 and 6, their organs were stained with hematoxylin and eosin, and analyzed for GvHD.
Figure 16:
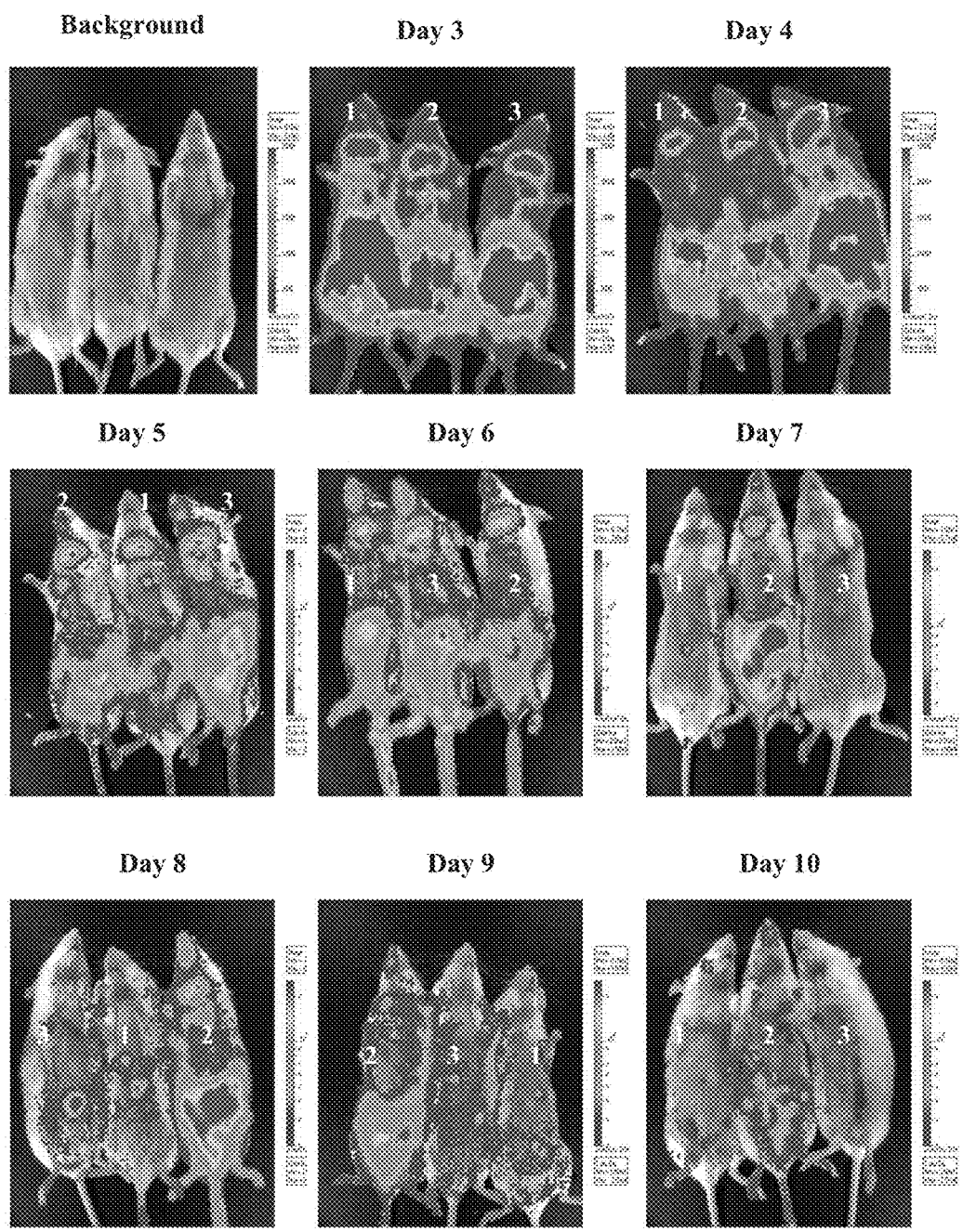
FIG. 16: Persistence of adoptively transferred FVB-Luciferase cells. Balb/c mice were injected with $10^5$ Renca-erbb2 cells iv, and then irradiated with 200 rads on day 7. Mice were then injected with 50 million FVB-Luc T cells iv 1 and 3 days after irradiation. Mice were examined by IVIS, beginning with the day after the second injection (Day 3). Each mouse was numbered and followed individually. Background figure shows mice not injected with FVB-Luc cells.
Figure 17A:
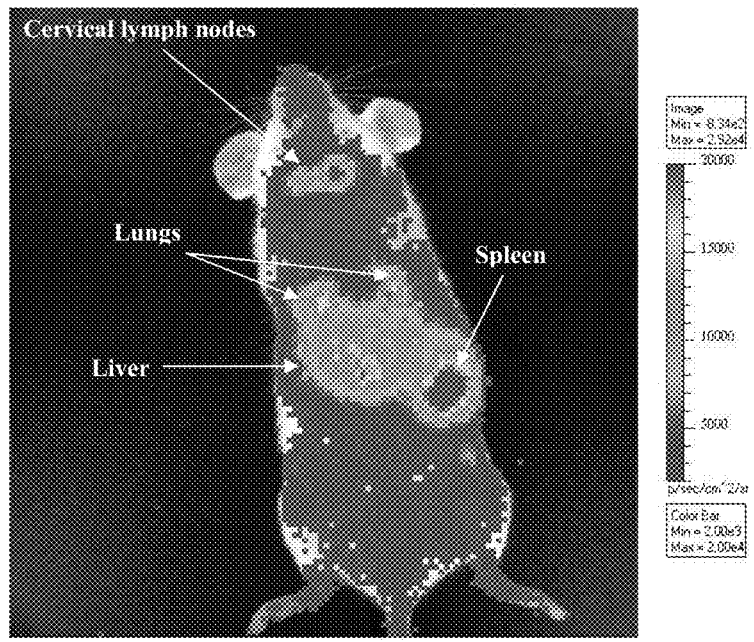
FIGS. 17A-17C: Localization of adoptively transferred FVB-Luciferase cells. Balb/c mice (n=3) were irradiated with 200 rads, and then injected with 50 million FVB-Luc cells IV the following day. One day later whole mice and specific organs were examined by IVIS. Images are from one representative mouse.
Figure 18A:
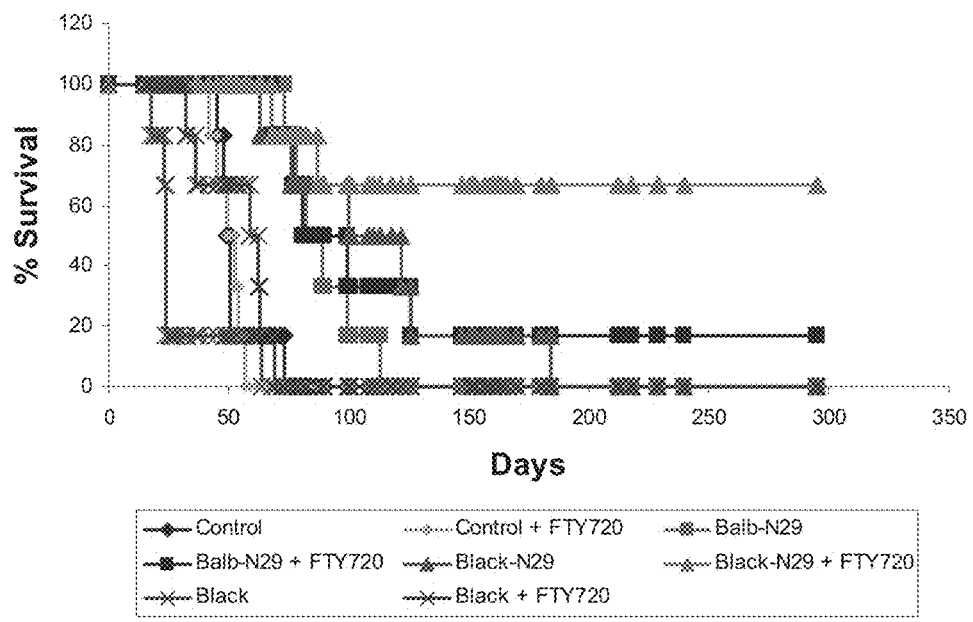
FIGS. 18A-18B: FTY720 prevents GvHD, and concurrently extends survival of tumor bearing mice. Balb/c (n=6) were inoculated with $10^5$ Renca-erbb2 cells IV on day 1. Some groups received daily FTY720 injections on days 8-18 (ip, 0.3 mg/kg). Death before day 45 as seen in (A) is due to GvHD which is easily distinguishable from death due to the tumor (GvHD associated death had the following characteristics: cachexia, hunched posture, liver cirrhosis). Results represent one of two experiments.
Figure 18B:
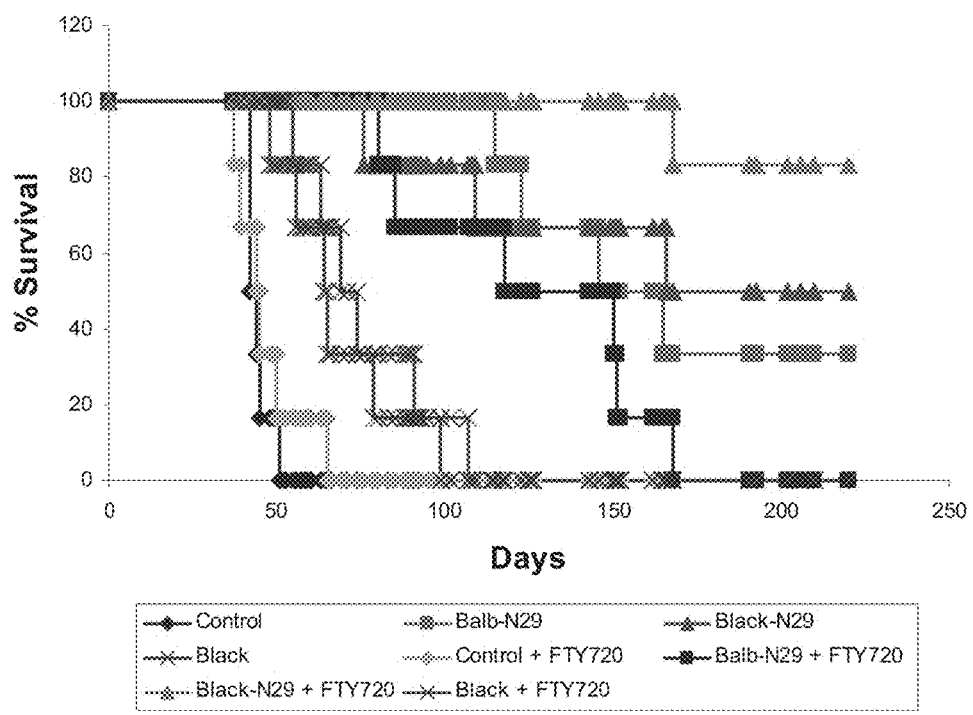
Figure 19A:
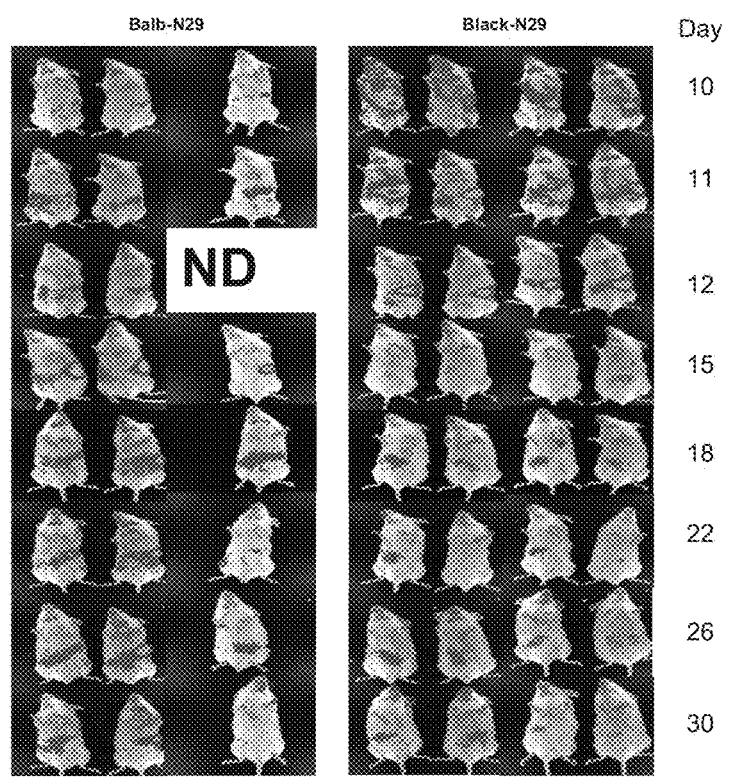
FIGS. 19A-19C: Dynamics of the T-body tumor specific response in vivo. Tumor specific T-body response was tracked by transferring Luciferase expressing T-bodies and monitoring bioluminescence in the IVIS.
Figure 19B:
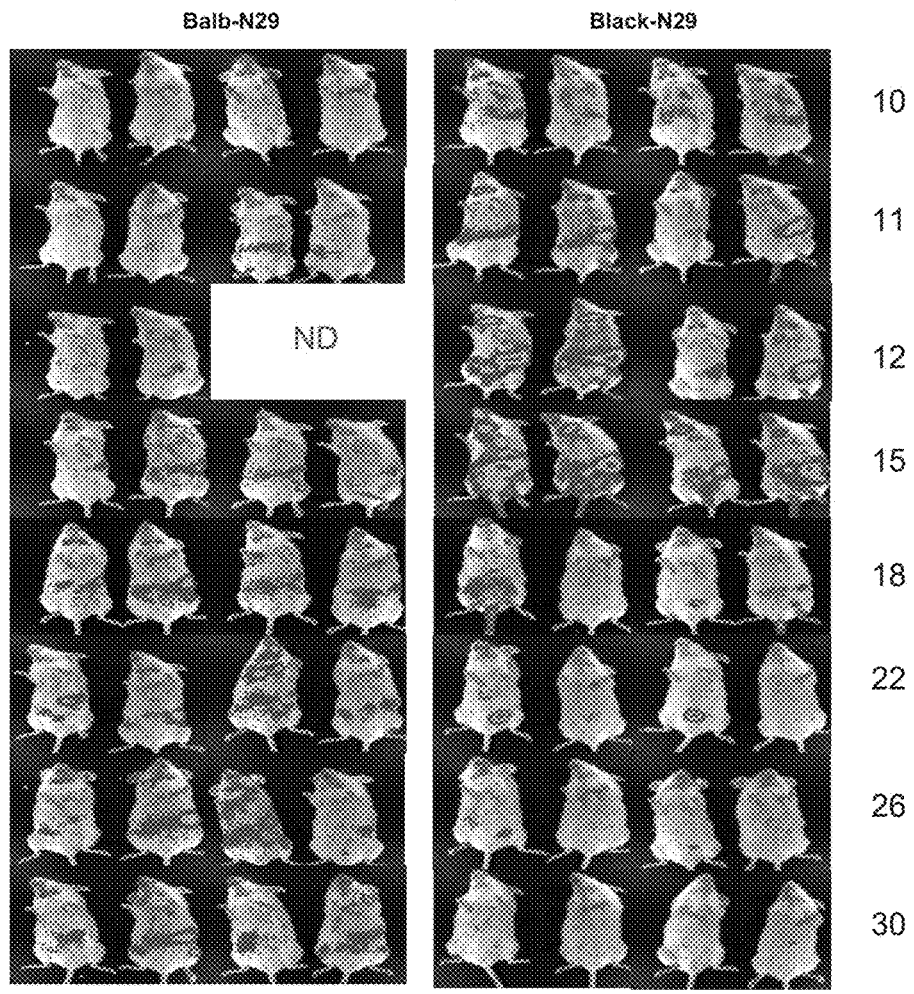
Figure 19C:
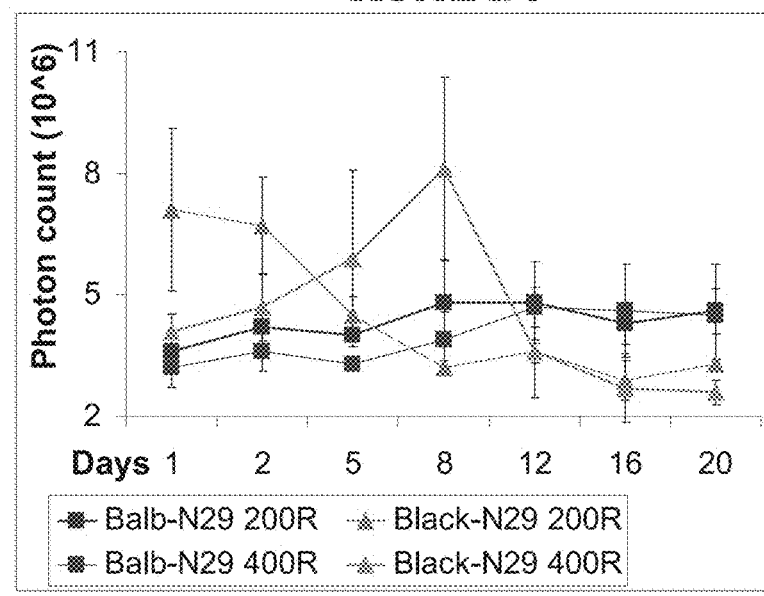
Figure 20A:
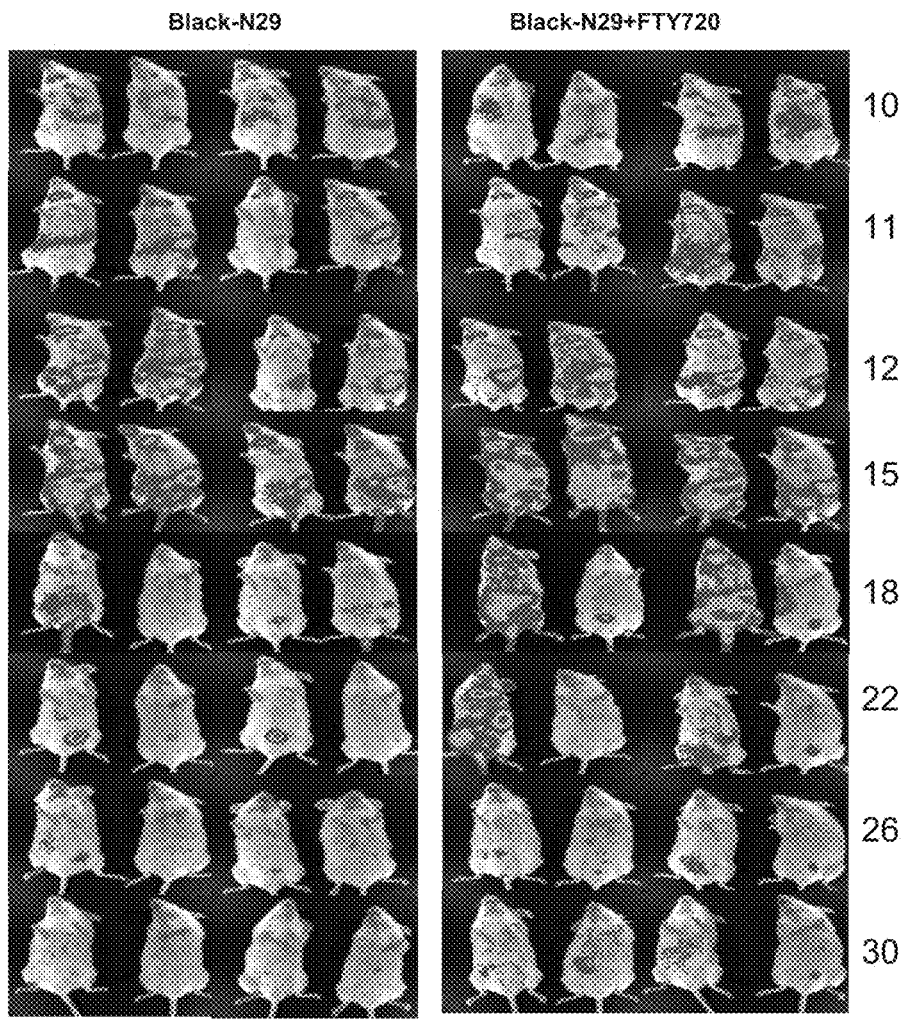
FIGS. 20A-20B: Prevention of egress FTY720 prolongs in vivo survival of adoptively transferred allogeneic T-bodies. Tumor specific T-body response was tracked by transferring Luciferase expressing T-bodies and monitoring bioluminescence in the IVIS.
Figure 20B:
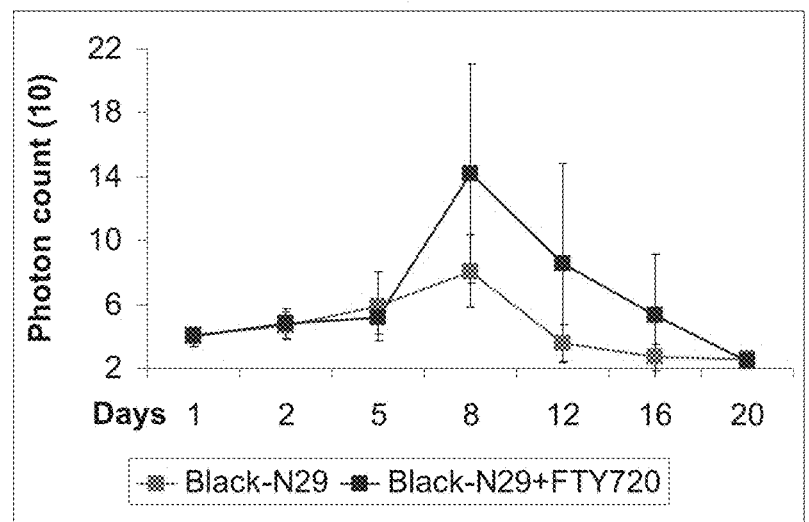

In the second approach, the inventors hypothesized that partial lymphodepletion might create a therapeutic time window in which T-bodies could attack and destroy the tumor, but would nevertheless be rejected, thereby preventing GvHD. Using this strategy, the inventors sought to demonstrate that very large numbers of open repertoire redirected T cells can be administered safely, without GvHD associated mortality, and very little damage as assessed by histology. The results of the present application show that allogeneic T-bodies can mediate significant therapeutic benefit in a clinically relevant model of minimal residual disease of HER2$^+$ solid tumor model, tripling median survival time compared with the untreated group with 30-40% long term survivors (FIG. 11). Adoptive transfer of large numbers of allogeneic T-bodies to pre-conditioned mice mediated equivalent benefit to syngeneic T-bodies, and was far superior to wild-type allogeneic cells, demonstrating that the response was tumor specific (FIG. 10). The treatment included relatively mild preconditioning and no BMT, leaving the host's immune system relatively intact. The transferred cells did not engraft, and persisted in vivo only transiently (FIGS. 16, 19, and 20), avoiding potential risks resulting from insertional mutagenesis by gene modified retrovectors [44-46]. When injected i.v., allogeneic donor cells could be detected in the lung, liver, spleen, bone marrow and the lymph nodes which constitute the most common sites for cancer metastases (FIG. 17A). Histological analysis confirmed this migration pattern, and showed cellular infiltration of lung, liver, and the intestine (FIG. 14). Temporary treatment with FTY720 concurrently inhibited GvHD, and potentiated the anti-tumor response. Under these conditions, 50-80% of tumor bearing mice survived long term (FIG. 18), proving that allogeneic cells can provide superior benefit compared with syngeneic cells. In vivo imaging data using luciferase expressing T-bodies demonstrate that prevention of lymphocyte egress through administration of FTY720 prolongs in vivo survival of allogeneic T-bodies (FIG. 20).

Application of allogeneic ACT is very challenging because of the dual problems of HvG which limits persistence of allogeneic cells on one hand and GvH which can occur if allogeneic cells are left unchecked, on the other hand. Thus far, virtually all attempts at allogeneic ACT have been done in the setting of allogeneic BMT (allo-BMT). Since the host is transplanted with the donor hematopoietic system, it does not reject any more cells of donor origin, in other words the HvG reaction is completely abolished. Instead of host rejecting the cells, the transferred cells attack the host, causing severe GvHD in many patients (even in cases of full MHC matching). Importantly, while this strategy can be effective against hematological disease (particularly CML), it does have its drawbacks, namely the need for complete or nearly complete MHC matching between donor and host. In addition even when a suitable donor is found for allo-BMT, only that donor's cell can be successfully transferred post-BMT which means that this strategy can not be employed as a standardized therapy.

Figure 6A:
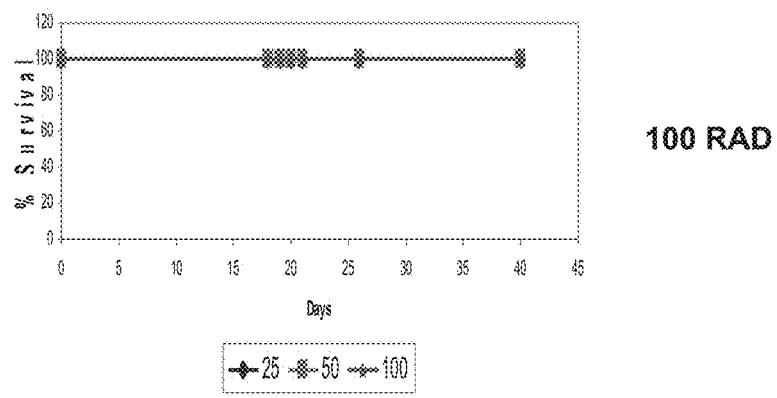
FIGS. 6A-6D: GVHD as a function of cell dose and irradiation dose. Survival curves of Balb/c mice (n=6) after adoptive transfer of activated wildtype C57Bl T cells. Balb/c mice were irradiated on day 0, and injected iv with C57Bl T cells (on days 1 and 3). Mortality only occurred after irradiation with 400 rads.
Figure 6B:
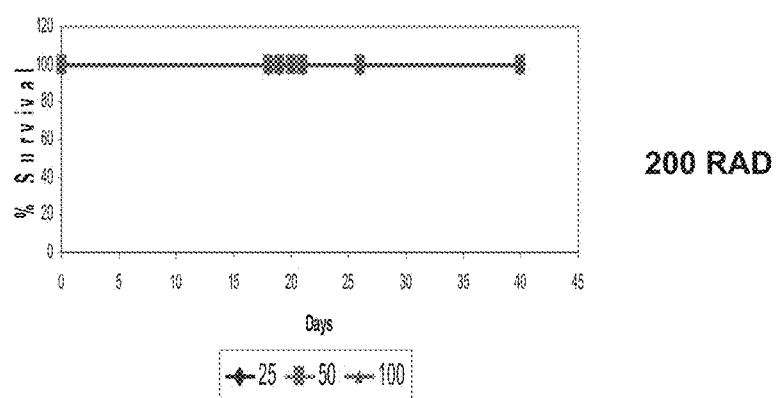
Figure 6C:
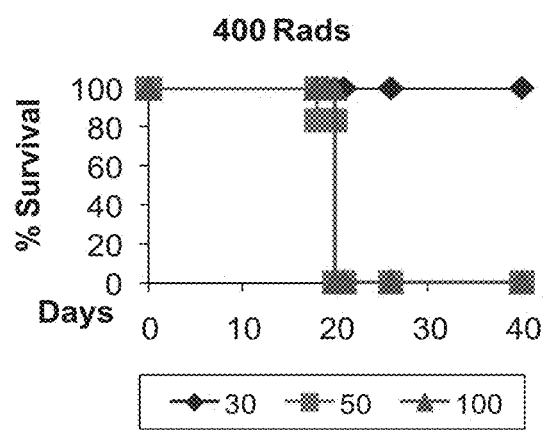
Figure 6D:
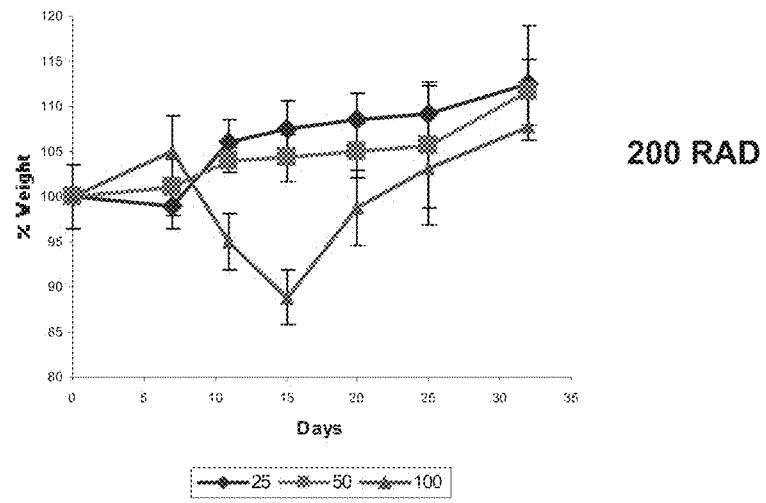

Since an objective of the present application was to develop standardized allogeneic ACT, an alternative strategy to allo-BMT was needed. It was found that a therapeutic time window can be created using lymphodepletion which would allow donor cells sufficient time to attack the tumor before being rejected. Creation of such a time window would require careful titration of not just host preconditioning, but also of the number of transferred cells. As expected, it was found that the risk of GvHD is a function of both radiation dose, and cell dose (FIG. 6). Interestingly, it was found that lethal GvHD could not be induced when using low doses of radiation (200 rads), even when transferring as many as $10^8$ activated T cells (FIG. 6B). In contrast, as few as $50*10^6$ activated T cells (wildtype C57Bl, not C57Bl-N29) could cause lethal GvHD after irradiation with 400 rads (FIG. 6C). Impressive therapeutic results were achieved in the tumor model using either regimen (400/30 or 200/100), demonstrating that a high cell dose can at least partially compensate for a low radiation dose and vice versa. Finally, it was shown that lymphodepletion before allogeneic ACT could be accomplished using chemotherapy (cyclophosphamide in this case), and not just radiation. Transfer of $10^8$ activated T cells following preconditioning with 200 mg/kg cyclophosphamide caused 100% lethal GvHD (data not shown), demonstrating that cyclophosphamide (at 200 mg/kg) depletes lymphocytes more effectively than 200 rads irradiation. As expected, increased preconditioning (200 mg/kg cyclophsophamide vs. 200 rads) allowed for the use of a smaller cell dose ($20*10^6$ vs. $10^8$), while maintaining equivalent benefit between allogeneic and syngeneic T-bodies (FIG. 13), conclusively demonstrating that lower cell doses could be used in conjunction with increased preconditioning without compromising antitumor efficacy and without causing GvHD.

An underlying assumption of the therapeutic time window strategy is that successful ACT can be accomplished even with limited persistence of the transferred cells. It was reasoned that the efficacy of the antitumor response is proportional not only to the duration of the immune response but also to its magnitude, and therefore a short but powerful response may be as effective as a weaker response with a longer duration. This assumption challenges the current prevailing view in the field of immunotherapy that curtailed persistence is one the major limitations facing immunotherapy today, and that enhancing persistence will improve the efficacy of immunotherapeutic approaches. This view is supported by data from clinical trials showing a correlation between persistence of transferred cells, and therapeutic benefit [47, 48]. Klebanof et al. showed that transferring central memory T cells provide superior therapeutic benefit in a model of murine melanoma, and persist in vivo for a longer time as compared with T cells with an effector memory phenotype [20]. The superior therapeutic benefit provided by central memory T cells depended on homing to the lymph nodes where the T cells proliferated extensively in response to vaccination and high dose IL-2 [20]. It is possible that the correlation between persistence and therapeutic benefit may simply reflect the fact that enhanced functionality (by the central memory T cells) might also lead to enhanced persistence, but that long term persistence itself is not a perquisite to successful ACT. Indeed, impressive therapeutic results were achieved (FIGS. 11 and 12), despite the fact that the cells were eventually rejected (FIGS. 16, 19 and 20). Presumably, the use of large numbers of cells ($10^8$) compensated for the limited persistence. Increased preconditioning can delay the rejection of the transferred cells, thus increasing their persistence. However, increasing persistence also increases the risk of GvHD (FIG. 6), and therefore increased preconditioning comes at the expense of the cell dose. When comparing lower preconditioning/higher cell dose (200/100) regimen and the higher preconditioning/lower cell dose (400/30) regimen, increased cell dose was more effective then increased radiation dose in my tumor model (FIG. 11C), demonstrating that in some tumor models increasing persistence is not necessarily the optimal choice when considering both antitumor efficacy and the risk of GvHD.

Finding the balance between antitumor efficacy and avoiding GvHD can also affect other aspects of allogeneic ACT. Namely the phenotype of the transferred T cells can have a profound impact on the outcome of the therapy. In the syngeneic setting, the superior efficacy of central memory T (Tcm) cells over effector memory T (Tem) cells in a model of murine melanoma has been shown to stem from the ability of Tcm cells to traffic to the lymph nodes and then massively proliferate in response to vaccination [20]. This enhanced functionality of Tcm has also been shown in the setting of allo-BMT [23]. Tcm cause more serious GvHD than Tem, and again this enhanced functionality depended on trafficking to the lymph nodes followed by massive proliferation [18]. Thus. Tcm are more potent effectors both in the antitumor response and the GvH response, and therefore they are not necessarily the optimal choice for use in allogeneic ACT [23]. One interesting example of a therapy which avoids using Tcm cells in allogeneic ACT has been developed in Robert Negrin's lab, and instead it uses cytokine induced killer cells (CIK) [27]. CIK cells are generated through culture of T cells in the presence of IFN-γ, and are capable of killing a wide range of tumors in vitro in an NKG2D dependant manner [27, 29]. One of the interesting features of these cells is that when donor derived CIK cells are transferred after allo-BMT they cause much less GvHD as compared with fresh donor splenocytes [27]. Investigations into the mechanism behind this reduced capability for GvHD have shown that these cells have the phenotype of terminally differentiated T cells, and have a greatly reduced capacity for proliferation after adoptive transfer [28]. CIK cells have shown some efficacy in murine models of minimal residual lymphoma, demonstrating that antitumor efficacy can at least be partially maintained despite lack of GvHD [27, 28]. This approach demonstrates the utility of using terminally differentiated T cells in the allogeneic setting despite their functional limitation (particularly the reduced capacity for proliferation). While this approach provided therapeutic benefit, it is noteworthy that the tumor burden in their model is relatively low (injection of tumor cells and CIK one day after allo-BMT), and that the hematopoietic tumors, which they utilized in their model, are particularly susceptible to allogeneic attack. More challenging tumor models with higher tumor burdens necessitate the use of Tcm, and would therefore require finding a satisfactory solution to the problem of GvHD.

Prior to the instant application, there have been several studies in recent years which have used allogeneic adoptive therapy to treat cancer. Most of these attempts involved transferring various types of donor cells (for example CIK cells) following allo-BMT, and this type of treatment has to be specifically fabricated per patient. Nevertheless, two noteworthy studies were published which did not employ allo-BMT. In one study, Boni et al. showed that adoptive transfer of allogeneic transgenic TCR splenocytes into 9 Gray irradiated mice in conjunction with autologous BMT can treat established B16 melanomas [30]. Although the therapeutic results are impressive, this strategy cannot be used as a standardized treatment and it is still in doubt whether this therapy could be clinically adapted. Unlike the research described herein in the instant application, Boni et al. use haploidentical transgenic splenocytes as donor cells [30]. While challenging, this is not a fully mismatched model, and therefore donor-host matching would still be needed, negating the possibility of using this strategy as a standardized therapy. The clinical application of this study is challenging because the success of this therapy hinges on the use of transgenic TCR splenocytes. The investigators demonstrate that the lack of GvHD in this model stems from limited alloreactivity due to expression of a single TCR by all the T cells [30]. Translation of this therapy to the clinic would require generation of tumor specific T cells from polyclonal T cells. There are two main ways to generate such cells: expansion of antigen specific T cells or redirection through transduction with either a TCR or a chimeric receptor (as done in the present application). However, while transduction can be used to redirect T cells, the endogenous TCR retains its functionality, essentially creating open repertoire tumor specific T cells which would cause severe GvHD as the investigators showed in their paper [30]. The alternative option of expanding antigen specific T cells faces two hurdles. The first hurdle is that while the TCR repertoire of CTL is limited, it is by no means monoclonal. Therefore, while such CTL lines will definitely cause less GvHD than open repertoire T cells, they will, nevertheless cause more GvHD than monoclonal T cells used in the study. The second hurdle is that expanding T cells requires extended propagation time which cause progressive differentiation of T cells and subsequently gradual loss of proliferative capability (as shown by the same group [49]). In the study, the investigators transferred naïve TCR transgenic splenocytes, while in clinical practice they would have to employ T cells which were previously activated and at least partially differentiated. This means that the therapeutic benefit observed in this study is probably an overestimation of the benefit which could be achieved in the clinic. It is precisely because of these issues that in the present application, T-cells were both activated and expanded before adoptive transfer so that the experiments would more faithfully simulate clinical practice.

In another recent publication prior to the instant application, Zakrzewski et al. adoptively transfer CAR-modified (chimeric antigen receptor)) allogeneic T-cell precursors after syngeneic BMT to treat a minimal residual disease model of murine lymphoma [31]. Maturation of the allogeneic T-cell precursors in the host purges their GvH reactivity, completely preventing GvHD [31]. Unfortunately, purging GvH reactivity, also purges GvL activity, as evidenced by the lack of efficacy of unmodified allogeneic T cell precursors against CD19 expressing murine lymphoma [31].

Tumor reactivity is conferred by transducing the T-cell precursors with an antitumor chimeric receptor (anti-CD19 in this study) [31]. This previous study presents a cutting edge strategy to treat post-BMT malignancy, and its combination with gene engineering provides a general way to target any tumor, providing a target antigen is known. However, the efficacy provided by the CAR modified cells was very modest, increasing median survival from 20 to around 30 days, with no long term survivors [31]. Similarly to the present application, the investigators also tried to treat metastatic disease using the Renca cell line transduced with GFP, Luciferase, and Thymidine kinase (Renca-TGL) [31]. A comparison between the data of this study to the data of the instant application is therefore of interest. Since treatment of Renca-TGL was done in a non-specific manner (no chimeric receptor redirection), one must compare their results to the results obtained in the instant application with unmodified allogeneic cells. In the present application, the inventors treated day 7 established Renca-erbb2 pulmonary metastases, while Zakrzewski et al. treated non-established Renca-TGL disease (the tumor and the adoptive transfer were injected on the same day). Zakrzewski et al. managed to extend median survival by 5 days, while the method of the instant application managed to extend median survival by 20 days, and in both cases there were no long term survivors [31]. Since the present inventors treated established metastases, while Zakrzewski et al. treated circulating tumor cells (a clinically irrelevant model), the present inventors still managed to provide significantly more therapeutic benefit, and it should be conclude that the treatment of the present application was at least one order of magnitude (and probably more) more powerful than their approach. This is most likely due to the number of mature T cells and their rate of maturation from the thymus [31]. At 14 days post-BMT there are less than $10^6$ donor derived (and therefore CAR expressing) T cells in the spleen, which expand to $3-4*10^6$ T cells by day 28 [31]. The number of tumor specific T cells generated in vivo is relatively low compared with most common protocols for ACT. In addition, the antitumor response takes some time (less than $10^6$ T cells by day 14) to develop, and this delay may allow the tumor to grow unimpeded, which might explain the relatively weak benefit provided by this treatment.

One feature that all attempts at allogeneic ACT share is the use of either autologous or allogeneic BMT. Allogeneic BMT is of course much more dangerous because of the risk of GvHD, but autologous BMT is not without its problems. Myeloid and lymphoid reconstitution takes time, and in that time life threatening complications can arise. The most notorious complications are opportunistic infections, as well as reactivation of latent viral infections such as CMV or EBV, all of which can have lethal consequences [13]. Because of the drawbacks of this treatment it is rarely offered as first line therapy, but instead reserved for patients who have failed other treatments or have relapsed. In addition, many patients (usually elderly patients) are ineligible for BMT due to poor physical condition. On top of all these concerns, the economic price of BMT is very high due to the prolonged hospitalization time needed by patients. For all these reasons, the treatment of the present application, which does not include BMT, has a distinct advantage over the alternatives, particularly as a first line treatment in the treatment of early stage disease, as well as an adjuvant therapy for minimal residual disease.

The results presented herein are very promising, and represent a proof of concept of safe and effective allogeneic adoptive cell therapy. An important point demonstrated by the work of the present application is that when applying allogeneic ACT, a balance must maintained between the extent of preconditioning and the number of the transferred cells. The inventors showed that using more preconditioning and lower cell doses can provide significant therapeutic benefit, and can be as effective as syngeneic ACT. Nevertheless, even the high cell dose the inventors used in one of the protocols ($10^8$) is realistic and can be utilized in the clinic. $10^8$ cells are roughly equivalent to the number of cells in the spleen of an adult mouse. The number of lymphocytes in the human spleen has been estimated to be roughly $10^{10}$, while the total number of lymphocytes in the body has been estimated to roughly $5*10^{11}$ [50, 51]. While these numbers may seem prohibitive, several clinical trials in the field of adoptive therapy do actually use cell doses on this order of magnitude, demonstrating the feasibility of the approach. Porter et al. infused as much as $10^{10}$ allogeneic lymphocytes stimulated ex vivo with aCD3/CD28 in a phase I clinical trial for the treatment of hematological malignancies [52]. In another trial, Rapoport et al. (also Carl June's lab) infused as many as $10^{10}$ aCD3/CD28 stimulated autologous for the treatment of CML patients in remission [53]. Dudley et al. (Steve Rosenberg's lab) infused as many as $10^{11}$ tumor infiltrating lymphocytes (TIL) in multiple clinical trials [7]. These studies demonstrate that generation of $10^{10}$-$10^{11}$ T cells from peripheral blood mononuclear cells is realistic, supporting the feasibility of high cell doses in ACT.

In a very recent study, Gattiononi et al. pioneered a novel culturing method that through addition of WNT signaling blocker TWS119 allows expansion of T cells while concurrently blocking their differentiation yielding T cells with the memory stem cell phenotype or Tscm [54]. These cells have a phenotype $CD44^{low}CD62L^{high}Sca-1^{high}CD122^{high}Bcl-2^{high}$ which is an even less differentiated phenotype than central memory T cells [54]. In a direct head to head comparison between central memory T cells, and memory stem cells T cells, Tscm were significantly more effective in treating established melanomas [54]. This technique and similar approaches will probably allow generation of large numbers of relatively undifferentiated T cells in the future, facilitating large scale production of cells for adoptive therapy.

The success of the present invention as a therapy in humans relies on finding the most powerful adoptive transfer regimen without causing significant GvHD. In mice, this was accomplished by calibrating the irradiation dose and cell dose, and monitoring mice survival. As this strategy cannot be used in humans, an alternative must be found. One way to circumvent this problem is to rely on clinical data from previous trials in patients. One area in which a wealth of information is readily available is clinical trials employing donor leukocytes infusions. These trials have extensively mapped out what allogeneic cell doses can be safely administered to patients previously transplanted with allogeneic bone marrow. Importantly, allogeneic BM transplant patients are already either partially or fully chimeric for allogeneic cells, which means that DLI will not be rejected by these patients. In the absence of HvG reactivity, these patients are much more susceptible to GvHD than non-transplanted patients, so the protocols developed for DLI make an excellent and safe starting point for allogeneic adoptive therapy. From this initial point, cell dose can be escalated, while patients are monitored for early signs of GvHD such as weight loss or elevation in liver enzymes. Even if GvHD does develop, it should be much more amenable to therapeutic intervention than the usual cases of GvHD that develop post all-BMT.

As demonstrated by the present application, low level preconditioning lead to limited in vivo persistence (FIGS. 16, 19, and 20) because the HvG response is not ablated (as is the case post allo-BMT) but merely delayed ensuring the eventual rejection of the cells and ultimately suppressing the GvH response. When the present inventors used the 200/100 regimen with unmodified allogeneic T cells, the treated mouse experienced transient weight loss (FIG. 6D) stemming from the GvH reaction of the transferred cells. Comparing the kinetics of weight loss with the in vivo imaging data (FIG. 16) show that the peak of the weight loss corresponded to the peak of the bioluminescent signal from the transferred cells and after their rejection the mouse regained the lost weight. As an additional precaution, allogeneic cells can be transduced with suicide genes which could be activated if GvHD develops [55]. The suicide gene strategy has been shown to effectively treat GvHD caused by central memory human T lymphocytes [55].

The biggest challenge associated with allogeneic adoptive therapy is the risk of GvHD. Initially, the inventors avoided GvHD by careful titration of the radiation and cell doses; however GvHD may be reduced further through additional manipulations. One alternative is to purge alloreactivity from the donor cells by relying on an anti-third party CTL transduced, a method pioneered by Professor Yair Reisner [56, 57], and then transduce these CTL with chimeric receptors. CTL stimulated by third party T cells demonstrate dampened anti-donor reactivity, and could potentially serve as donor cells in adoptive therapy with reduced risk of GvHD [56, 57]. The limitation of this method is that it is patient specific procedure as each patient would require a different third party stimulator, and therefore this method could not be utilized as a standardized therapy. An alternative approach was to use donor T cells with a restricted TCR repertoire which have very little GvH potential as demonstrated by the pmel transgenic splenocytes used in the study by Boni et al. [30]. The problem is that such T cells would still be MHC restricted, and therefore could not be used as 'universal effector' cells. However, creation of a bank of allogeneic CTL lines restricted by the most common MHC molecules could provide a solution to the vast majority of patients. The question arises what should be the target antigen for the CTL line. One possibility is to target another tumor antigen, thus conferring CTL T-bodies double tumor specificity via both the TCR and the chimeric receptors. The main problem with using CTL lines is that prolonged culture of cell in vitro reduces their functionality in vivo [49, 58]. Several studies have shown that acquisition of full effector function, and specifically an effector memory phenotype impairs in vivo antitumor efficacy [20, 49]. Interestingly, effector memory phenotype is also associated with greatly reduced risk of GvHD due to impaired migration into secondary lymphatic organs because effector memory cells do not express CD62L [18, 59]. Effector memory T cells mediate a curtailed response regardless whether the target is a tumor or the host. This curtailed response is associated among other things with reduced persistence of transferred cells [47, 48, 54]. In an attempt to boost the persistence of adoptively transferred effector memory T cells, Pule et al. transduced autologous EBV specific CTL lines with a GD2 specific chimeric receptor, infused them into neuroblastoma patients and compared their persistence with that of polyclonal activated T cells also transduced with the chimeric receptor [12]. The investigators showed that EBV specific CTL-GD2 persist for a much longer time in vivo than polyclonal activated T cells, presumably due to in vivo stimulation by EBV infected cells [12]. This strategy could be implemented through establishment of a handful of allogeneic lines, each restricted to one of the most common MHC molecules thus providing coverage for as many patients as possible. The efficacy of this strategy could theoretically be boosted further through intentional infection with attenuated viruses which would stimulate the lines much more powerfully than a latent infection. Taking this approach one step further would be to combine virus CTL T-body lines with oncolytic viruses which could damage the tumor, and stimulate the T-bodies in situ at the same time.

One common thread connecting all the approaches for dealing with GvHD is their attempt to curb or prevent GvHD. An alternative approach would be to take advantage of the GvHD response, and redirect it in a way which would benefit the antitumor response. Harnessing the awesome power of the GvHD has the potential of tremendously boosting the efficacy of an allogeneic antitumor response. In order to harness the power of the GvH response it is important to understand the dynamics of this reaction. Alloreactive T cells can attack peripheral tissues directly, but the true power of the response stems from allogeneic T cells migrating to secondary lymphatic organs. These cells encounter allogeneic dendritic cells which activate, and cause massive proliferation of allogeneic cells which fuel the GvH response [14]. Several studies have demonstrated that in vivo stimulation through vaccination can also significantly boost an antitumor response in the syngeneic setting [14]. In the case of an allogeneic antitumor T-body response, tumor specific T-bodies cells receive stimulation from allogeneic dendritic cells which indirectly support the antitumor response. A different tactic to harnessing the GvH response would be to redirect it against the tumor itself. Since the tumor is of host origin it is certainly susceptible to GvH attack, the challenge is how to direct anti-host donor cells to the tumor. An interesting approach employed by Kim et al. (Megan Sykes' lab) was to administer FTY720 concurrently with allogeneic BMT for treatment of hematological malignancies [60]. The rationale behind the treatment is that inhibiting egress of lymphocytes from lymphatic organs will ameliorate GvHD, but the GvH reaction in lymphatic organs will proceed unhindered attacking any hematological malignancies in those organs. Using this approach GvHD occurs, but is confined to the lymphatic organs which are also the site of the tumor [60]. While this approach is valid for hematological malignancies, the rationale does not hold for solid tumors. However, the inventors found that FTY720 could still provide therapeutic benefit in a solid tumor model treated with allogeneic cells. Of course, in the case of lymph node metastases, trapping the antitumor lymphocytes in the lymph nodes can enhance therapeutic efficacy, but this is not the case in a model in which metastases occur in the lung outside the lymphatic system.

The question remains how a substance that traps lymphocytes in the lymph nodes improves therapy of an extra lymphatic tumor. The key to answering that question is the realization that in allogeneic adoptive therapy there are actually two targets: the tumor, and the host's immune system. Allogeneic T cells attack, among other tissues, the host's immune system, thus weakening it and impairing the HvG response. In this manner, allogeneic cell rejection is presumably delayed thus enhancing the efficacy of the antitumor effect by extending the persistence of the antitumor lymphocytes outside the lymph nodes. Incorporating FTY720 into the treatment protocol yielded the best therapeutic efficacy of any of the regimens tested with allogeneic T-bodies providing superior therapeutic benefit to syngeneic T-bodies.

While there are many therapies which rely on allogeneic cells, the vast majority of them rely on either GvH reactivity (for example DLI) or TCR independent recognition (for example CIK cells) for their efficacy. There are very few allogeneic therapies which are antigen specific. Prior to the instant application, there was no report in the literature of any study showing equivalent efficacy between syngeneic and allogeneic cells. In the present application, not only did the inventors show equivalent efficacy, but they developed a protocol which provided superior benefit with allogeneic cells by redirection of the GvH response.

In summary, the research herein provides a proof of concept of allogeneic adoptive cell therapy. The combination of allogeneic T cells with a MHC unrestricted chimeric receptor yields 'universal effector cells' which could be used as a standardized therapy of cancer. The treatment did not include the use of BMT, and therefore avoids the significant toxicity and morbidity associated with it, as well as the need to find a matched donor which would have precluded its use as a universal therapy. Finally, the present application demonstrated that addition of FTY720 can inhibit GvHD, while concurrently enhancing the efficacy of the antitumor response. Under this strategy, the present inventors obtained superior results with allogeneic cells, as compared with syngeneic cells. Harnessing the GvH response to boost the efficacy of the antitumor response could make allogeneic adoptive therapy the treatment of choice not just for logistical and economic reasons, but also because of efficacy considerations.

The references cited above are all incorporated by reference herein, whether specifically incorporated or not.

Having now generally described the above-noted embodiments of the invention, the same will be more readily understood through reference to the following materials, methods, and examples which are provided by way of illustration, and are not intended to be limiting, unless otherwise specified.

EXAMPLES

The following methods and materials are used in various of the Examples that follow as well as in carrying out certain embodiments of the invention.

Example 1

Adoptive Therapy Using 'Unstealthed' Allogeneic Tumor Specific T Cells

The failure of the 'stealthing' approach led the inventors to seek alternative strategies to prevent the rejection of the transferred cells. One obvious method for preventing the rejection of the transferred cells is to completely ablate the host's immune system, and then rescue the host with either syngeneic or allogeneic bone marrow transplantation (BMT). The major difference between syngeneic or allogeneic BMT is that allogeneic BMT carries the risk of GvHD (even if the donor is MHC matched which is itself non-trivial). However, in the case of allogeneic ACT the difference between auto-BMT and allo-BMT is markedly blurred because the transferred allogeneic cells can cause GvHD by themselves. So in either case the major obstacle facing the lymphoblation approach is the risk of GvHD. It was surmised that the use of mild preconditioning might be sufficient to create a therapeutic time window in which the transferred cells could attack the tumor, but insufficient time to cause serious GvHD This approach is unique because it is predicated on the assumption that a sufficiently potent antitumor response could confer significant therapeutic benefit despite limited persistence in stark contrast to the prevailing view which emphasizes the importance of persistence [2].

Example 2

GvHD is a Function of Host Preconditioning and Cell Dose

It is well established that even a miniscule amount of allogeneic T cells present in the BM is sufficient to cause lethal GvHD, but the risk of GvHD has not been evaluated using milder conditioning protocols. Ideally, one would like to induce the most potent antitumor response without risking GvHD. Towards that end, the inventors preconditioned mice with increasing amounts of irradiation followed by transfer with variable amount of cells, in order to find the most potent adoptive transfer regimens which avoid GVHD. The inventors used activated C57BL/6-N29 T cells as donors, and Balb/c mice as recipients. T cells were activated in vitro with concanavalin A (conA) for 48 hours, and then expanded with IL-2 for up to 5 days. Activation is critical since the inventors planned to redirect the T cells against the tumor (in subsequent experiments and in the clinic) using retroviral transduction with the TPCR (which only infect proliferating cells). Cells were transferred one day after irradiation, and if >30 million were transferred then the cells were administered in two equal doses. FIG. 6 shows that the radiation dose (extent of ablation) is more important than cell dose in determining the risk of GVHD. No mortality and only transient weight loss were caused by administration of very high numbers of cells (100 million cells) after irradiation with 200 rads (abbreviated as the 200/100 regimen). In contrast administration of just 50 million after irradiation with 400 rads (abbreviated as the 400/30 regimen) caused 100% GVHD associated mortality.

Example 3

Figure 7A:
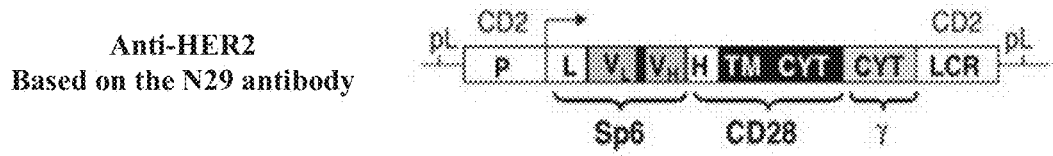
FIGS. 7A-7E: The Renca-erbb2 tumor model.
Figure 7B:
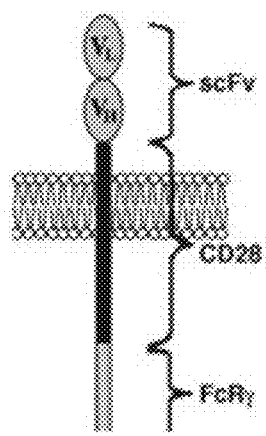
Figure 7C:
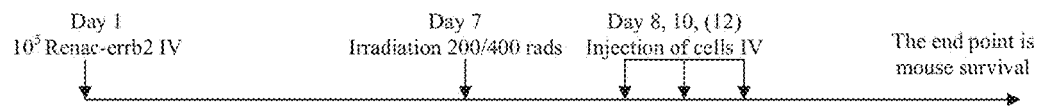
Figure 7D:
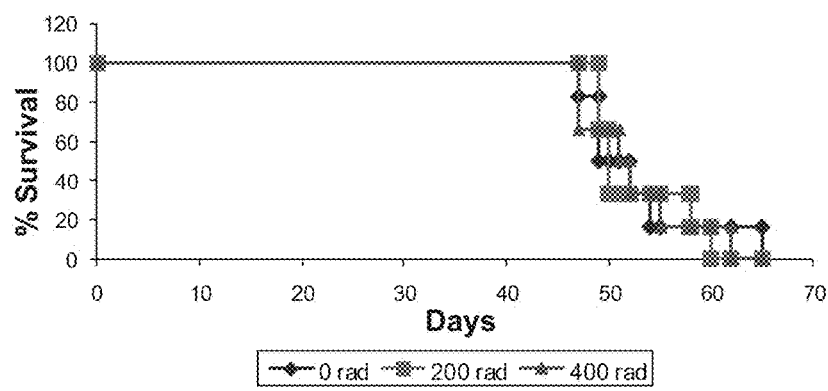
Figure 7E:
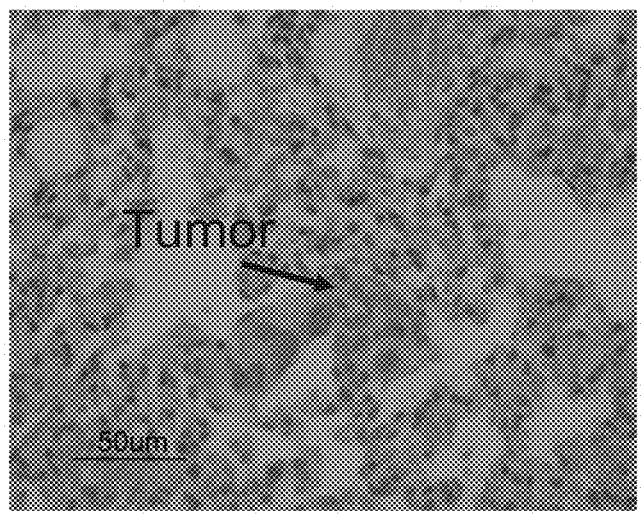
Figure 8A:
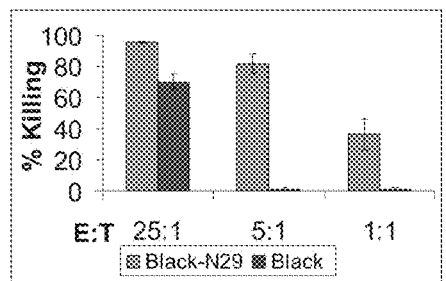
FIGS. 8A-8B: Allogeneic T-bodies are superior to wild type allogeneic T cells in functional assays against a tumor in vitro.
Figure 8B:
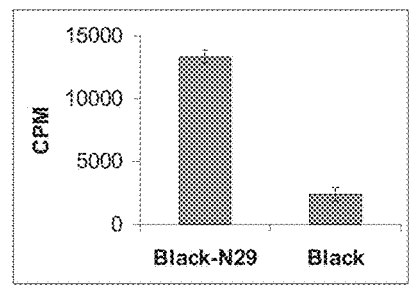

Transgenic Allogeneic T-Bodies are as Effective as Transgenic Syngeneic T-Bodies and Superior to Unmodified Allogeneic Cells in a Minimal Residual Disease Model of Cancer After determining safe regimens for adoptive transfer, the inventors tested the efficacy of tumor rejection by CR redirected T cells. The inventors used the Renca-erbb2, renal cancer cell line, stably transfected with erbB2 (HER2) which was injected intravenously into Balb/c mice to generate experimental pulmonary metastases. As effectors, the inventors used splenocytes from transgenic mice expressing a HER2 specific chimeric receptor (based on the N29 antibody derived scFv, FIGS. 7A-B) under the CD2 promoter (which is expressed in T and NK cells [8]). The HER2-specific transgenic mice were kept on two backgrounds: C57Bl and Balb/c (named C57Bl-N29 and Balb-N29 respectively). Wild type Balb/c mice were injected with the Renca-erbb2 on day 1, irradiated on day 7, and HER2 specific T-bodies were injected on day 8 (and also on day 10 and 12 in some cases). Irradiation was chosen for preconditioning because Renca is very resistant to radiation induced death, and is capable of withstanding even 900 rad [39]. Therefore, any therapeutic benefit from the treatment will be due to the immunotherapy and not the irradiation. In our system irradiation with up to 400 rad did not extend median the survival of mice (50±5 days) with pulmonary metastases as compared with untreated mice (FIG. 7D). At the time treatment was begun (day 8) the mice presented with hundreds of pulmonary metastases with a diameter of 50-100 μm (FIG. 7E). This tumor model simulates minimal residual disease, a clinically relevant situation where the primary tumor was resected, but the tumor had already spread systemically, leaving micrometastases throughout the body.

Figure 9:
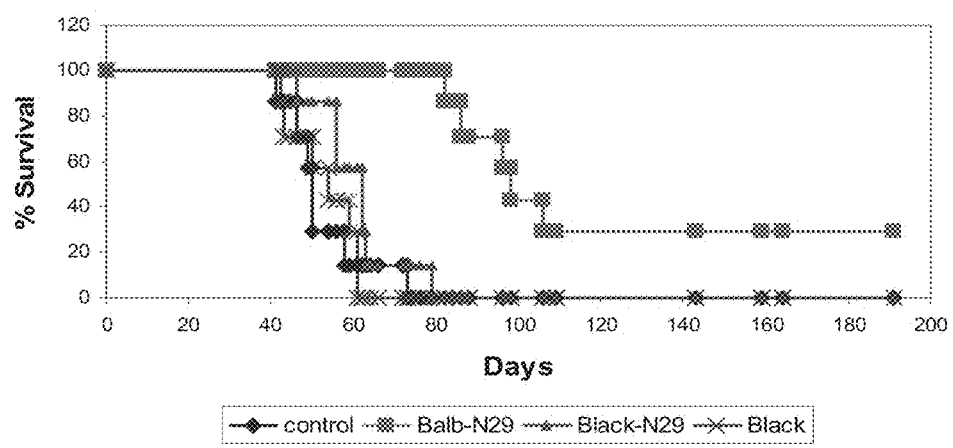
FIG. 9: Adoptive transfer of Balb-N29 T cells extends survival of Balb/c with Renca-erbb2 pulmonary metastases. Balb/c mice (n=6) were inoculated with $10^5$ Renca-erbb2 cells iv on day 1, irradiated on day 7 with 200 rads, and then injected with 10 million T cells on days 8, 10, and 12 (as well as 1000 u of IL-2 twice daily on days 8-18). Results represent one experiment out of two. Balb-N29 cells provide significant therapeutic benefit compared with the control group (P<0.0002), while wild type C57Bl provide none, and C57Bl-N29 provide only marginal benefit (boosting median to 62 days as compared with 50 for the control group).

In order for allogeneic adoptive therapy to be a viable option it must provide at least comparable therapeutic to syngeneic adoptive therapy. The inventors therefore compared the efficacy of allogeneic (C57Bl-N29) to syngeneic (Balb-N29) T-bodies, and to ensure that allogeneic cells mediate a specific antitumor response (and not just an allogeneic response), they also tested the effect of activated wild type C57Bl cells. Previous experiments in the inventors' lab have established that the minimal regimen which provides significant therapeutic benefit (boosting median survival to 90 days) using syngeneic Balb-N29 is irradiation with 200 rad and transfer of 3 doses of 10 million cells each (abbreviated as 200/30 regimen) complemented with low dose IL-2 (1000 u) twice daily. The purpose was to test if one can provide therapeutic benefit in this model using allogeneic C57Bl-N29 cells. The inventors used the initial regimen as a starting point with one important difference: instead of using naïve transgenic cells, the cells were pre-activated before transfer for 48 hours with concanavalin A. The reason for the change was to simulate a more clinically relevant situation in which lymphocytes will need to be activated in order to facilitate retroviral transduction with the chimeric receptor. Using the 200/30 regimen the median survival time of Balb-N29, C57Bl-N29, and C57Bl treated groups was 97, 62, and 52 days as compared with 50 days for the untreated group (FIG. 9, P<0.0002 for Balb-N29 vs. control group). Under these conditions syngeneic cells provided the best therapeutic benefit with C57Bl-N29 providing very modest benefit as compared to no benefit using wild type C57Bl cells. Importantly the benefit provided by C57Bl-N29 cells occurred in the absence of mortality, or weight loss, demonstrating that therapeutic benefit using allogeneic T-bodies precedes the development of any adverse side effects due a GvH response. It was surmised that allogeneic rejection is limiting the efficacy of allogeneic adoptive therapy and that increasing cell dose and/or radiation dose would increase persistence of allogeneic cells, thus enhancing therapeutic benefit. Using 200/100 regimen the median survival of Balb-N29, C57Bl-N29, and C57Bl treated groups was 165, 155, and 70 days respectively as compared with a median of 43 days in the untreated group (FIGS. 10 and 11. P<0.0004, 0.0004, 0.0015 for Balb-N29, C57Bl-N29 and wild type C57Bl groups respectively as compared with the control group). To the inventors' knowledge this is the first demonstration that allogeneic adoptive therapy can provide significant therapeutic benefit which is comparable to that achieved by syngeneic therapy in a clinically relevant model of minimal residual disease (no significant difference between Balb-N29 and C57Bl-N29. P=0.68). C57Bl-N29 cells doubled the median survival as compared with unmodified allogeneic cells, demonstrating that the immune response is indeed tumor specific, and not merely allo-specific (P<0.0031 for C57Bl-N29 vs. wild type C57Bl group). While this regimen is very effective, the inventors sought to determine if increasing the persistence of adoptively transferred cells further improves the outcome. Since it is probably not realistic to increase the cell dose (beyond 100 million), the inventors chose to increase the radiation dose to 400 rads. Using 400 rads and 30 million cells regimen the median survival of Balb-N29, C57Bl-N29, and C57Bl treated groups was 90, 110, and 24 days as compared with 50 days for the untreated group (FIGS. 10 and 11, P<0.002 for C57Bl-N29 and Balb-N29 groups as compared with the control group). Under these conditions allogeneic T-bodies provided slightly more benefit than syngeneic T-bodies, demonstrating that the radiation dose can indeed determine the relative efficacy of allogeneic vs. syngeneic cells. As expected increasing either cell dose or radiation dose, as compared with the initial 200/30 regimen, improved the efficacy of the treatment (results from several experiments summarized in Table 1 shown below).

TABLE 1

Summary of adoptive transfer experiments in the Renca-erbb2 pulmonary metastases model

| Cell Type | Cell Dose | # of cell doses | Irradiation dose | # of repeats | Median | Survivors > 150 days |
|---|---|---|---|---|---|---|
| Control | 0 | 0 | 0-400 | >10 | 50 ± 5 | 0% |
| Balb-N29 | $10^7$ | 3 | 200 | 3 | 106 ± 15 | 10% |
| C57Bl-N29 | $10^7$ | 3 | 200 | 3 | 72 ± 9 | 4.5% |
| C57Bl | $10^7$ | 3 | 200 | 2 | 65* | 0% |
| Balb-N29 | $10^7$ | 3 | 400 | 2 | 90 | 15% |
| C57Bl-N29 | $10^7$ | 3 | 400 | 2 | 111 | 15% |
| C57Bl | $10^7$ | 3 | 400 | 2 | 22* | 0% |
| Balb-N29 | $50 * 10^6$ | 2 | 200 | 3 | 156 ± 9 | 33% |
| C57Bl-N29 | $50 * 10^6$ | 2 | 200 | 3 | >137.5§ | 33% |
| C57Bl | $50 * 10^6$ | 2 | 200 | 2 | 68* | 0% |

All groups contained 6 mice.
*Average of two experiments
§Experiments are still ongoing (day >250), and median was not reached in some groups.

Interestingly, increasing the cell dose was more effective than increasing the radiation dose (the 200/100 regimen was more effective than the 400/30 regimen, medians of 155 and 110 days respectively (FIG. 11C), plus it was also safer, suggesting that a high cell dose regimen is the better choice for allogeneic adoptive therapy in this model.

Example 4

Transduced T-Bodies Behave Similarly to Transgenic T-Bodies

Figure 12A:
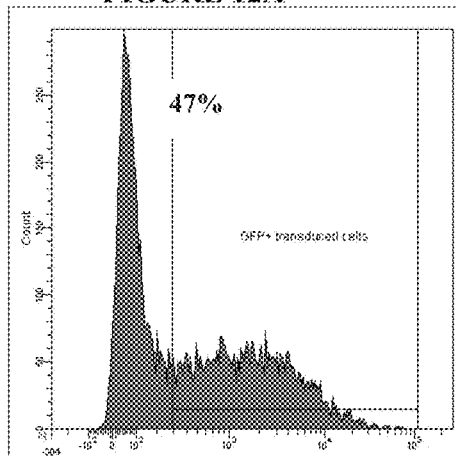
FIGS. 12A-12D: Transduced cells as effective as transgenic cells in treating the tumor. Balb/c mice (n=6) were inoculated (IV) with $10^5$ Renca-erbb2 cells, and irradiated 200 rads on day 7. Mice were either left untreated or injected with either N29 transgenic or transduced T cells from either the Balb/c or C57Bl background as well as an allogeneic C57Bl mock transfected control (control, C57Bl mock, C57Bl-N29 transgenic+wildtype C57Bl, C57Bl-N29 transduced, Balb-N29 transgenic+wildtype Balb/c, Balb-N29 transduced). Unlike other experiments this time splenocytes were activated by aCD3/CD28.
Figure 12B:
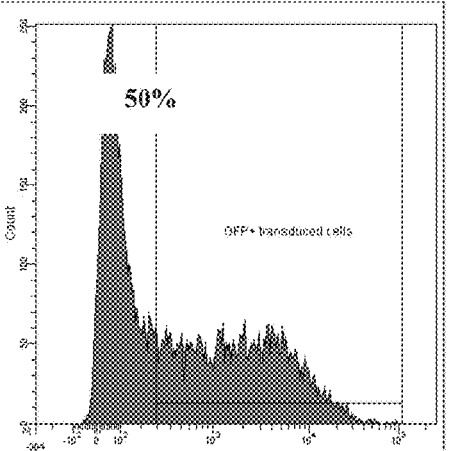
Figure 12C:
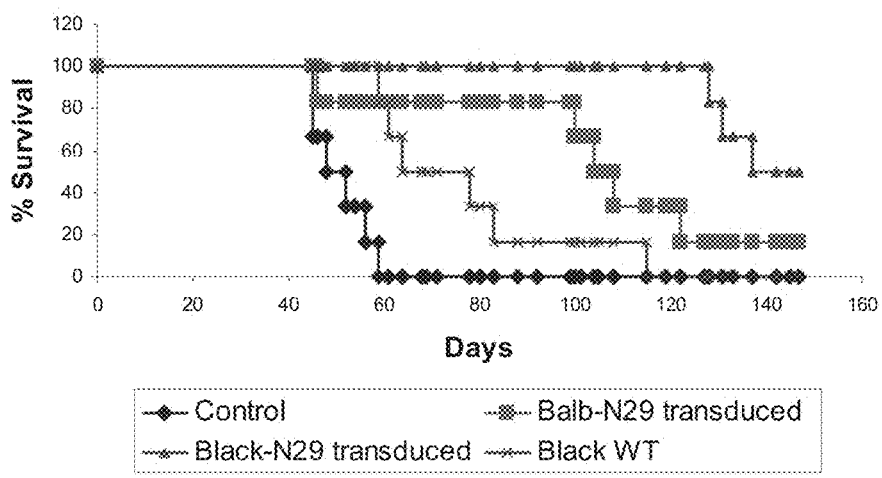
Figure 12D:
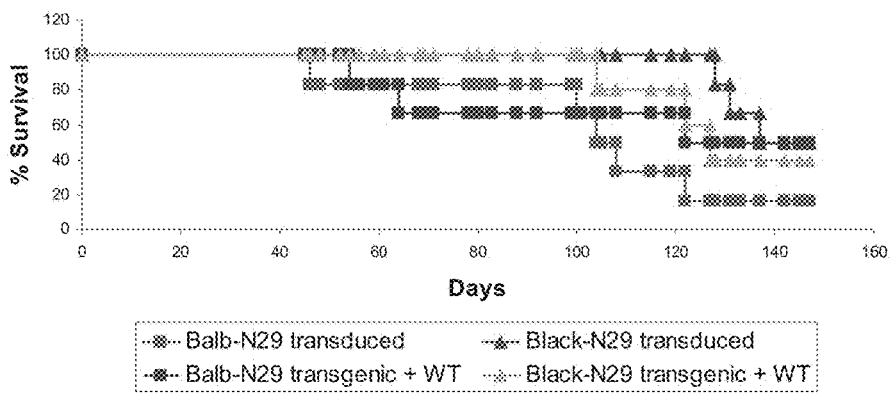

While T-bodies from transgenic animals are useful, they do not fully simulate a real world scenario in which T cells will have be transduced with the chimeric receptor. Therefore, the inventors repeated the 200/100 regimen, but this time instead of using transgenic T-bodies, they transduced wildtype C57Bl or Balb/c cells with retrovectors expressing the chimeric N29 receptor after activation (this time with the more clinically relevant CD3/CD28 antibodies rather than conA). Unlike transgenic cells which uniformly express the chimeric receptor, only 50% of transduced cells (both for Balb/c and C57Bl) express the chimeric receptor (FIG. 12A-B). While the results are still preliminary, they do suggest that C57Bl-N29 are as at least as effective as Balb-N29 (and maybe even more), and both are significantly more effective than untreated controls in accordance with our findings using transgenic T-bodies (FIG. 12C). In order to show that transgenic T-bodies function similarly to transduced T-bodies, the inventors performed a head to head comparison of the two treatments. In the same experiment, the inventors also included a group of mice which were treated with either syngeneic or allogeneic transgenic T-bodies. They injected the same number of T-bodies regardless of whether transgenic or transduced T-bodies were used. They added activated wildtype T cells of the same strain to the transgenic T-bodies such that all groups received the same number of T-bodies. Although the results are still preliminary transduced T-bodies performed similarly to transgenic T-bodies (results do not reach significance), demonstrating that transgenic and transduced T-bodies provide similar benefit (FIG. 12D).

Example 5

Figure 13A:
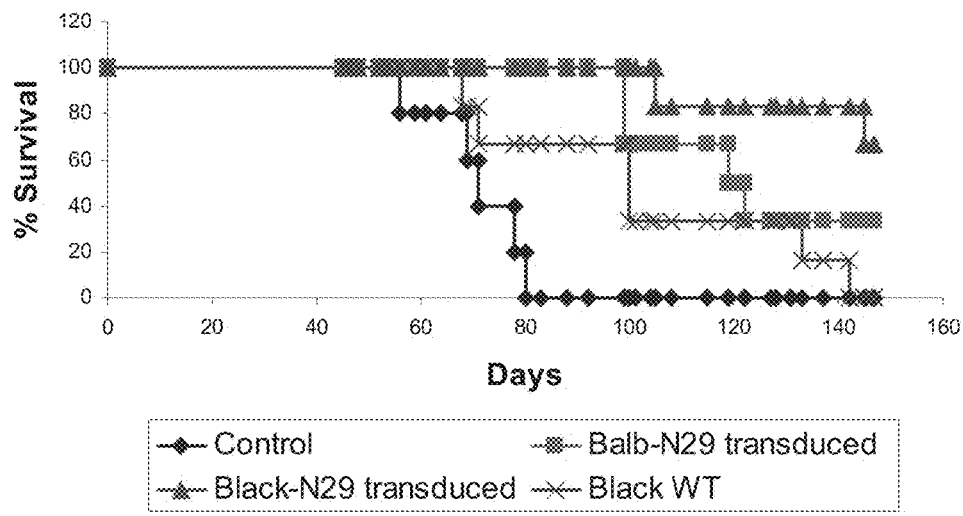
FIGS. 13A-13B: Cyclonhoshamide can replace TBI as preconditioning, and enables effective treatment at a lower cell dose. Balb/c mice (n=6) were inoculated (IV) with $10^5$ Renca-erbb2 cells, and injected with cyclophosphamide 200 mg/kg ip on day 7. Treated mice were injected with $10^7$ activated T cells (either transduced or not, allogeneic or syngeneic) on days 8 and 10. The same cells were used for these experiments and the experiments described in FIG. 10.
Figure 13B:
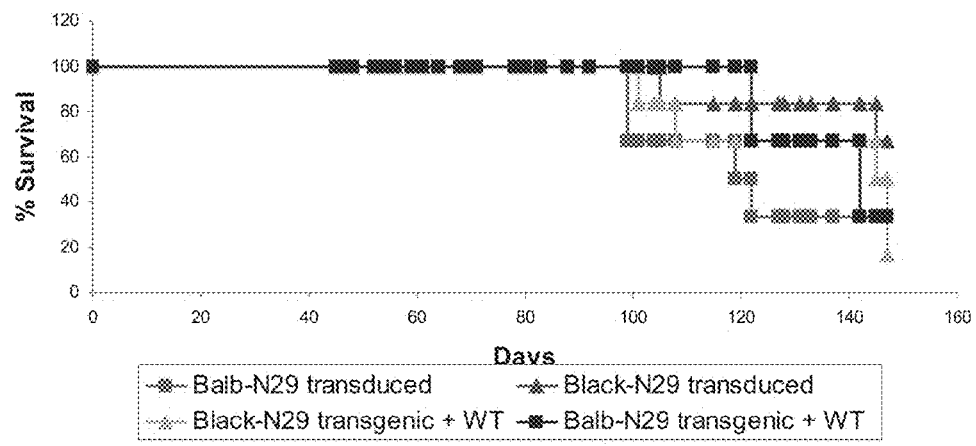

Cyclophosphamide can Replace Irradiation as the Preconditioning for the Adoptive Transfer and it Enables Effective Treatment with a Lower Cell Dose While total body irradiation (TBI) can be useful as preconditioning for the treatment, it is not the only way to lymphodeplete the host. Chemotherapy and depleting antibodies are also viable options for lymphodepletion. The reason for choosing irradiation in this model is because the Renca cell line is resistant to it, and therefore the therapeutic benefit is solely due to the immunotherapy rather than irradiation. In contrast previous experiments in our laboratory have shown that the Renca cell line is somewhat sensitive to chemotherapy, and specifically to cyclophosphamide. In a real world scenario, damage to the tumor is actually a desirable attribute of preconditioning. The inventors therefore sought to simulate a more clinically relevant situation, and replaced TBI with cyclophosphamide as a lymphodepleting treatment. When cyclophosphamide was injected at 200 mg/kg, followed by 100 million C57Bl cells there was 100% mortality due to lethal GvHD, the inventors therefore decided to use a smaller dose of 20 million cells which was completely safe (data not shown). Mice were injected with the tumor on day 1, cyclophosphamide (200 mg/kg) on day 7. Wildtype C57Bl and Balb/c T cells were transduced with the N29 chimeric receptor and injected 10 million cells on days 8 and 10. While results are still preliminary, there is a decided survival advantage for both allogeneic and syngeneic T-bodies over untreated mice (injected with cyclophosphamide only), with allogeneic T-bodies providing superior over syngeneic T-bodies (FIG. 13A). Wildtype C57/Bl T cells also provide therapeutic benefit, but not as much as allogeneic T-bodies, confirming that the response is indeed tumor specific and not allo-specific. The inventors also compared between transgenic and transduced T-bodies using this protocol, and again there was no significant difference between the T-bodies regardless whether they were syngeneic or allogeneic to the host (FIG. 12D). These results once again demonstrate that the efficacy of allogeneic adoptive transfer therapies depend both on the extent of lymphodepletion and the number of cells transferred, and that high cell number can compensate for low levels of lymphodepletion and vice versa. Importantly these results were achieved at a low cell dose (20 vs. 100 million) which is a more practical cell dose.

Example 6

Adoptive Transfer of Allogeneic Cells is Safe

While there was no mortality due to the 200/100 regimen it does not mean that the treatment did not cause damage to the host. In order to directly asses the effect of the treatment, mice were sacrificed mice during various time points and various organs were examined by histological analysis. The kinetics of weight loss (FIG. 6), during the treatment, suggest that the peak of the response occurs shortly after injection of cells (1-3 days later); therefore mice at 1 and 3 days after the $2^{nd}$ injection of cells were examined. One day after $2^{nd}$ injection there was no evidence of GvHD in the lungs, liver, intestine, or kidneys of the mice (FIGS. 14A-D). Three days after the $2^{nd}$ injection, a time point corresponding to the peak of the weight loss, lymphocyte infiltration into the lungs, liver, and intestine was observed, but not into the kidneys (FIGS. 14E-H). There were no signs of damage in any of the other tissues examined. Overall the evidence suggests that while lymphocytes do indeed infiltrate peripheral organs they do not cause them significant damage.

Example 7

Figure 15:
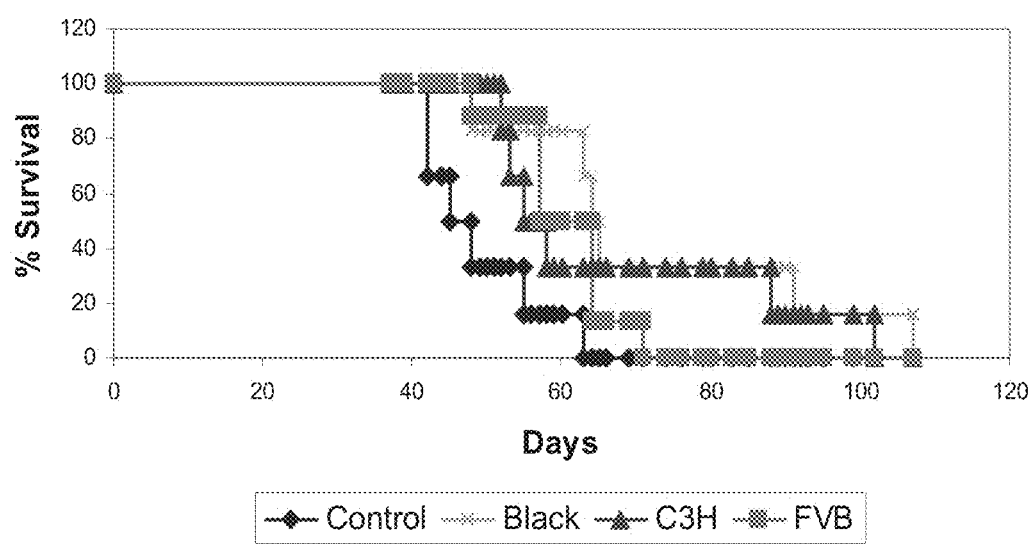
FIG. 15: Wild type cells from different strains can prolong survival of tumor bearing mice. Balb/b mice (n=6) were inoculated with $10^5$ Renca-erbb2 IV, and then irradiated with 200 rads 7 days later. On days 8 and 10, mice were injected with either C57Bl, C3H, or FVB activated T cells (50 million cells in each dose). C57Bl, C3H, and FVB all extend the survival of mice as compared to the control group (P<0.0004 for all groups compared with control group, but no significant difference between them).

Unmodified Allogeneic Cells from Different Mouse Strains Provide Similar Therapeutic Benefit Although wild type C57Bl allogeneic cells were less effective than C57Bl-N29 transgenic allogeneic cells in this tumor model, they still provided some benefit in the 200/100 regimen. The therapeutic efficacy of cells from 3 different strains (C57B1, FVB, and C3H) were compared (FIG. 15). All strains provided some therapeutic benefit extending the survival median to 64.5, 60.5, and 56.5 days for C57Bl, FVB, and C3H as compared with 43 days for the control groups ($P<0.0004$ for all groups compared with the control group, but no significant difference between the strains). The differences between strains are not surprising, reflecting allo-responses of varying strength between different strains combinations. Importantly, despite these differences all the strains provided significant (but modest) therapeutic benefit, highlighting the robustness of this approach. Unmodified allogeneic cells could potentially be used in cases in which no tumor specific antigen is known.

Example 8

Migration and Persistence of Adoptively Transferred Cells in vivo

Figure 17B:
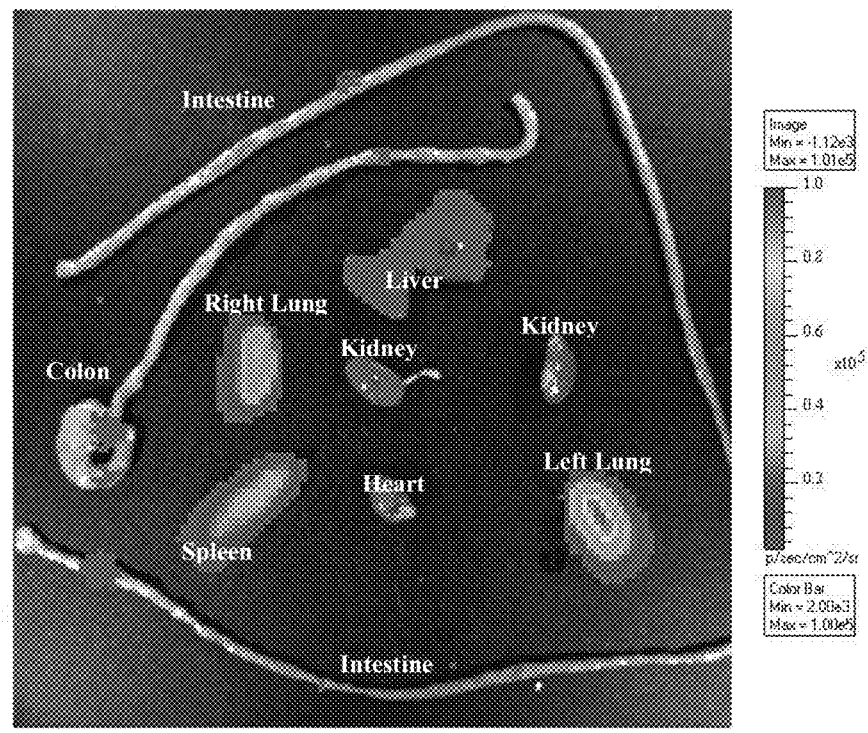
Figure 17C:
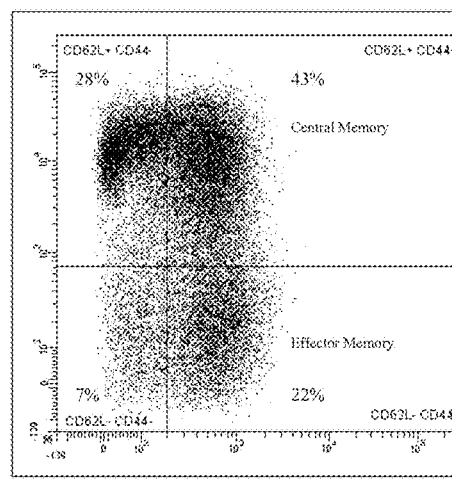

In order to elucidate the dynamics of allogeneic ACT, in vivo bioluminescence imaging was utilized to study the migration and persistence of Luciferase$^+$ T cells in ACT (FVB-Luc transgenic mice were kindly donated by Professor Reisner [40]). One day after irradiation with 200 rads, the inventors injected IV $10^8$ activated FVB-Luciferase$^+$ T cells (which do not express a chimeric receptor) into Balb/c bearing 7 day established Renca-erbB2 pulmonary metastases. Transferred cells could be detected throughout the body up to day 6, with peak emissions occurring at 3-4 days after the first injection, dropping 10 fold on days 5-6 (FIG. 16). Transferred cells were preferentially accumulated in the lymph nodes and abdominal region (probably reflecting mesenteric and inguinal lymph nodes), as measured by the 10 fold increase in photon emission from these areas as opposed to other tissues (FIG. 16). On days 5-6 most of the cells were detected in the lymph nodes, abdominal area, and the bone marrow; afterwards intermittent signals were detected only in the lymph nodes and the abdominal area until day 9 (FIG. 16). This data show that using this regimen, allogeneic cells survive for about 5-6 days in vivo, and are then rejected. While these T cells originate from a different strain than previous experiments (FVB vs. C57BL), they are nevertheless allogeneic to the Balb/c host (full MHC mismatch), and therefore their in vivo dynamics should closely resemble those of C57BL T cells. While their rejection limits their effectiveness in vivo, it also provides an important safety measure in that genetically manipulated cells do not persist in vivo for a long time. In order to precisely determine the localization of transferred cells, mice were sacrificed 1 day after adoptive transfer of 50 million FVB-Luc cells into Balb/c mice, and their organs were individually examined. The cells were detected in the lung, liver, spleen and lymph nodes (cervical and inguinal) of the recipient mice (FIGS. 17A-B), in accordance with the histology data (FIG. 14). This migration pattern is well suited for the treatment of metastatic disease, as the LN, lung and liver are the most common sites of metastatic spread. Migration to the lymph nodes was particularly interesting because it requires expression of lymph homing molecules which were reported to be down regulated after activation. Activated splenocytes that underwent the standard protocol (activation for 48 hours, followed by culturing in IL-2 for 5 days) were stained for expression of CD62L, and CD44. Rather unexpectedly, 30% of the T cells expressed a naïve (CD62L+, CD44$^{low}$) phenotype, 40% expressed a central memory (CD62L+, CD44$^{high}$) phenotype, and only 20% expressed the expected effector memory (CD62L−, CD44$^{high}$) phenotype (FIG. 17C). The high proportion of relatively undifferentiated cells might be the result of the short activation period we utilize (48 hours). Alternative protocols which lead to expansion of effector memory cells use extended propagation times (over one week) with continuous activation (either though the presence of peptide loaded APC or anti-CD3 beads).

Example 9

FTY720 can Ameliorate GvHD of Allo-T Bodies While Concurrently Potentiating the Antitumor Response GvHD occurs when donor cells overwhelm the host's immune system in the lymph nodes, and then proceed to attack peripheral tissues [13, 14]. FTY720 is an immunomodulating compound which traps T cells in the lymph nodes by preventing their egress into the blood, and it has been shown to extend survival of kidney allografts in clinical trials [19, 41]. It was hypothesized that trapping donor lymphocytes in lymphatic organs may also be an effective strategy to prevent GVHD as was recently confirmed in a few studies [42, 43]. Allogeneic adoptive therapy can potentially cause GVHD, and therefore could potentially benefit from the addition of FTY720. To study how this agents affects the allogeneic antitumor response and the GvH response, the inventors added 10 daily injections of FTY720 (following irradiation) to the 400/30 regimen which causes lethal GvHD when using wildtype C57Bl T cells. Addition of FTY720 significantly prevented GVHD mortality in this regimen: in the group treated with activated wild type C57Bl cells (2/6 mice died with FTY720 as compared with 5/6 without FTY720, FIG. 18A). Concurrently it not only preserved the antitumor efficacy in the C57Bl-N29 treated group, but significantly enhanced it from a median 11 days with no FTY720 to a median that was not reached in the treated group with 50% or more surviving after day 250, FIG. 18A). It is important to note that death from GvHD could be easily distinguished from death caused by the tumor. GvHD caused dramatic weight loss, as well as hunched posture, and was confirmed by liver cirrhosis post-mortem. All the mice that died before day 45 died of GvHD while all the mice that died after day 45 died because of the tumor without showing any signs of GvHD pre or post-mortem. The fact that addition of FTY720 improved survival in the allogeneic T-body group, even though there was no GvHD related deaths in this group even before addition of FTY720, prompted the inventors to test the effect of FTY720 on the 200/100 regimen (in which no GvHD occurs). In the 200/100 regimen FTY720 increased the therapeutic benefit provided by C57Bl-N29 (80% long term survivors with FTY720 vs. 50% long term survivors without FTY720, FIG. 18B), but not by Balb-N29, or wildtype C57Bl. In vivo imaging data demonstrate that FTY720 can indeed prolong the in vivo persistence of allogeneic T-bodies (FIG. 20). The fact that FTY720 selectively inhibited the GvH response but not the antitumor response, should encourage further studies of using FTY720 itself or similar agents to reduce GvH and maintain GvT responses using mis-matched T-cells for cancer immunotherapy.

Example 10

The experiments in this Example were conducted using the materials and methods described below.

Materials And Methods

Materials and cell lines. FTY720 was purchased from Caymen Chemicals (Ann Arbor, Mich.). Tumors were induced using the Renca cell line transduced with human Her2/neu kindly provided by Prof W. Wels (Chemotherapeutisches Forschungsinstitut Georg-Speyer-Haus).

Flow cytometry. Anti-mouse CD3ε (145-2C11)-Percp-Cy5.5, anti-mouse CD62L (MEL14)-PE-Cy7, and anti-mouse H-2 Kb (AF6-88.5)-Pacific Blue were purchased from Biolegend (San Diego, Calif.). PE-Annexin V, Streptavidin-APC, and Streptavidin-APC-Cy5.5 were purchased from eBioscience (San Diego, Calif.). Polyclonal antibody against the N29 CAR was generated in the present inventors' lab and then biotinylated.

Prior to splenocyte staining, RBC were lysed using ACK buffer. Lymphocytes ($1\times10^6$) were incubated with the appropriate antibodies in staining buffer (5% BSA, 0.05% sodium azide in phosphate-buffered saline (PBS)) for 30 minutes on ice. Alternatively, Annexin V staining buffer was used as indicated. CFSE (Carboxyfluorescein succinimidyl ester) labeling was performed according to the manufacturer's instructions (Molecular Probes. Eugene, Oreg.). Cells were analyzed by flow cytometry (LSRII, Becton Dickinson. Mountain View. Calif.) and FacsDiva software (Becton Dickinson).

Mice. Tumor bearing animals used in the experiments were generally 8-10 week old Balb/c mice. Donor splenocytes were obtained from 6-16 week old transgenic mice expressing the N29 CAR on either the C57BL/6 (allogeneic) or Balb/c (syngeneic) background. C57BL/6 and Balb/c luciferase transgenic mice (kindly received from Professor R. Negrin, ref. 70) were obtained by back-crossing FVB-Lucifease to these strains for at least 9 generations. Luciferase transgenic mice were then crossed to N29 transgenic mice, and F1 mice were used as donors in IVIS studies. All invasive procedures and imaging experiments were conducted under Ketamine and Xylazine general anesthesia (127.5 and 4.5 mg/kg, respectively). All animal studies were performed under protocols approved by the Weizmann Institute of Science Animal Use Committee.

Retroviral transduction of T cells. Retroviral transduction of T cells was performed as described previously (ref. 71). Briefly, activated T cells were transduced using spin-infection on RetroNectin (Takara, Japan) coated plates in the presence of vector-containing supernatant and IL-2.

Adoptive transfer experiments. Mice were injected with 105 Renca-Her2/neu cells iv on day 1. All mice (including the control group) were irradiated on day 7 with 200 or 400 rads (137Cs source). Prior to transfer, all T cells were activated with Con-A 1 μg/ml for 48 hours, and then cultured for 3-5 more days with 350 u/ml IL-2. Either 30×106 or 108 T cells were transferred in a split dose on days 8 and 10. In some experiments, FTY720 was injected ip (0.3 mg/kg) on days 8-18. Donor cells were either from wildtype mice (Balb/c or C57BL/6) or from N29 CAR transgenic mice (Balb/c or C57BL/6 backgrounds). In some cases, T-bodies from wild type mice (Balb/c or C57Bl) were transduced with the CAR.

In-vivo imaging. To follow trafficking of cells, the whole body cooled CCD camera system was used (IVIS® 100 Series Imaging System) from Xenogen (Hopkinton, Mass.). T-cells from C57BL/6-N29+/−/Luc+/− or Balb/c-N29+/−/Luc+/− mice were used in adoptive transfer. Luciferin was injected at 75 mg/kg, and images were acquired at low resolution with a 3-5 min exposure time. For ex-vivo analysis, mice were first injected with luciferin at 150 mg/kg. Quantification of average radiance was performed using Living Image software.

Statistical analysis. All results in this study were based on two-sided test statistics. Survival analysis was done using the log-rank test. P-values from independent experiments were combined using Fisher's method. Bioluminescence signals were compared using the Mann-Whitney test. FACS analysis was done using the chi-square test. $P<0.05$ was considered significant.

Results

Figure 21:
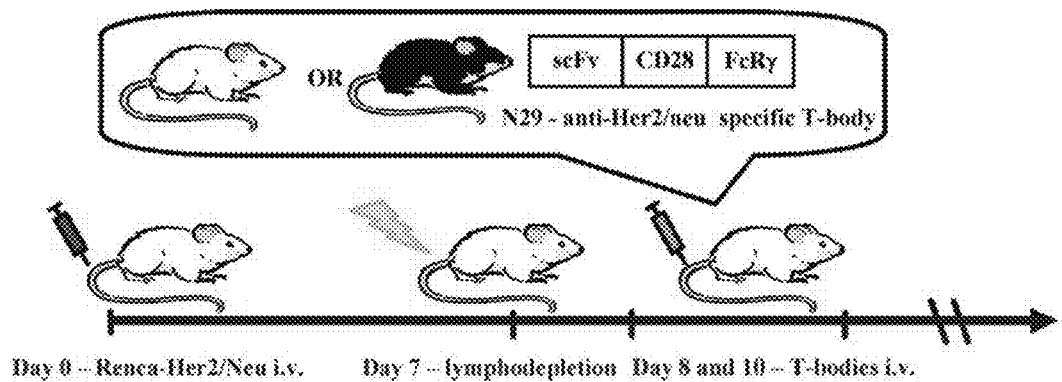
FIG. 21: Schematic illustration of the experimental setup. Mice were injected with $10^5$ Renca-Her2/Neu intravenously on day 0. On day 7, mice were irradiated with 200 or 400 rads total body irradiation (TBI). A split dose of T bodies (transduced with Her2/neu-specific CAR or isolated from transgenic mice expressing such CAR) was given on days 8 and 10. The chimeric antigen receptor (CAR) is composed of a scFv fused to CD28 and FcRγ signaling domains. T-bodies were either the C57BL/6 (allogeneic) or Balb/c (syngeneic) background.

Host's Preconditioning and Transferred Cell Dose Determines the Anti-Tumor Benefit To investigate the potential of allogeneic adoptive cell therapy, the BALB/c derived mouse renal cell carcinoma (Renca) cell line expressing the human Her2/neu was used. Following intravenous inoculation of the tumor, experimental metastases mainly developed in the lungs, yet, as was reported in similar systems (ref. 62, 63) extra-pulmonary metastases also developed. The tumor-bearing mice were lymphodepleted 7 days after tumor inoculation using sublethal irradiation (e.g., 200-400 rad, doses that did not affect tumor development). Adoptive transfer of T cells redirected with a Her2/neu-specific chimeric antigen receptor ('T-bodies') was performed on days 8 and 10 (FIG. 21). The CAR is composed of a scFv fragment derived from the Her2/Neu-specific N29 antibody fused to a CD28 co-activation moiety and FcRγ signaling sequences (ref. 8). This design of the CAR has been shown to be able to activate naïve T cells as well as to inhibit activation-induced death (AICD) (ref. 8). T-bodies were obtained from transgenic (Tg) mice of BALB/c (Balb-N29) or C57BL/6 (Black-N29) background, or by the transduction of wild type T cells with a retrovector harboring the Her2/neu-specific CAR. Transduced T cells were activated as part of their transduction, while naïve transgenic (Tg) T cells were also activated to facilitate comparison with transduced T cells.

Figure 22:
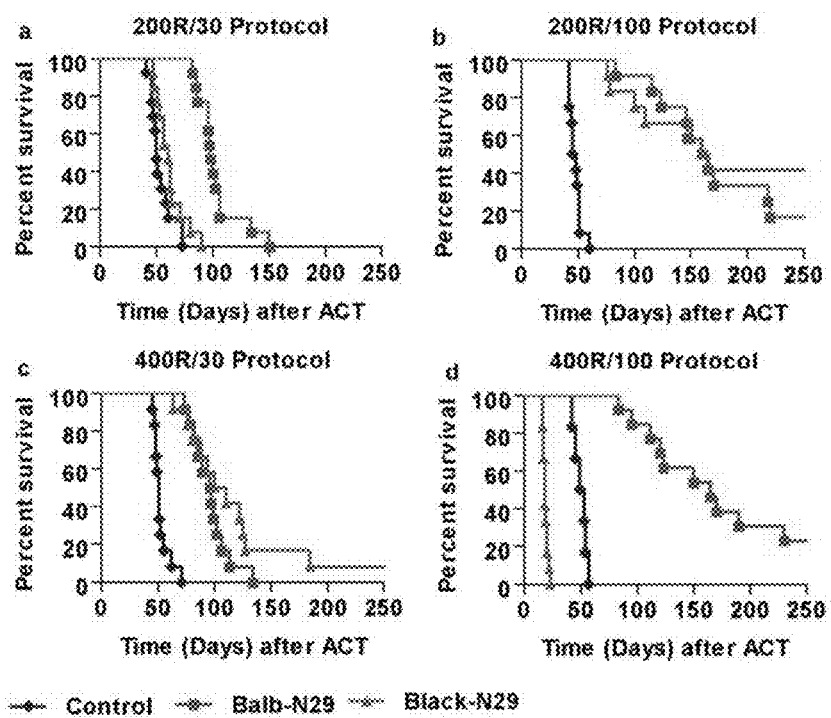
FIGS. 22a-22d: Balance between host's preconditioning and transferred cell dose determines the anti-tumor benefit provided by allogeneic T-bodies. Kaplan-Meyer survival plots of Renca-Her2/Neu-bearing mice. Mice (n=12/group) were irradiated and then either left untreated as a control (diamonds), or systemically administered with syngeneic T-bodies (Balb-N29, squares) or allogeneic T-bodies (Black-N29, triangles). The results shown are pooled from two independent experiments. P-values were computed for each experiment separately using the log-rank test, and combined using Fisher's method.

An adoptive transfer protocol consisting of irradiation with 200 rads followed by transfer with 30×106 syngeneic transgenic T cells (Balb-N29) extended the median survival of tumor bearing mice to 97 days, as compared with 50 days for the control group which was also irradiated (P=0.000004, FIG. 22a), yet no complete cure of tumor-bearing mice was achieved. Using this protocol with allogeneic T-bodies (Black-N29) provided no survival advantage (FIG. 22a). The present inventors postulated that under these conditions the host-versus-graft (HvG) reaction was dominant, leading to rapid rejection of the allogeneic T-bodies. With an increased cell dose (200 rad and 100×106 T-bodies) allo-T-bodies extended median survival comparably to syngeneic T-bodies (162.5 and 160 days respectively) as compared with only 46.5 days for the control group (P=0.000004 for both allogeneic and syngeneic T-bodies vs. control, FIG. 22b). Reducing graft rejection by increasing lymphodepletion (400 rads) and using the lower cell dose (30×106) increased median survival of tumor bearing mice treated with allogeneic T-bodies to 105 days, similarly to syngeneic T-bodies (median of 95 days) and more than the 50 day median of the control group (P=0.000004 for both allogeneic and syngeneic T-bodies vs. control, FIG. 22c). Importantly, no GvHD associated mortality occurred using either of the protocols, demonstrating that an allogeneic T-body response can provide therapeutic benefit without significant toxicity to the host. However increasing both the cell dose and the irradiation dose (400 rads and 100×106 T-bodies) caused lethal GvHD (which was preceded by weight loss and lymphoid hypoplasia—data not shown) in all mice receiving allo-T-bodies (FIG. 22d).

Both CAR and TCR-Based Allo-Reactivity Augment the Anti-Tumor Response

Figure 23:
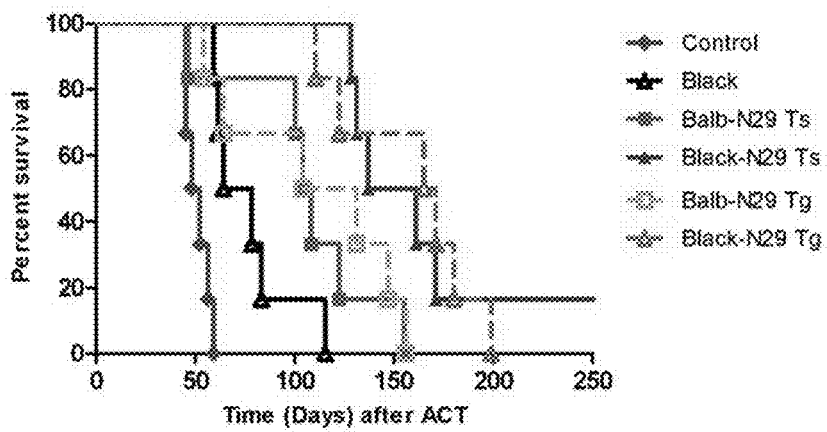
FIG. 23, Both the antibody based chimeric receptor and TCR-based alloreactivity augment the anti-tumor response. Kaplan-Meyer survival plots of Renca-Her2/Neu-bearing mice. Mice (n=6/group) were irradiated with 200 rads and 1 day later either left untreated as a control (diamond), or injected with $100 \times 10^6$ T cells. The T cell populations used were either: allogeneic mock transduced T cells (Black, empty black triangles. P-0.0011 vs. control), syngeneic T cells transduced with the N29 CAR (Balb-N29 Ts, filled squares), allogeneic T cells transduced with the N29 CAR (Black-N29 Ts, filled triangles, P=0.0005 vs. Black, P=0.012 vs. Balb-N29), syngeneic T cells from N29 transgenic Balb/c mice (Balb-N29 Tg, open squares, no significant difference was seen versus transduced cells), allogeneic T cells from N29 transgenic C57BL/6 mice (C57BL-N29 Tg, open triangles, no significant difference was seen versus transduced cells)

To evaluate the contribution of CAR to the allogeneic T-body response under realistic conditions, wild-type BALB/c and C57BL6 T cells were transduced (typically with 50% transduction efficiency) with the N29 CAR and their anti-tumor response was compared to mock transduced C57BL/6 T cells in Renca-Her2/neu tumor bearing mice. Mock transduced allogeneic T cells were able to extend the median survival of tumor bearing mice to 71 days as compared with only 50 days for the control group (P=0.001 for allogeneic T cells vs. control, FIG. 23) demonstrating that non-specific allogeneic T cells can provide some therapeutic benefit on their own. Nevertheless, allo-T-bodies were more effective than mock transduced allogeneic T cells, and were able to extend median survival to 150 days (P=0.0005 allogeneic T-bodies vs. non-redirected allogeneic T cells, FIG. 23); thus, redirection through the CAR potentiates allogeneic therapy. Allogeneic T-bodies were also superior to syngeneic T-bodies, which extended median survival to only 106 days (P=0.012 for allogeneic T-bodies vs. syngeneic T-bodies, FIG. 23). In the same experiment, we compared transduced T-bodies to transgenic T-bodies. Equal numbers of Tg T-bodies were transferred with addition of T cells from the wild type strain in order simulate the 50% transduction efficiency of transduced T-bodies. There was no significant difference between the survival benefit of transduced versus transgenic T-bodies (FIG. 23). These data directly demonstrate that addition of non-redirected allogeneic T cells can potentiate allogeneic ACT.

Allo-Reactivity Modulates the Migration and Persistence of Allogeneic Cells

In order to understand the dynamics of the T-body response under the conditions described above, luciferase+ T-bodies (obtained from crossing N29-Tg mice to Luciferase-Tg mice from the same background) were transferred to Renca-Her2/neu-bearing mice and the labeled cells were monitored using the in vivo imaging system (IVIS). Changing the transferred cell number and radiation dose of the host did not significantly alter the migration or persistence of syngeneic T-bodies (FIG. 24a), but had a striking effect on allo-T-bodies (FIG. 24a). At the lowest cell and radiation doses (200 rads and 30×106 cells) allogeneic T-bodies could not be detected, suggesting they were rapidly rejected (FIG. 24a). At a higher cell dose (200 rads and 100×106 cells), 1 day after transfer, the whole-body bioluminescent (BLI) signal from allo-T-bodies was higher than that of syngencic T-bodies (P=0.005, FIG. 24b). However, the allogeneic cell signal decayed until it became undetectable 7 days after cell transfer, in contrast to the syngeneic signal which persisted for the duration of the observation period (20 days). These data demonstrate the partial dominance of the HvG response after irradiation with 200 rads. In contrast, inhibiting the HvG further by increasing the radiation dose to 400 rads (while keeping the cell dose constant at 30×106) changed the dynamics of the response to a bell-shaped one (FIGS. 24a-b). During the first week, the BLI signal from the allogeneic cells increased, followed by gradual decline reflecting HvG-mediated clearance (FIG. 24a). Using this protocol, the signal from the allogeneic cells was stronger than the syngeneic signal on day 7 (P=0.005, FIG. 24b) and weaker by day 14 (P=0.002, FIG. 24b). As expected, increased lymphodepletion (using a higher irradiation dose) allowed allogeneic T-bodies to persist longer in vivo (FIG. 24a-b). The transient persistence of allo-T-bodies using either protocol explains the absence of serious GvHD related toxicity under these conditions. The dynamics of the allogeneic cells suggested that they underwent GvH-driven proliferation. In order to verify this, the experiment was repeated but using luciferase+ T cells instead, labeled with CFSE; staining with an anti-idiotypic antibody to the CAR allowed identification of the transferred T-bodies. FACS analysis of splenocytes on day 4 after transfer demonstrated that a subset of the allogeneic but not syngeneic T-bodies underwent extensive proliferation (FIG. 24c). Furthermore, this proliferation was associated with loss of CD62L expression (P=0.0001, FIG. 24d) in splenic T cells, indicating that the T cells differentiated to effector memory cells.

FTY720 Augments Allogeneic but not Syngeneic Adoptive Therapy

Figure 25:
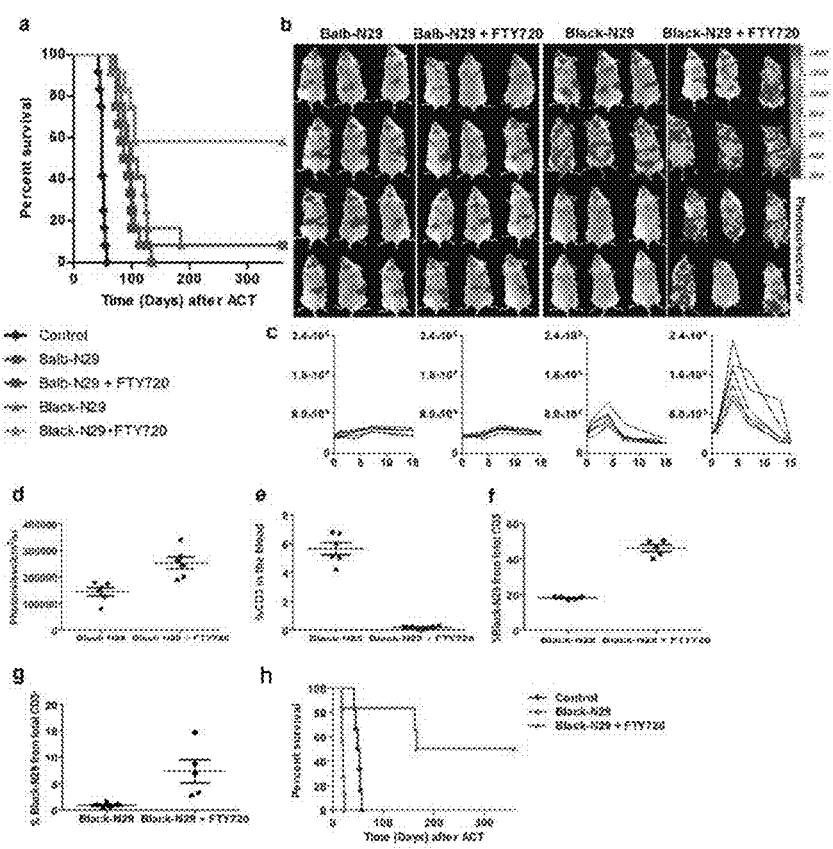
FIGS. 25a-25h. FTY720 augments allogeneic but not syngeneic adoptive therapy.

The inventors next sought to determine whether modulating lymphocyte migration through the use of FTY720 can augment the therapeutic benefit of T bodies. First, adding FTY720 to the treatment protocol for a short time (0.3 mg/kg i.p for the first 10 days after irradiation) was shown not to affect the survival of tumor bearing mice (data not shown). The effect of FTY720 on the adoptive transfer of both syngeneic and allogeneic T-bodies (400 rads and 30×106 T-bodies) was then checked. While FTY720 did not have any notable effect on syngeneic T-body therapy (median survival of 95 days without FTY720 as opposed to 90 days with FTY720, FIG. 25a), it had a profound effect on allo-T-body therapy, with 58% mice surviving long term (>350 days) with FTY720, as opposed to only 8% without it (P=0.013, FIG. 25a). At the end of the observation period (>350 days) all mice were autopsied and found to be tumor free. To investigate the mechanism of action of FTY720, its effect on luciferase+ T-bodies in tumor bearing mice was tested. In agreement with the survival data, FTY720 did not seem to significantly alter the migration or the persistence of syngeneic T-bodies (FIG. 25b). However, FTY720 did impact the allogeneic immune response, such that the BLI signal from these mice was higher, especially from the lymphatic organs, and persisted for a longer time (FIGS. 25b-d).

These data were confirmed by FACS analysis showing that FTY720 inhibited lymphocyte egression to the blood (FIG. 25e), thereby causing increased accumulation in the lymphatic organs (FIG. 25f). In addition, FACS analysis also confirmed that FTY720 enhanced the persistence of allogeneic T cells in vivo, with higher numbers of allo-T-bodies detected in the spleen on day 7 (FIG. 25g). This enhanced persistence of allogeneic T-bodies can explain the increased survival of tumor bearing mice treated with allogeneic T-bodies and FTY720.

When the effect of FTY720 was tested in a protocol which generally causes lethal GvHD (manifested by severe cachexia) in 100% of mice (400 rads and 108 allo-T-bodies, FIG. 22d), only 16% of the mice died of GvHD (FIG. 25h, P=0.005). In addition, most of the remaining mice survived long term (>350 days), demonstrating that FTY720 can concurrently inhibit GvHD while allowing the anti-tumor response to proceed.

Discussion

Figure 24:
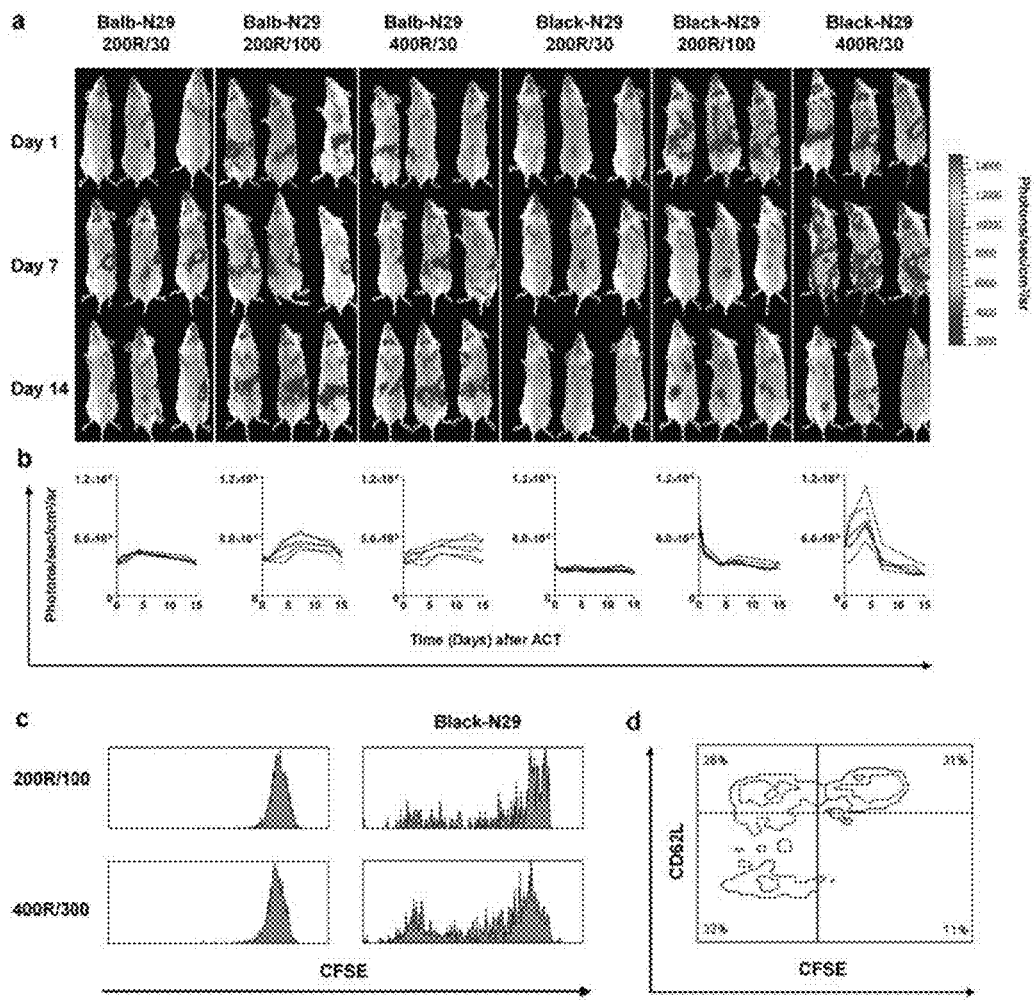
FIGS. 24a-24d. Alloreactivity modulates the migration and persistence of allogeneic cells.

In this study, the use of genetically redirected open repertoire allogeneic T cells was demonstrated to be a safe and effective alternative to syngeneic T cells of disseminated tumor. Despite only transient persistence in sub-lethally irradiated mice, allo-T-bodies provided as much therapeutic benefit as syngeneic cells, when sufficient numbers of T-bodies were transferred, and were not accompanied by lethal GvHD (FIG. 22b-c). Allo-T-bodies were superior to non-redirected allogeneic T cells, highlighting the importance and the potency of the CAR (FIG. 23). The GvH reactivity of the allogeneic T cells modulated the immune response causing these cells to proliferate extensively and differentiate to effector cells (FIG. 24). When lymphocyte egress was inhibited through the addition of FTY720 to the treatment protocol, allo-T-bodies provided long lasting therapeutic benefit, in contrast to syngeneic cells (FIG. 25a).

The outcome of the T-body response depends on the dual specificities of the T-body—the CAR and the endogenous TCR. The balance between anti-tumor activity and anti-host activity determined the success of this modality. Importantly, all T-bodies can recognize the tumor, but only a fraction of the allo-T-bodies have GvH reactivity (FIG. 24). In addition, the incorporation of the CD28 signaling moiety into the CAR has been shown to activate bc1-xL, thereby reducing CAR-associated AICD, compared with the endogenous TCR (ref. 8). Improvements to the CAR such as the incorporation of additional co-stimulatory moieties (for example 4-1BB, refs. 10, 61) may further increase the potency and persistence the allo-T-bodies, thus enhancing the graft versus tumor (GvT) response without increasing the risk of GvHD.

The risk of GvHD limits the number of allo-T-bodies which could be transferred safely, but the inherent GvH reactivity of these cells could also potentiate ACT. The GvH reactivity stimulated allo-T-bodies in vivo, and caused substantial proliferation (FIG. 24) in the absence of vaccination or high dose IL-2. GvH-driven proliferation is one possible explanation why allo-T-bodies were able to provide similar therapeutic benefit to that of syngeneic ones (FIG. 22b-c) despite limited persistence (FIG. 24). However, in vivo stimulation may potentiate ACT through mechanisms other than enhanced proliferation. In a recent study, Pule et al showed that autologous GD2-specific T-bodies derived from anti-EBV CTL persisted for a longer time than T-bodies derived from polyclonal T cells in patients latently infected with EBV, demonstrating the contribution of in vivo antigenic stimulation to persistence (ref. 12).

There have only been a small number of studies on the use of allogeneic cells without allogeneic HCT. One such study, which was conducted by Boni et al. compared the anti-tumor activity of either syngeneic or allogeneic haploidentical naïve TCR transgenic T cells expressing the pmel TCR in a model of experimental melanoma (ref. 30). The authors showed that the pmel TCR did not possess allo-reactivity against the other mouse strains which were tested (ref. 30).

Myeloablative irradiation of the mice at (900 rads) delayed the rejection of allogeneic T cells which were able to cause regression of established tumors. Nevertheless, allogeneic T cells were inferior to syngeneic T cells in causing tumor regression presumably because the allogeneic were eventually rejected. Addition of allogeneic open repertoire T cells to the pmel T cells increased tumor regression, demonstrating that allo-reactivity can enhance the anti-tumor response similarly to the results in the present study (FIG. 23). However, the improvement seen in Boni's study came at the cost of lethal GvHD while in the present study, using milder irradiation doses, no GvHD developed. This contribution of allo-reactivity to the anti-tumor response can also help explain why in the present study allogeneic T cells provided comparable benefit to syngeneic T cells.

The present inventors' strategy for allogeneic ACT hinged on exploiting the GvH response to augment therapy. However, this approach can also benefit from reducing the frequency of allo-reactive T cells, which may allow transfer of more allogeneic T cells, or from increased irradiation prior to transfer, thus maintaining the GvH response at a safe level, while increasing the potency of the ACT protocol. One way to reduce the frequency of allo-reactive T cells is to use antigen-specific T cells which have a restricted TCR repertoire instead of open repertoire T cells, similarly to the cells used by Boni et al (ref. 30). In fact, these two approaches are not mutually exclusive since antigen-specific T cells can be transduced with an additional specificity, to express a tumor-specific CAR. While the clinical experience with allogeneic tumor-specific T cells has been very limited, allogeneic virus-specific T cell lines have been frequently used following allogeneic HCT to treat viral reactivation, usually without causing serious GvHD (refs. 24, 64, 65). Interestingly, it has recently been demonstrated that even though they generally do not cause GvHD, many virus-specific lines possess allo-reactivity (refs. 66-68). These findings suggest that combining T-bodies and antigen-specific T cells is a promising approach for allogeneic ACT. Translation of this approach to patients will require incorporation of additional safety measures to deal with the risk of GvHD; one possible approach is the expression of suicide genes by the allo-T-bodies (refs. 55, 69).

Addition of FTY720 to the treatment protocol increased the percentage of long term (>350 days) surviving mice treated with allogeneic but not syngeneic T-bodies, such that allo-T-bodies provided superior therapeutic benefit over syngeneic ones (FIG. 25a). The superiority of allo-T-bodies proves that their allo-reactivity can be exploited to potentiate ACT. As expected. FTY720 blocked egress of lymphocytes to the blood, thereby supporting increased accumulation in the lymphatic organs (FIG. 25d-f). One possible explanation for how FTY720 boosts therapeutic benefit is that by sequestering host lymphocytes in the lymphatic organs, the HvG response is inhibited, and allo-T-bodies already in peripheral organs in the vicinity of the tumor are rejected more slowly. Another possibility is that the GvH-reactive allo-T-bodies trapped in the lymphatic organs attack the host's immune system, weakening it, thereby delaying rejection of allo-T-bodies outside the lymphatic organs. Importantly, when FTY720 was added to a protocol which causes lethal GvHD, it inhibited GvHD without ablating therapeutic benefit; thus, addition of FTY720 was beneficial to allogeneic ACT whether or not the protocol caused GvHD. However, blocking egress can also potentially inhibit the efficacy of immunotherapy, especially when vaccination is employed and effector cells are generated in the LN. By virtue of their CAR, T-bodies can be activated by cells in peripheral tissues which do not express co-stimulatory molecules (ref. 8) and are therefore less dependent on stimulation by APCs in the LN.

The lymph nodes are one of the most common metastatic sites for virtually all cancers (solid as well as hematological) and transfer of allo-T-bodies holds particular promise for this issue. The GvH-driven proliferation of allo-T-bodies can potentially allow for extremely powerful responses against LN metastases. Administration of FTY720 in conjunction with allo-T-body transfers can further augment such responses by blocking lymphocyte egress and concentrating the anti-tumor response to the lymph nodes.

Taken together, the results in the present study provide a proof of principle for the application of allogeneic adoptive therapy, which is both safe and effective in the present inventors' mouse model using fully mismatched allogeneic open repertoire T cells redirected by a tumor-specific CAR. The combination of MHC-mismatched allogeneic T cells with an MHC unrestricted chimeric antigen receptor yields 'universal effector cells' which could potentially be used as an 'off-the-shelf' cellular therapy for cancer. Inhibition of lymphocyte egression augmented allogeneic adoptive therapy such that allogeneic T-bodies provided greater therapeutic benefit than syngeneic T-bodies despite their limited persistence. These results suggest that with further fine-tuning, allogeneic adoptive therapy may become the treatment of choice both because of its obvious logistical and economical advantages, and due to its greater efficacy.

CITED REFERENCES

1 Rosenberg. S. A., N. P. Restifo, J. C. Yang, R. A. Morgan, and M. E. Dudley, *Adoptive cell transfer: a clinical path to effective cancer immunotherapy*. Nat Rev Cancer, 2008. 8(4): p. 299-308.
2 Gattinoni, L., D. J. Powell, Jr., S. A. Rosenberg, and N. P. Restifo, *Adoptive immunotherapy for cancer: building on success*. Nat Rev Immunol, 2006. 6(5): p. 383-93.
3 Gattinoni, L., S. E. Finkelstein, C. A. Klebanoff, P. A. Antony, D. C. Palmer. P. J. Spiess, L. N. Hwang, Z. Yu, C. Wrzesinski, D. M. Heimann, C. D. Surh, S. A. Rosenberg, and N. P. Restifo, *Removal of homeostatic cytokine sinks by lymphodepletion enhances the efficacy of adoptively transferred tumor-specific CD8+ T cells*. J Exp Med, 2005. 202(7): p. 907-12.
4 Muranski. P., A. Boni, C. Wrzesinski, D. E. Citrin, S. A. Rosenberg, R. Childs, and N. P. Restifo, *Increased intensity lymphodepletion and adoptive immunotherapy—how far can we go?* Nat Clin Pract Oncol. 2006. 3(12): p. 668-81.
5 Sadelain, M., R. Brentjens, and I. Riviere, *The promise and potential pitfalls of chimeric antigen receptors*. Curr Opin Immunol, 2009. 21(2): p. 215-23.
6 Varela-Rohena, A., C. Carpenito, E. E. Perez, M. Richardson, R. V. Parry, M. Milone, J. Scholler, X. Hao, A. Mexas, R. G. Carroll, C. H. June, and J. L. Riley, *Genetic engineering of T cells for adoptive immunotherapy*. Immunol Res, 2008. 42(1-3): p. 166-81.
7 Dudley, M. E., J. R. Wunderlich, P. F. Robbins, J. C. Yang, P. Hwu. D. J. Schwartzentruber, S. L. Topalian, R. Sherry. N. P. Restifo, A. M. Hubicki, M. R. Robinson, M. Raffeld, P. Duray. C. A. Seipp, L. Rogers-Freezer, K. E. Morton, S. A. Mavroukakis, D. E. White, and S. A. Rosenberg, *Cancer regression and autoimmunity in patients after clonal repopulation with antitumor lymphocytes*. Science, 2002. 298(5594): p. 850-4.

8 Friedmann-Morvinski, D., A. Bendavid, T. Waks. D. Schindler, and Z. Eshhar, *Redirected primary T cells harboring a chimeric receptor require costimulation for their antigen-specific activation.* Blood, 2005. 105(8): p. 3087-93.

9 Eshhar, Z., T. Waks, G. Gross, and D. G. Schindler, *Specific activation and targeting of cytotoxic lymphocytes through chimeric single chains consisting of antibody-binding domains and the gamma or zeta subunits of the immunoglobulin and T-cell receptors.* Proc Natl Acad Sci USA. 1993. 90(2): p. 720-4.

10 Dotti, G., B. Savoldo, and M. Brenner, *Fifteen Years of Gene Therapy Based on Chimeric Antigen Receptors: "Are We Nearly There Yet?"* Hum Gene Ther, 2009 20:1229-39

11 June, C. H., *Adoptive T cell therapy for cancer in the clinic.* J Clin Invest, 2007. 117(6): p. 1466-76.

12 Pule, M. A., B. Savoldo, G. D. Myers, C. Rossig, H. V. Russell, G. Dotti, M. H. Huls, E. Liu. A. P. Gee, Z. Mei, E. Yvon, H. L. Weiss, H. Liu, C. M. Rooney, H. E. Heslop, and M. K. Brenner, *Virus-specific T cells engineered to coexpress tumor-specific receptors: persistence and antitumor activity in individuals with neuroblastoma.* Nat Med, 2008. 14(11): p. 1264-70.

13 Copelan. E. A., *Hematopoietic stem-cell transplantation.* N Engl J Med, 2006. 354(17): p. 1813-26.

14 Welniak, L. A., B. R. Blazar, and W. J. Murphy. *Immunobiology of allogeneic hematopoietic stem cell transplantation.* Annu Rev Immunol, 2007. 25: p. 139-70.

15 Terasaki, P. I., *Humoral theory of ransplantation.* Am J Transplant, 2003. 3(6): p. 665-73.

16 Milland, J. and M. S. Sandrin, *ABO blood group and related antigens, natural antibodies and transplantation.* Tissue Antigens, 2006. 68(6): p. 459-66.

17 Karre, K., *Natural killer cell recognition of missing self.* Nat Immunol, 2008. 9(5): p. 477-80.

18 Beilhack, A., S. Schulz, J. Baker, G. F. Beilhack, R. Nishimura, E. M. Baker, G. Landan, E. I. Herman, E. C. Butcher, C. H. Contag, and R. S. Negrin, *Prevention of acute graft-versus-host disease by blocking T-cell entry to secondary lymphoid organs.* Blood. 2008. 111(5): p. 2919-28.

19 Cyster, J. G., *Chemokines, sphingosine-1-phosphate, and cell migration in secondary lymphoid organs.* Annu Rev Immunol, 2005. 23: p. 127-59.

20 Klebanoff, C. A., L. Gattinoni. P. Torabi-Parizi, K. Kerstann, A. R. Cardones, S. E. Finkelstein, D. C. Palmer, P. A. Antony. S. T. Hwang, S. A. Rosenberg, T. A. Waldmann, and N. P. Restifo, *Central memory self/tumor-reactive CD8+ T cells confer superior antitumor immunity compared with effector memory T cells.* Proc Natl Acad Sci USA, 2005. 102(27): p. 9571-6.

21 Lanzavecchia, A. and F. Sallusto, *Understanding the generation and function of memory T cell subsets.* Curr Opin Immunol, 2005. 17(3): p. 326-32.

22 Sallusto, F., J. Geginat, and A. Lanzavecchia, *Central memory and effector memory T cell subsets: function, generation, and maintenance.* Annu Rev Immunol, 2004. 22: p. 745-63.

23 Zheng, H. C. Matte-Martone, D. Jain, J. McNiff, and W. D. Shlomchik, *Central memory CD8+ T cells induce graft-versus-host disease and mediate graft-versus-leukemia.* J Immunol, 2009. 182(10): p. 5938-48.

24 Dazzi, F. and J. M. Goldman, *Adoptive immunotherapy following allogeneic bone marrow transplantation.* Annu Rev Med. 1998. 49: p. 329-40.

25 Tomblyn, M. and H. M. Lazarus. *Donor lymphocyte infusions: the long and winding road: how should it be traveled?* Bone Marrow Transplant, 2008. 42(9): p. 569-79.

26 Kolb, H. J., J. Mittermuller, C. Clemm, E. Holler, G. Ledderose, G. Brehm, M. Heim, and W. Wilmanns, *Donor leukocyte transfusions for treatment of recurrent chronic myelogenous leukemia in marrow transplant patients.* Blood, 1990. 76(12): p. 2462-5.

27 Baker, J., M. R. Verneris, M. Ito. J. A. Shizuru, and R. S. Negrin, *Expansion of cytolytic CD8(+) natural killer T cells with limited capacity for graft-versus-host disease induction due to interferon gamma production.* Blood: (10)97. 2001, p. 2923-31.

28 Nishimura, R., J. Baker, A. Beilhack, R. Zeiser, J. A. Olson, E. I. Sega, M. Karimi, and R. S. Negrin, *In vivo trafficking and survival of cytokine-induced killer cells resulting in minimal GVHD with retention of antitumor activity.* Blood, 2008. 112(6): p. 2563-74.

29 Verneris, M. R., M. Karami, J. Baker, A. Jayaswal, and R. S. Negrin, *Role of NKG2D signaling in the cytotoxicity of activated and expanded CD8+ T cells.* Blood, 2004. 103(8): p. 3065-72.

30 Boni, A., P. Muranski, L. Cassard, C. Wrzesinski, C. M. Paulos, D. C. Palmer, L. Gattinoni, C. S. Hinrichs, C. C. Chan, S. A. Rosenberg, and N. P. Restifo, *Adoptive transfer of allogeneic tumor-specific T cells mediates effective regression of large tumors across major histocompatibility barriers.* Blood, 2008. 112(12): p. 4746-54.

31 Zakrzewski, J. L., D. Suh, J. C. Markley, O. M. Smith, C. King, G. L. Goldberg. R. Jenq, A. M. Holland, J. Grubin, J. Cabrera-Perez, R. J. Brentjens, S. X. Lu, G. Rizzuto, D. B. Sant'Angelo, I. Riviere, M. Sadelain, G. Heller, J. C. Zuniga-Pflucker, C. Lu, and M. R. van den Brink, *Tumor immunotherapy across MHC barriers using allogeneic T-cell precursors.* Nat Biotechnol, 2008. 26(4): p. 453-61.

32 Van Kaer, L. *Accessory proteins that control the assembly of MHC molecules with peptides.* Immunol Res, 2001. 23(2-3): p. 205-14.

33 Sambrook. J. G. and S. Beck, *Evolutionary vignettes of natural killer cell receptors.* Curr Opin Immunol, 2007. 19(5): p. 553-60.

34 Lanier, L. L., *Natural killer cells fertile with receptors for HLA-G?* Proc Natl Acad Sci USA, 1999. 96(10): p. 5343-5.

35 Rudd, C. E. and H. Schneider, *Unifying concepts in CD28, ICOS and CTLA4 co-receptor signalling.* Nat Rev Immunol, 2003. 3(7): p. 544-56.

36 Grohmann, U., C. Orabona, F. Fallarino, C. Vacca, F. Calcinaro, A. Falorni, P. Candeloro, M. L. Belladonna, R. Bianchi, M. C. Fioretti, and P. Puccetti, *CTLA-4-Ig regulates tryptophan catabolism in vivo.* Nat. Immunol. 2002. 3(11): p. 1097-101.

37 Taylor, P. A., C. J. Lees, S. Fournier, J. P. Allison, A. H. Sharpe, and B. R. Blazar, *B7 expression on T cells down-regulates immune responses through CTLA-4 ligation via T-T interactions [corrections].* J Immunol, 2004. 172(1): p. 34-9.

38 Leung, H. T., J. Bradshaw, J. S. Cleaveland, and P. S. Linsley, *Cytotoxic T lmphocyte-associated molecule-4, a high-avidity receptor for CD80 and CD86, contains an intracellular localization motif in its cytoplasmic tail.* J Biol Chem, 1995. 270(42): p. 25107-14.

39 Lundqvist, A., J. P. McCoy, L. Samsel, and R. Childs, *Reduction of GVHD and enhanced antitumor effects after* adoptive infusion of alloreactive Ly49-mismatched NK cells from MHC-matched donors. Blood, 2007. 109(8): p. 3603-6.

40 Cao, Y. A., A. J. Wagers. A. Beilhack, J. Dusich. M. H. Bachmann, R. S. Negrin, I. L. Weissman, and C. H. Contag, *Shifting foci of hematopoiesis during reconstitution from single stem cells*. Proc Natl Acad Sci USA, 2004. 101(1): p. 221-6.

41 Matloubian, M., C. G. Lo, G. Cinamon, M. J. Lesneski, Y. Xu. V. Brinkmann, M. L. Allende, R. L. Proia, and J. G. Cyster, *Lymphocyte egress from thymus and peripheral lymphoid organs is dependent on SIP receptor* 1. Nature, 2004. 427(6972): p. 355-60.

42 Hashimoto, D., S. Asakura. K. Matsuoka, Y. Sakoda, M. Koyama, K. Aoyama. M. Tanimoto, and T. Teshima, *FTY720 enhances the activation-induced apoptosis of donor T cells and modulates graft-versus-host disease*. Eur J. Immunol. 2007. 37(1): p. 271-81.

43 Taylor, P. A., M. J. Ehrhardt, C. J. Lees. J. Tolar. B. J. Weigel, A. Panoskaltsis-Mortari, J. S. Serody, V. Brinkmann, and B. R. Blazar, *Insights into the mechanism of FTY720 and compatibility with regulatory T cells for the inhibition of graft-versus-host disease (GVHD)*. Blood, 2007. 110(9): p. 3480-8.

44 Kustikova. O., B. Fehse, U. Modlich, M. Yang. J. Dullmann, K. Kamino. N. von Neuhoff. B. Schlegelberger, Z. Li, and C. Baum, *Clonal dominance of hematopoietic stem cells triggered by retroviral gene marking*. Science, 2005. 308(5725): p. 1171-4.

45 Kustikova, O. S. U. Modlich, and B. Fehse, *Retroviral insertion site analysis in dominant haematopoietic clones*. Methods Mol Biol, 2009. 506: p. 373-90.

46 Modlich, U., O. S. Kustikova, M. Schmidt, C. Rudolph, J. Meyer, Z. Li, K. Kamino, N. von Neuhoff, B. Schlegelberger, K. Kuehlcke, K. D. Bunting, S. Schmidt, A. Deichmann, C. von Kalle, B. Fehse, and C. Baum, *Leukemias following retroviral transfer of multidrug resistance 1 (MDR1) are driven by combinatorial insertional mutagenesis*. Blood, 2005. 105(11): p. 4235-46.

47 Robbins, P. F., M. E. Dudley, J. Wunderlich, M. El-Gamil, Y. F. Li, J. Zhou, J. Huang, D. J. Powell, Jr., and S. A. Rosenberg, *Cutting edge: persistence of transferred lymphocyte clonotypes correlates with cancer regression in patients receiving cell transfer therapy*. J Immunol, 2004. 173(12): p. 7125-30.

48 Zhou, J. M. E. Dudley, S. A. Rosenberg, and P. F. Robbins, *Persistence of multiple tumor-specific T-cell clones is associated with complete tumor regression in a melanoma patient receiving adoptive cell transfer therapy*. J Immunother, 2005. 28(1): p. 53-62.

49 Gattinoni, L., C. A. Klebanoff, D. C. Palmer, C. Wrzesinski, K. Kerstann, Z. Yu, S. E. Finkelstein, M. R. Theoret, S. A. Rosenberg, and N. P. Restifo, *Acquisition of full effector function in vitro paradoxically impairs the in vivo antitumor efficacy of adoptively transferred CD8+ T cells*. J Clin Invest, 2005. 115(6): p. 1616-26.

50 Blum. K. S. and R. Pabst, *Lymphocyte numbers and subsets in the human blood. Do they mirror the situation in all organs?* Immunol Lett, 2007. 108(1): p. 45-51.

51 Ganusov, V. V. and R. J. De Boer, *Do most lymphocytes in humans really reside in the gut?* Trends Immunol, 2007. 28(12): p. 514-8.

52 Porter, D. L. B. L. Levine, N. Bunin, E. A. Stadtmauer, S. M. Luger, S. Goldstein, A. Loren, J. Phillips, S. Nasta, A. Perl, S. Schuster, D. Tsai, A. Sohal, E. Veloso, S. Emerson, and C. H. June, *A phase 1 trial of donor lymphocyte infusions expanded and activated ex vivo via CD3/CD28 costimulation*. Blood, 2006. 107(4): p. 1325-31.

53 Rapoport, A. P., B. L. Levine, A. Badros, B. Meisenberg, K. Ruehle, A. Nandi, S. Rollins, S. Natt, B. Ratterree, S. Westphal, D. Mann, and C. H. June, *Molecular remission of CML after autotransplantation followed by adoptive transfer of costimulated autologous T cells*. Bone Marrow Transplant, 2004. 33(1): p. 53-60.

54 Gattinoni, L., X. S. Zhong, D. C. Palmer, Y. Ji, C. S. Hinrichs, Z. Yu, C. Wrzesinski, A. Boni, L. Cassard, L. M. Garvin, C. M. Paulos, P. Muranski, and N. P. Restifo, *Wnt signaling arrests effector T cell differentiation and generates CD8+ memory, stem cells*. Nat Med, 2009. 15(7): p. 80813.

55 Bondanza, A., V. Valtolina, Z. Magnani, M. Ponzoni, K. Fleischhauer, M. Bonyhadi, C. Traversari. F. Sanvito. S. Toma. M. Radrizzani, S. La Seta-Catamancio, F. Ciceri, C. Bordignon, and C. Bonini, *Suicide gene therapy of graft-versus-host disease induced by central memory human T lymphocytes*. Blood, 2006. 107(5): p. 1828-36.

56 Arditti, F. D., S. Aviner, B. Dekel, R. Krauthgamer, J. Gan, A. Nagler, A. Tabilio, M. Martelli, A. Berrebi, and Y. Reisner, *Eradication of B-CLL by autologous and allogeneic host nonreactive anti-third-party CTLs*. Blood, 2005. 105(8): p. 3365-71.

57 Aviner, S., X. Yao, R. Krauthgamer. Y. Gan. R. Goren-Arbel. T. Klein, A. Tabilio, J. D. McMannis, R. Champlin, M. F. Martelli, E. Bachar-Lustig, and Y. Reisner, *Large-scale preparation of human anti-third-party veto cytotoxic T lymphocytes depleted of graft-versus-host reactivity: a new source for graft facilitating cells in bone marrow transplantation*. Hum Immunol, 2005. 66(6): p. 644-52.

58 Tran, K. Q., J. Zhou, K. H. Durflinger. M. M. Langhan, T. E. Shelton. J. R. Wunderlich, P. F. Robbins, S. A. Rosenberg, and M. E. Dudley, *Minimally cultured tumor-infiltrating lymphocytes display optimal characteristics for adoptive cell therapy*. J Immunother, 2008.31(8): p. 742-51.

59 Chen, B. J., D. Deoliveira, X. Cui, N. T. Le, J. Son, J. F. Whitesides, and N. J. Chao, *Inability of memory T cells to induce graft-versus-host disease is a result of an abortive alloresponse*. Blood, 2007. 109(7): p. 3115-23.

60 Kim, Y. M., T. Sachs, W. Asavaroengchai, R. Bronson, and M. Sykes. *Graft-versus-host disease can be separated from graft-versus-lymphoma effects by control of lymphocyte trafficking with FTY720*. J Clin Invest, 2003. 111(5): p. 659-69.

61 Eshhar, Z. The T-body approach: redirecting T cells with antibody specificity. *Handb Exp Pharmacol,* 329-42 (2008).

62 Stephan, M. T. et al. T cell-encoded CD80 and 4-1BBL induce auto- and transcostimulation, resulting in potent tumor rejection. *Nat Med* 13, 1440-9 (2007).

63 Qiao, J. et al. Purging metastases in lymphoid organs using a combination of antigen-nonspecific adoptive T cell therapy, oncolytic virotherapy and immunotherapy. *Nat Med* 14, 37-44 (2008).

64 Haque, T. et al. Allogeneic cytotoxic T-cell therapy for EBV-positive posttransplantation lymphoproliferative disease: results of a phase 2 multicenter clinical trial. *Blood* 110, 1123-31 (2007).

65 Leen, A. M. et al. Cytotoxic T lymphocyte therapy with donor T cells prevents and treats adenovirus and Epstein- Barr virus infections after haploidentical and matched unrelated stem cell transplantation. *Blood* 114, 4283-92 (2009).
66 Melenhorst, J. J. et al. Allogeneic virus-specific T cells with HLA alloreactivity do not produce GVHD in human subjects. *Blood* 116, 4700-2.
67 Amir, A. L. et al. Allo-HLA reactivity of virus-specific memory T cells is common. *Blood* 115, 3146-57.
68 Gaston, J. S. Rickinson, A. B. & Epstein, M. A. Cross-reactivity of self-HLA-restricted Epstein-Barr virus-specific cytotoxic T lymphocytes for allo-HLA determinants. *J Exp Med* 158, 1804-21 (1983).
69 Kaneko, S. et al. IL-7 and IL-15 allow the generation of suicide gene-modified alloreactive self-renewing central memory human T lymphocytes. *Blood* 113, 1006-15 (2009).
70 Edinger. M. et al. Noninvasive assessment of tumor cell proliferation in animal models. *Neoplasia* 1, 303-10 (1999).
71 Pinthus, J. H. et al. Adoptive immunotherapy of prostate cancer bone lesions using redirected effector lymphocytes. *J Clin Invest* 114, 1774-81 (2004).

The invention claimed is:

1. A method of treating cancer, said method comprising subjecting a patient in need of such treatment to partial lymphodepletion, and then administering to the patient an effective amount of alloreactive allogeneic T cells expressing an MHC unrestricted tumor-directed chimeric receptor, wherein said partial lymphodepletion is to an extent sufficient to delay the host versus graft reaction for a period sufficient to allow said allogeneic T cells to attack the tumor to which they are directed, but to an extent insufficient to require rescue of the host immune system by bone marrow transplantation.

2. A method in accordance with claim 1, further including administration of one or more agents that delay egression of the allogeneic T cells from lymph nodes of said subject, after adoptive transfer of said allogeneic T cells to the subject, by trapping the T cells in the lymph nodes.

3. The method of claim 2, wherein the agent that traps T cells in the lymph node is selected from the group consisting of 2-amino-2-[2-(4-octylphenypethyl]propane-1,3-diol (FTY720), 5-[4-phenyl-5-(trifluoromethyl)thiophen-2-yl]-3-[3-(tri fluoromethyl)phenyl]1,2,4-oxadiazole (SEW2871), 3-(2-(-hexylphenylamino)-2-oxoethylamino)propanoic acid (W123), and 2-ammonio-4-(2-chloro-4-(3-phenoxyphenyl-thio)phenyl)-2-(hydroxymethyl)butyl hydrogen phosphate (KRP-203 phosphate).

4. The method of claim 1, wherein the tumor-directed chimeric receptor is antibody-based.

5. The method of claim 1, further comprising inhibiting recognition and elimination of the allogeneic T cells in vivo by recipient's T cells by silencing MHC expression by the allogeneic T cells, to thereby reduce the rejection of the allogeneic cells.

6. The method of claim 5, wherein the silencing of MHC expression has been accomplished by using allogeneic T cells that have been cultured with an shRNA, or an antisense nucleotide, that knocks out MHC expression.

7. The method of claim 1, further comprising inhibiting recognition and elimination of the allogeneic T cells in vivo by recipient's T cells by using allogeneic T cells that have further been engineered to express an inhibitory ligand for NK cells, to thereby reduce the rejection of the allogeneic cells.

8. The method of claim 1, wherein the partial lymphodepletion is accomplished by irradiation treatment, chemotherapy, and/or depleting antibodies.

9. The method of claim 8, wherein the partial lymphodepletion comprises total body irradiation of the patient.

10. The method of claim 8, wherein the partial lymphodepletion comprises administering an effective amount of a lymphodepleting chemotherapeutic agent.

11. The method of claim 10, wherein the lymphodepleting chemotherapeutic agent is cyclophosphamide, fludarabine, busulfan, melphalan or lymphodepleting antibodies.

12. The method of claim 1, further comprising activating and optionally expanding the allogeneic T cells before the administering step.

13. The method of claim 11, wherein the allogeneic T cells are activated in vitro with CD3/CD28 antibodies and the allogeneic T cells are further expanded with IL-2, IL-7, IL-15, and/or IL-21.

14. The method of claim 1, wherein the amount of allogeneic T cells administered is sufficient to return the lymphodepleted lymphocyte population to its homeostatic amount.

15. The method of claim 1, wherein the allogeneic T cells are administered in one or more doses.

* * * * *